(12) United States Patent
Davis et al.

(10) Patent No.: US 7,125,693 B2
(45) Date of Patent: Oct. 24, 2006

(54) ENZYMATIC PROCESSES FOR THE PRODUCTION OF 4-SUBSTITUTED 3-HYDROXYBUTYRIC ACID DERIVATIVES

(75) Inventors: S. Christopher Davis, San Francisco, CA (US); John H. Grate, Los Altos, CA (US); David R. Gray, Walnut Creek, CA (US); John M. Gruber, Mountain View, CA (US); Gjalt W. Huisman, San Carlos, CA (US); Steven K. Ma, Foster City, CA (US); Lisa M. Newman, Redwood City, CA (US); Roger Sheldon, Rijswijk (NL); Li A Wang, Palo Alto, CA (US)

(73) Assignee: Codexis, Inc., Redwood City, CA (US)

( * ) Notice: Subject to any disclaimer, the term of this patent is extended or adjusted under 35 U.S.C. 154(b) by 336 days.

(21) Appl. No.: 10/639,159

(22) Filed: Aug. 11, 2003

(65) Prior Publication Data

US 2004/0137585 A1 Jul. 15, 2004

Related U.S. Application Data

(60) Provisional application No. 60/402,436, filed on Aug. 9, 2002.

(51) Int. Cl.
*C12P 13/00* (2006.01)
(52) U.S. Cl. .................................................. 435/128
(58) Field of Classification Search ................ 435/128
See application file for complete search history.

(56) References Cited

U.S. PATENT DOCUMENTS

| | | | |
|---|---|---|---|
| 4,397,952 A | 8/1983 | Von Hoerschelmann et al. |
| 4,542,098 A | 9/1985 | Vandecasteele et al. |
| 4,877,733 A | 10/1989 | Takahashi et al. |
| 5,114,853 A | 5/1992 | Makino et al. |
| 5,126,256 A | 6/1992 | Ebeling et al. |
| 5,137,821 A | 8/1992 | Sagai et al. |
| 5,166,061 A | 11/1992 | Nakamura et al. |
| 5,210,031 A | 5/1993 | Nakamura et al. |
| 5,244,796 A | 9/1993 | Levy et al. |
| 5,250,415 A | 10/1993 | Ebeling et al. |
| 5,298,411 A | 3/1994 | Sogabe et al. |
| 5,385,833 A | 1/1995 | Bradshaw et al. |
| 5,413,921 A | 5/1995 | Onishi et al. |
| 5,430,171 A | 7/1995 | Mitsuhashi et al. |
| 5,523,223 A | 6/1996 | Kula et al. |
| 5,559,030 A | 9/1996 | Matsuyama et al. |
| 5,700,670 A | 12/1997 | Yamagishi et al. |
| 5,891,685 A | 4/1999 | Yamagishi et al. |
| 5,908,953 A | 6/1999 | Matsuda et al. |
| 6,001,615 A | 12/1999 | Reeve |
| 6,001,618 A | 12/1999 | Kimoto et al. |
| 6,140,527 A | 10/2000 | Kunihiro et al. |
| 6,168,935 B1 | 1/2001 | Yamamoto |
| 6,218,156 B1 | 4/2001 | Yasohara et al. |
| 6,218,157 B1 | 4/2001 | Kimoto et al. |
| 6,312,933 B1 | 11/2001 | Kimoto et al. |
| 6,344,569 B1 | 2/2002 | Mitsuda et al. |
| 6,448,052 B1 | 9/2002 | Yasohara et al. |
| 6,472,544 B1 | 10/2002 | Kizaki et al. |
| 6,596,879 B1 | 7/2003 | Bosch et al. |
| 6,645,746 B1 | 11/2003 | Kizaki et al. |
| 6,689,591 B1 | 2/2004 | Muller et al. |
| 2002/0045233 A1 | 4/2002 | Hershberger et al. |
| 2005/0095619 A1 | 5/2005 | Davis et al. |
| 2005/0153417 A1 | 7/2005 | Davis et al. |
| 2005/0272064 A1 | 12/2005 | Davis et al. |

FOREIGN PATENT DOCUMENTS

| | | |
|---|---|---|
| EP | 0 967 271 A1 | 12/1999 |
| EP | 1 416 050 A1 | 5/2004 |
| WO | WO 01/90397 A1 | 11/2001 |
| WO | WO 2004-015132 A2 | 2/2004 |
| WO | WO 05/017135 A1 | 2/2005 |
| WO | WO 05/017141 A1 | 2/2005 |
| WO | WO 05/018579 A2 | 3/2005 |
| WO | WO 05/045016 A2 | 5/2005 |

OTHER PUBLICATIONS

Bayer, M. et al., *Applied Microbiology and Biotechnology* (1994) 42(1):40-45.
Bock, K., et al., *Acta Chemica Scandinavica* (1983) B37:341-344.
Bradshaw, C. W., et al., *J. Org. Chem.* (1992) 57:1526-1532.
Hallinan, K. O., et al., *Biocatalysis and Biotransformation* (1995) 12:179-191.
Isbell, H.S., et al., Carbohydrate Research (1979) 72:301-304.
Kataoka, M., et al., Biochim et Biophysica Acta (1992) 1122:57-62.
Kataoka, M., et al., *Archives of Biochem. And BioPhysics* (1992) 294(2):469-474.
Kataoka, M., et al., *Appl. Microbiol. Biotechnol.* (1997) 48:699-703.
Kato, N., et al., *Biosci. Biotech. Biochem.* (1993) 57(2):303-307.
Mitamura, T., et al., *J. of Fermentation and Bioengineering* (1990) 70(6):363-369.
Nagasawa, T., et al., *Appl. Microbiol. and Biotechnol.* (1992) 36:478-482.
Nakamura, T., et al., *Tetrahedron* (1994) 50(41):11821-11826.
Nakamura, K., et al., *Biosci. Biotech. Biochem.* (1994) 58(12):2236-2240.

(Continued)

Primary Examiner—Herbert J. Lilling
(74) Attorney, Agent, or Firm—Dechert LLP

(57) ABSTRACT

The present invention provides methods and compositions for preparing 4-substituted 3-hydroxybutyric acid derivatives by halohydrin dehalogenase-catalyzed conversion of 4-halo-3-hydroxybutyric acid derivatives. The present invention further provides methods and compositions for preparing 4-halo-3-hydroxybutyric acid derivatives by ketoreductase-catalyzed conversion of 4-halo-3-ketobutyric acid derivatives.

34 Claims, 3 Drawing Sheets

OTHER PUBLICATIONS

Nakamura, T., et al., *Applied and Environmental Microbiology* (1994) 60(4):1297-1301.
Nakamura, T., et al., *Biochem. And Biophys. Research Comm.* (1991) 180(1):124-130.
Nakamura, K., et al., *Tetrahedron Letters* (1988) 29(20):2453-2454.
Nakamura, K., et al., *J. Org. Chem.* (1991) 56:4778-4783.
Patel, R. N., et al., *Enzyme Microb. Technol.* (1992) 14:731-738.
Peters, J., et al., Enzyme *Microbiol. Biotechnol.* (1993) 15:950-958.
Peters, J., et al., *Applied Microb Biotehnol* (1992) 38:334-340.
Shimizu, S., et al., *Biotechnology Letters* (1990) 12(8):593-596.
Shimizu, S., et al., *Applied and Environmental Microbiology* (1990) 56(8):2374-2377.
Shimizu, S. et al., *Am. NY Acad. Of Science* (1990) 613:628-632.
Lutje Spelberg, J.H., et al., *Tetrahedron: Asymmetry* (2002) 13:1083-1089.
Lutje Spelberg, J.H., et al., *Organic Letters* (2001) 3(1):41-43.
Swanson, P. E., *Current Opinion in Biotechnology* (1999) 10:365-369.
Tang, L., et al., *Enzyme and Microbial Technology* (2002) 30:251-258.
Trincone, A., et al., *Biotechnology Letters* (1991) 13(1):31-34.
Vlieg, Van Hylckama, J. E. T., et al. *J. of Bacteriology* (2001) 183(17):5058-5066.
Wong, C-H, et al., *J. Am. Chem. Soc.* (1985) 107-4028-4031.
Wong, C-H, et al., *J. Am Chem. Soc.* (1981) 103:4890-4899.
Yamada, H., et al., *FEMS Microbiology Letters* (1990) 70:45-48.
Yamazaki, Y., et al., *Agric. Biol. Chem.* (1982) 46(6):1571-1581.
Yasohara, Y., et al., *Appl. Microbiol Biotechnol.* (1999) 51:847-851.
Zelinski, T., et al., *Journal of Biotechnology* (1994) 33:283-292.
Database EMBL [ONLINE] Jun. 3, 1999, Lewis, M.: "*Agrobacterium tumefaciens* haloalcohol dehalogenase B gene, complete CDs."XPOO2305665 retrieved from EBI accession No. EM_PRO:AF149769.
De Jong, R.M. et al., "Structure and mechanism of a bacterial haloalcohol dehalogenase: a new variation of the short-chain dehydrogenase/reductase fold without an NAD(P)H binding site," *The EMBO Journal* 22(19):4933-4944 (2003) XP-002305279.
Lampel, K.A. et al., "Characterization of the Developmentally Regulated Facillus-Subtillis Glucose Dehydrogenase Gene", *Journal of Bacteriology*, 166(1):238-243 (1986) XP-002327631.
Manjon A. et al., "Increased Activity of Glucose Dehydrogenase Co-Immobilized with a Redox Mediator in a Bioreactor with Electrochemical NAD+ Regeneration", *Biotechnology Letters*, 24(15):1227-1232 (2002).
Tang, Lixia et al., "Steady-state kinetics and tryptophan fluorescence properties of halohydrin dehalogenase from *Agrobactrium radiobacter* roles of W139 and W249 in the active site and halide-induced conformational change," *Biochemistry* 42:14057-14065 (2003) XP-0023005278.
Yasohara, Y. et al., "Molecular cloning and overexpression of the gene encoding an NADPH-dependent carbonyl reductase from *Candida magnoliae* , involved in stereoselective reduction of ethyl 4-chloro-3-oxburanoate," *Bioscience Biotechnology Biochemistry, Japan Soco. For Bioscience, Biotechnology and Agrochem* 64(7) 1430-1436 (Jul. 2000).

SEQUENCE LISTING

```
<160> NUMBER OF SEQ ID NOS: 92

<210> SEQ ID NO 1
<211> LENGTH: 852
<212> TYPE: DNA
<213> ORGANISM: Artificial Sequence
<220> FEATURE:
<221> NAME/KEY: CDS
<222> LOCATION: (1)...(852)
<223> OTHER INFORMATION: Ketoreductase 1
<220> FEATURE:
<223> OTHER INFORMATION: KRED CR2-5

<400> SEQUENCE: 1 atg gca aag aat ttt agc aat gta gag tat ccc gca ccc ccc ccc gca      48
Met Ala Lys Asn Phe Ser Asn Val Glu Tyr Pro Ala Pro Pro Pro Ala
 1               5                  10                  15 cat aca aag aat gag agc tta caa gta tta gat tta ttt aag tta aat      96
His Thr Lys Asn Glu Ser Leu Gln Val Leu Asp Leu Phe Lys Leu Asn
            20                  25                  30 gga aaa gta gca agc ata aca gga agc agc agc gga ata gga tat gca     144
Gly Lys Val Ala Ser Ile Thr Gly Ser Ser Ser Gly Ile Gly Tyr Ala
        35                  40                  45 tta gca gag gct ttt gca caa gtc gga gca gat gta gca ata tgg tat     192
Leu Ala Glu Ala Phe Ala Gln Val Gly Ala Asp Val Ala Ile Trp Tyr
    50                  55                  60 aat agc cat gat gca aca gga aaa gca gag gca tta gca aag aag tat     240
Asn Ser His Asp Ala Thr Gly Lys Ala Glu Ala Leu Ala Lys Lys Tyr
65                  70                  75                  80 gga gta aag gta aag gca tat aaa gca aat gta agc agc agc gat gca     288
Gly Val Lys Val Lys Ala Tyr Lys Ala Asn Val Ser Ser Ser Asp Ala
                85                  90                  95 gtc aag caa aca ata gag caa caa ata aag gat ttt gga cat tta gat     336
Val Lys Gln Thr Ile Glu Gln Gln Ile Lys Asp Phe Gly His Leu Asp
            100                 105                 110 ata gta gta gca aat gca gga ata ccc tgg aca aag gga gca tat ata     384
Ile Val Val Ala Asn Ala Gly Ile Pro Trp Thr Lys Gly Ala Tyr Ile
        115                 120                 125 gat caa gat gat gac aag cat ttt gac caa gta gta gat gta gac tta     432
Asp Gln Asp Asp Asp Lys His Phe Asp Gln Val Val Asp Val Asp Leu
    130                 135                 140 aag gga gta gga tac gta gca aag cat gca gga agg cat ttt agg gaa     480
Lys Gly Val Gly Tyr Val Ala Lys His Ala Gly Arg His Phe Arg Glu
145                 150                 155                 160 agg ttt gag aaa gag gga aaa aag gga gca tta gta ttt aca gca agc     528
Arg Phe Glu Lys Glu Gly Lys Lys Gly Ala Leu Val Phe Thr Ala Ser
                165                 170                 175 atg agc gga cat ata gta aat gtc ccc caa ttc caa gca aca tat aat     576
Met Ser Gly His Ile Val Asn Val Pro Gln Phe Gln Ala Thr Tyr Asn
            180                 185                 190 gca gca aag gca gga gta agg cat ttt gca aag agc tta gca gtc gag     624
Ala Ala Lys Ala Gly Val Arg His Phe Ala Lys Ser Leu Ala Val Glu
```

-continued

```
                    195                 200                 205
ttt gca ccc ttt gca agg gta aat agc gta agc ccc gga tat ata aat    672
Phe Ala Pro Phe Ala Arg Val Asn Ser Val Ser Pro Gly Tyr Ile Asn
        210                 215                 220 aca gag ata agc gat ttc gtc ccc caa gag aca caa aat aag tgg tgg    720
Thr Glu Ile Ser Asp Phe Val Pro Gln Glu Thr Gln Asn Lys Trp Trp
225                 230                 235                 240 agc tta gtc ccc tta gga agg gga gga gag aca gca gag tta gta gga    768
Ser Leu Val Pro Leu Gly Arg Gly Gly Glu Thr Ala Glu Leu Val Gly
                245                 250                 255 gca tat tta ttc tta gca agc gat gca gga agc tat gca aca gga aca    816
Ala Tyr Leu Phe Leu Ala Ser Asp Ala Gly Ser Tyr Ala Thr Gly Thr
            260                 265                 270 gat ata ata gta gat gga gga tat aca tta ccc taa                    852
Asp Ile Ile Val Asp Gly Gly Tyr Thr Leu Pro *
        275                 280
```

<210> SEQ ID NO 2
<211> LENGTH: 283
<212> TYPE: PRT
<213> ORGANISM: Candida magnoliae

<400> SEQUENCE: 2

```
Met Ala Lys Asn Phe Ser Asn Val Glu Tyr Pro Ala Pro Pro Pro Ala
1               5                   10                  15

His Thr Lys Asn Glu Ser Leu Gln Val Leu Asp Leu Phe Lys Leu Asn
                20                  25                  30

Gly Lys Val Ala Ser Ile Thr Gly Ser Ser Ser Gly Ile Gly Tyr Ala
            35                  40                  45

Leu Ala Glu Ala Phe Ala Gln Val Gly Ala Asp Val Ala Ile Trp Tyr
        50                  55                  60

Asn Ser His Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Ser Asp Ala
                85                  90                  95

Val Lys Gln Thr Ile Glu Gln Gln Ile Lys Asp Phe Gly His Leu Asp
                100                 105                 110

Ile Val Val Ala Asn Ala Gly Ile Pro Trp Thr Lys Gly Ala Tyr Ile
            115                 120                 125

Asp Gln Asp Asp Asp Lys His Phe Asp Gln Val Val Asp Val Asp Leu
        130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Ala Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
        210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
```

-continued

```
                    260                 265                 270
Asp Ile Val Asp Gly Gly Tyr Thr Leu Pro
        275                 280

<210> SEQ ID NO 3
<211> LENGTH: 852
<212> TYPE: DNA
<213> ORGANISM: Artificial Sequence
<220> FEATURE:
<221> NAME/KEY: CDS
<222> LOCATION: (1)...(852)
<223> OTHER INFORMATION: Ketoreductase 2
<220> FEATURE:
<223> OTHER INFORMATION: (KRED CR1-2)

<400> SEQUENCE: 3 atg gca aag aat ttt agc aat gta gag tat ccc gca ccc ccc ccc gca    48
Met Ala Lys Asn Phe Ser Asn Val Glu Tyr Pro Ala Pro Pro Pro Ala
1               5                   10                  15 cat aca aag aat gag agc tta caa gta tta gat tta ttt aag tta aat    96
His Thr Lys Asn Glu Ser Leu Gln Val Leu Asp Leu Phe Lys Leu Asn
            20                  25                  30 gga aaa gta gca agc ata aca gga agc agc agc gga ata gga tat gca   144
Gly Lys Val Ala Ser Ile Thr Gly Ser Ser Ser Gly Ile Gly Tyr Ala
        35                  40                  45 tta gca gag gct ttt gca caa gtc gga gca gat gta gca ata tgg tat   192
Leu Ala Glu Ala Phe Ala Gln Val Gly Ala Asp Val Ala Ile Trp Tyr
    50                  55                  60 aat agc cat gat gca aca gga aaa gca gag gca tta gca aag aag tat   240
Asn Ser His Asp Ala Thr Gly Lys Ala Glu Ala Leu Ala Lys Lys Tyr
65                  70                  75                  80 gga gta aag gta aag gca tat aaa gca aat gta agc agc agc gat gca   288
Gly Val Lys Val Lys Ala Tyr Lys Ala Asn Val Ser Ser Ser Asp Ala
                85                  90                  95 gtc aag caa aca ata gag caa caa ata aag gat ttt gga cat tta gat   336
Val Lys Gln Thr Ile Glu Gln Gln Ile Lys Asp Phe Gly His Leu Asp
            100                 105                 110 ata gta gca gca aat gca gga ata ccc tgg aca aag gga gca tat ata   384
Ile Val Ala Ala Asn Ala Gly Ile Pro Trp Thr Lys Gly Ala Tyr Ile
        115                 120                 125 gat caa gat gat gac aag cat ttt gac caa gta gta gat gta gac tta   432
Asp Gln Asp Asp Asp Lys His Phe Asp Gln Val Val Asp Val Asp Leu
    130                 135                 140 aag gga gta gga tac gta gca aag cat gca gga agg cat ttt agg gaa   480
Lys Gly Val Gly Tyr Val Ala Lys His Ala Gly Arg His Phe Arg Glu
145                 150                 155                 160 agg ttt gag aaa gag gga aaa aag gga gca tta gta ttt aca gca agc   528
Arg Phe Glu Lys Glu Gly Lys Lys Gly Ala Leu Val Phe Thr Ala Ser
                165                 170                 175 atg agc gga cat ata gta aat gtc ccc caa ttc caa gca aca tat aat   576
Met Ser Gly His Ile Val Asn Val Pro Gln Phe Gln Ala Thr Tyr Asn
            180                 185                 190 gca gca aag gca gga gta agg cat ttt gca aag agc tta gca gtc gag   624
Ala Ala Lys Ala Gly Val Arg His Phe Ala Lys Ser Leu Ala Val Glu
        195                 200                 205 ttt gca ccc ttt gca agg gta aat agc gta agc ccc gga tat ata aat   672
Phe Ala Pro Phe Ala Arg Val Asn Ser Val Ser Pro Gly Tyr Ile Asn
    210                 215                 220 aca gag ata agc gat ttc gtc ccc caa gag aca caa aat aag tgg tgg   720
Thr Glu Ile Ser Asp Phe Val Pro Gln Glu Thr Gln Asn Lys Trp Trp
225                 230                 235                 240
```

```
agc tta gtc ccc tta gga agg gga gga gag aca gca gag tta gta gga       768
Ser Leu Val Pro Leu Gly Arg Gly Gly Glu Thr Ala Glu Leu Val Gly
                245                 250                 255 gca tat tta ttc tta gca agc gat gca gga agc tat gca aca gga aca       816
Ala Tyr Leu Phe Leu Ala Ser Asp Ala Gly Ser Tyr Ala Thr Gly Thr
            260                 265                 270 gat ata ata gta gat gga gga tat aca tta ccc taa                       852
Asp Ile Ile Val Asp Gly Gly Tyr Thr Leu Pro *
            275                 280
```

<210> SEQ ID NO 4
<211> LENGTH: 283
<212> TYPE: PRT
<213> ORGANISM: Candida magnoliae

<400> SEQUENCE: 4

```
Met Ala Lys Asn Phe Ser Asn Val Glu Tyr Pro Ala Pro Pro Pro Ala
 1               5                  10                  15

His Thr Lys Asn Glu Ser Leu Gln Val Leu Asp Leu Phe Lys Leu Asn
            20                  25                  30

Gly Lys Val Ala Ser Ile Thr Gly Ser Ser Ser Gly Ile Gly Tyr Ala
        35                  40                  45

Leu Ala Glu Ala Phe Ala Gln Val Gly Ala Asp Val Ala Ile Trp Tyr
    50                  55                  60

Asn Ser His Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Ser Asp Ala
                85                  90                  95

Val Lys Gln Thr Ile Glu Gln Gln Ile Lys Asp Phe Gly His Leu Asp
            100                 105                 110

Ile Val Ala Ala Asn Ala Gly Ile Pro Trp Thr Lys Gly Ala Tyr Ile
        115                 120                 125

Asp Gln Asp Asp Asp Lys His Phe Asp Gln Val Val Asp Val Asp Leu
    130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Ala Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
    210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
        275                 280
```

<210> SEQ ID NO 5
<211> LENGTH: 852
<212> TYPE: DNA
<213> ORGANISM: Artificial Sequence
<220> FEATURE:
<221> NAME/KEY: CDS
<222> LOCATION: (1)...(852)
<223> OTHER INFORMATION: Ketoreductase 3
<220> FEATURE:
<223> OTHER INFORMATION: (KRED CR1-3)

<400> SEQUENCE: 5

| | | |
|---|---|---|
| atg gca aag aat ttt agc aat gtg gag tat ccc gca ccc ccc ccc gca<br>Met Ala Lys Asn Phe Ser Asn Val Glu Tyr Pro Ala Pro Pro Pro Ala<br>1               5                    10                 15 | 48 |
| cat aca aag aat gag agc tta caa gta tta gat tta ttt aag tta aat<br>His Thr Lys Asn Glu Ser Leu Gln Val Leu Asp Leu Phe Lys Leu Asn<br>              20                    25                    30 | 96 |
| gga aaa gta gca agc ata aca gga agc agc agc gga ata gga tat gca<br>Gly Lys Val Ala Ser Ile Thr Gly Ser Ser Ser Gly Ile Gly Tyr Ala<br>       35                    40                    45 | 144 |
| tta gca gag gct ttt gca caa gtc gga gca gat gta gca ata tgg tat<br>Leu Ala Glu Ala Phe Ala Gln Val Gly Ala Asp Val Ala Ile Trp Tyr<br>    50                    55                    60 | 192 |
| aat agc cat gat gca aca gga aaa gca gag gca tta gca aag aag tat<br>Asn Ser His Asp Ala Thr Gly Lys Ala Glu Ala Leu Ala Lys Lys Tyr<br>65                   70                    75                    80 | 240 |
| gga gta aag gta aag gca tat aaa gca aat gta agc agc agc gat gca<br>Gly Val Lys Val Lys Ala Tyr Lys Ala Asn Val Ser Ser Ser Asp Ala<br>              85                    90                    95 | 288 |
| gtc aag caa aca ata gag caa caa ata aag gat ttt gga cat tta gat<br>Val Lys Gln Thr Ile Glu Gln Gln Ile Lys Asp Phe Gly His Leu Asp<br>              100                  105                110 | 336 |
| ata gta gta gca aat gca gga ata ccc tgg aca aag gga gca tat ata<br>Ile Val Val Ala Asn Ala Gly Ile Pro Trp Thr Lys Gly Ala Tyr Ile<br>       115                    120                  125 | 384 |
| gat caa gat gat gac aag cat ttt gac caa gta gta gat gta gac tta<br>Asp Gln Asp Asp Asp Lys His Phe Asp Gln Val Val Asp Val Asp Leu<br>130                     135                  140 | 432 |
| aag gga gta gga tac gta gca aag cat gca gga agg cat ttt agg gaa<br>Lys Gly Val Gly Tyr Val Ala Lys His Ala Gly Arg His Phe Arg Glu<br>145                     150                  155                160 | 480 |
| agg ttt gag aaa gag gga aaa aag gga gca tta gta ttt aca gca agc<br>Arg Phe Glu Lys Glu Gly Lys Lys Gly Ala Leu Val Phe Thr Ala Ser<br>              165                  170                175 | 528 |
| atg agc gga cat ata gta aat gtc ccc caa ttc caa gca aca tat aat<br>Met Ser Gly His Ile Val Asn Val Pro Gln Phe Gln Ala Thr Tyr Asn<br>       180                    185                  190 | 576 |
| gca gca aag gca gga gta agg cat ttt gca aag agc tta gca gtc gag<br>Ala Ala Lys Ala Gly Val Arg His Phe Ala Lys Ser Leu Ala Val Glu<br>    195                    200                  205 | 624 |
| ttt gca ccc ttt gca agg gta aat agc gta agc ccc gga tat ata aat<br>Phe Ala Pro Phe Ala Arg Val Asn Ser Val Ser Pro Gly Tyr Ile Asn<br>210                     215                  220 | 672 |
| aca gag ata agc gat ttc gtc ccc caa gag aca caa aat aag tgg tgg<br>Thr Glu Ile Ser Asp Phe Val Pro Gln Glu Thr Gln Asn Lys Trp Trp<br>225                     230                  235                240 | 720 |
| agc tta gtc ccc tta gga agg gga gga gag aca gca gag tta gta gga<br>Ser Leu Val Pro Leu Gly Arg Gly Gly Glu Thr Ala Glu Leu Val Gly<br>              245                  250                255 | 768 |
| gca tat tta ttc tta gca agc gat gca gga agc tat gca aca gga aca<br>Ala Tyr Leu Phe Leu Ala Ser Asp Ala Gly Ser Tyr Ala Thr Gly Thr<br>       260                    265                  270 | 816 |
| gat ata ata gta gat gga gga tat aca tta ccc taa<br>Asp Ile Ile Val Asp Gly Gly Tyr Thr Leu Pro * | 852 |

```
                    275                 280

<210> SEQ ID NO 6
<211> LENGTH: 283
<212> TYPE: PRT
<213> ORGANISM: Candida magnoliae

<400> SEQUENCE: 6

Met Ala Lys Asn Phe Ser Asn Val Glu Tyr Pro Ala Pro Pro Pro Ala
 1               5                  10                  15

His Thr Lys Asn Glu Ser Leu Gln Val Leu Asp Leu Phe Lys Leu Asn
            20                  25                  30

Gly Lys Val Ala Ser Ile Thr Gly Ser Ser Ser Gly Ile Gly Tyr Ala
        35                  40                  45

Leu Ala Glu Ala Phe Ala Gln Val Gly Ala Asp Val Ala Ile Trp Tyr
     50                  55                  60

Asn Ser His Asp Ala Thr Gly Lys Ala Glu Ala Leu Ala Lys Lys Tyr
 65                  70                  75                  80

Gly Val Lys Val Lys Ala Tyr Lys Ala Asn Val Ser Ser Ser Asp Ala
                85                  90                  95

Val Lys Gln Thr Ile Glu Gln Ile Lys Asp Phe Gly His Leu Asp
            100                 105                 110

Ile Val Val Ala Asn Ala Gly Ile Pro Trp Thr Lys Gly Ala Tyr Ile
        115                 120                 125

Asp Gln Asp Asp Asp Lys His Phe Asp Gln Val Asp Val Asp Leu
    130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Ala Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
    210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
        275                 280

<210> SEQ ID NO 7
<211> LENGTH: 852
<212> TYPE: DNA
<213> ORGANISM: Artificial Sequence
<220> FEATURE:
<221> NAME/KEY: CDS
<222> LOCATION: (1)...(852)
<223> OTHER INFORMATION: Ketoreductase 4
<220> FEATURE:
<223> OTHER INFORMATION: KRED CR2-4

<400> SEQUENCE: 7 atg gca aag aat ttt agc aat gta gag tat ccc gca ccc ccc ccc gca        48
```

```
Met Ala Lys Asn Phe Ser Asn Val Glu Tyr Pro Ala Pro Pro Pro Ala
 1               5                  10                  15 cat aca aag aat gag agc tta caa gta tta gat tta ttt aag tta aat       96
His Thr Lys Asn Glu Ser Leu Gln Val Leu Asp Leu Phe Lys Leu Asn
             20                  25                  30 gga aaa gta gca agc ata aca gga agc agc agc gga ata gga tat gca      144
Gly Lys Val Ala Ser Ile Thr Gly Ser Ser Ser Gly Ile Gly Tyr Ala
         35                  40                  45 tta gca gag gct ttt gca caa gtc gga gca gat gta gca ata tgg tat      192
Leu Ala Glu Ala Phe Ala Gln Val Gly Ala Asp Val Ala Ile Trp Tyr
     50                  55                  60 aat agc cat gat gca aca gga aaa gca gag gca tta gca aag aag tat      240
Asn Ser His Asp Ala Thr Gly Lys Ala Glu Ala Leu Ala Lys Lys Tyr
 65                  70                  75                  80 gga gta aag gta aag gca tat aaa gca aat gta agc agc agc gat gca      288
Gly Val Lys Val Lys Ala Tyr Lys Ala Asn Val Ser Ser Ser Asp Ala
                 85                  90                  95 gtc aag caa aca ata gag caa caa ata aag gat ttt gga cat tta gat      336
Val Lys Gln Thr Ile Glu Gln Gln Ile Lys Asp Phe Gly His Leu Asp
             100                 105                 110 ata gta gta gca aat gca gga ata ccc tgg aca aag gga gca tat ata      384
Ile Val Val Ala Asn Ala Gly Ile Pro Trp Thr Lys Gly Ala Tyr Ile
         115                 120                 125 gat caa gat gat gac aag cat ttt gac caa gta gta gat gta gac tta      432
Asp Gln Asp Asp Asp Lys His Phe Asp Gln Val Val Asp Val Asp Leu
    130                 135                 140 aag gga gta gga tac gta gca aag cat gca gga agg cat ttt agg gaa      480
Lys Gly Val Gly Tyr Val Ala Lys His Ala Gly Arg His Phe Arg Glu
145                 150                 155                 160 agg ttt gag aaa gag gga aaa aag gga gca tta gta ttt aca gca agc      528
Arg Phe Glu Lys Glu Gly Lys Lys Gly Ala Leu Val Phe Thr Ala Ser
                165                 170                 175 atg agc gga cat ata gta aat gtc ccc caa ttc caa gca aca tat aat      576
Met Ser Gly His Ile Val Asn Val Pro Gln Phe Gln Ala Thr Tyr Asn
            180                 185                 190 gca gca aag gca gga gta agg cat ttt gca aag agc tta gca gtc gag      624
Ala Ala Lys Ala Gly Val Arg His Phe Ala Lys Ser Leu Ala Val Glu
        195                 200                 205 ttt gca ccc ttt gca agg gta aat agc gta agc ccc gga tat ata aat      672
Phe Ala Pro Phe Ala Arg Val Asn Ser Val Ser Pro Gly Tyr Ile Asn
    210                 215                 220 aca gag ata agc gat ttc gtc ccc caa gag aca caa aat aag tgg tgg      720
Thr Glu Ile Ser Asp Phe Val Pro Gln Glu Thr Gln Asn Lys Trp Trp
225                 230                 235                 240 agc tta gtc ccc tta gga agg gga gga gag aca gca gag tta gta gga      768
Ser Leu Val Pro Leu Gly Arg Gly Gly Glu Thr Ala Glu Leu Val Gly
                245                 250                 255 gca tat tta ttc tta gca agc gat gca gga agc tat gca aca gga aca      816
Ala Tyr Leu Phe Leu Ala Ser Asp Ala Gly Ser Tyr Ala Thr Gly Thr
            260                 265                 270 gat ata ata gta gat gga gga tat act tta ccc taa                      852
Asp Ile Ile Val Asp Gly Gly Tyr Thr Leu Pro *
        275                 280

<210> SEQ ID NO 8
<211> LENGTH: 283
<212> TYPE: PRT
<213> ORGANISM: Candida magnoliae

<400> SEQUENCE: 8
```

```
Met Ala Lys Asn Phe Ser Asn Val Glu Tyr Pro Ala Pro Pro Ala
 1               5                  10                  15

His Thr Lys Asn Glu Ser Leu Gln Val Leu Asp Leu Phe Lys Leu Asn
                20                  25                  30

Gly Lys Val Ala Ser Ile Thr Gly Ser Ser Ser Gly Ile Gly Tyr Ala
            35                  40                  45

Leu Ala Glu Ala Phe Ala Gln Val Gly Ala Asp Val Ala Ile Trp Tyr
50                      55                  60

Asn Ser His Asp Ala Thr Gly Lys Ala Glu Ala Leu Ala Lys Lys Tyr
65                      70                  75                  80

Gly Val Lys Val Lys Ala Tyr Lys Ala Asn Val Ser Ser Ser Asp Ala
                85                  90                  95

Val Lys Gln Thr Ile Glu Gln Ile Lys Asp Phe Gly His Leu Asp
                100                 105                 110

Ile Val Val Ala Asn Ala Gly Ile Pro Trp Thr Lys Gly Ala Tyr Ile
            115                 120                 125

Asp Gln Asp Asp Asp Lys His Phe Asp Gln Val Val Asp Val Asp Leu
        130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Ala Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
        275                 280

<210> SEQ ID NO 9
<211> LENGTH: 786
<212> TYPE: DNA
<213> ORGANISM: Bacillus sp.
<220> FEATURE:
<221> NAME/KEY: CDS
<222> LOCATION: (1)...(786)
<223> OTHER INFORMATION: Glucose dehydrogenase S06-3

<400> SEQUENCE: 9 atg tat ccg gat tta aaa gga aaa gtc gtc gct att aca gga gct gct    48
Met Tyr Pro Asp Leu Lys Gly Lys Val Val Ala Ile Thr Gly Ala Ala
 1               5                  10                  15 tca ggg ctc gga aag gcg atg gcc att cgc ttc ggc aag gag cag gca    96
Ser Gly Leu Gly Lys Ala Met Ala Ile Arg Phe Gly Lys Glu Gln Ala
                20                  25                  30 aaa gtg gtt atc aac tat tat agt aat aaa caa gat ccg aac gag gta   144
Lys Val Val Ile Asn Tyr Tyr Ser Asn Lys Gln Asp Pro Asn Glu Val
            35                  40                  45 aaa gaa gag gtc atc aag gcg ggc ggt gaa gct gtt gtc gtc caa gga   192
```

-continued

```
Lys Glu Glu Val Ile Lys Ala Gly Glu Ala Val Val Gln Gly
     50                  55                  60 gat gtc acg aaa gag gaa gat gta aaa aat atc gtg caa acg gca att      240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa      288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
             100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
         115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
     130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac      528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat      624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly *
            260
```

<210> SEQ ID NO 10
<211> LENGTH: 261
<212> TYPE: PRT
<213> ORGANISM: Bacillus sp.

<400> SEQUENCE: 10

```
Met Tyr Pro Asp Leu Lys Gly Lys Val Ala Ile Thr Gly Ala Ala
 1               5                  10                  15

Ser Gly Leu Gly Lys Ala Met Ala Ile Arg Phe Gly Lys Glu Gln Ala
                 20                  25                  30

Lys Val Val Ile Asn Tyr Tyr Ser Asn Lys Gln Asp Pro Asn Glu Val
             35                  40                  45

Lys Glu Glu Val Ile Lys Ala Gly Gly Glu Ala Val Val Gln Gly
         50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
```

```
                       85                  90                  95
Asn Pro Val Pro Ser His Glu Met Pro Leu Lys Asp Trp Asp Lys Val
                100                 105                 110
Ile Gly Thr Asn Leu Thr Gly Ala Phe Leu Gly Ser Arg Glu Ala Ile
            115                 120                 125
Lys Tyr Phe Val Glu Asn Asp Ile Lys Gly Asn Val Ile Asn Met Ser
        130                 135                 140
Ser Val His Glu Val Ile Pro Trp Pro Leu Phe Val His Tyr Ala Ala
145                 150                 155                 160
Ser Lys Gly Gly Ile Lys Leu Met Thr Glu Thr Leu Ala Leu Glu Tyr
                165                 170                 175
Ala Pro Lys Gly Ile Arg Val Asn Asn Ile Gly Pro Gly Ala Ile Asn
            180                 185                 190
Thr Pro Ile Asn Ala Glu Lys Phe Ala Asp Pro Lys Gln Lys Ala Asp
        195                 200                 205
Val Glu Ser Met Ile Pro Met Gly Tyr Ile Gly Glu Pro Glu Glu Ile
210                 215                 220
Ala Ala Val Ala Ala Trp Leu Ala Ser Lys Glu Ala Ser Tyr Val Thr
225                 230                 235                 240
Gly Ile Thr Leu Phe Ala Asp Gly Gly Met Thr Gln Tyr Pro Ser Phe
                245                 250                 255
Gln Ala Gly Arg Gly
            260

<210> SEQ ID NO 11
<211> LENGTH: 786
<212> TYPE: DNA
<213> ORGANISM: Bacillus Sp.
<220> FEATURE:
<221> NAME/KEY: CDS
<222> LOCATION: (1)...(786)
<223> OTHER INFORMATION: Glucose dehydrogenase M02-6

<400> SEQUENCE: 11 atg tat aaa gat tta gaa gga aaa gta gtt gtc ata aca ggt tca tct     48
Met Tyr Lys Asp Leu Glu Gly Lys Val Val Val Ile Thr Gly Ser Ser
 1               5                  10                  15 acc ggt tta gga aaa gca atg gcg att cgt ttt gcg aca gaa aaa gct     96
Thr Gly Leu Gly Lys Ala Met Ala Ile Arg Phe Ala Thr Glu Lys Ala
            20                  25                  30 aaa gta gtt gtg aat tat cgt tcg aaa gaa gaa gaa gct aac agc gtt    144
Lys Val Val Val Asn Tyr Arg Ser Lys Glu Glu Glu Ala Asn Ser Val
        35                  40                  45 tta gaa gaa att aaa aaa gtc ggc gga gag gca att gcg gtt aaa ggt    192
Leu Glu Glu Ile Lys Lys Val Gly Gly Glu Ala Ile Ala Val Lys Gly
    50                  55                  60 gac gta aca gtt gag tct gac gtg atc aat tta gtt caa tct gct att    240
Asp Val Thr Val Glu Ser Asp Val Ile Asn Leu Val Gln Ser Ala Ile
65                  70                  75                  80 aaa gaa ttt gga aag tta gat gtt atg att aat aac gca gga atg gaa    288
Lys Glu Phe Gly Lys Leu Asp Val Met Ile Asn Asn Ala Gly Met Glu
                85                  90                  95 aat ccg gtt tca tct cat gaa atg tct tta agc gat tgg aat aaa gta    336
Asn Pro Val Ser Ser His Glu Met Ser Leu Ser Asp Trp Asn Lys Val
                100                 105                 110 att gat acg aac tta acg gga gca ttt tta gga agc cgt gaa gcg att    384
Ile Asp Thr Asn Leu Thr Gly Ala Phe Leu Gly Ser Arg Glu Ala Ile
            115                 120                 125
```

-continued

```
aaa tat ttc gtg gaa aat gat att aag gga aca gtt att aat atg tcg       432
Lys Tyr Phe Val Glu Asn Asp Ile Lys Gly Thr Val Ile Asn Met Ser
    130                 135                 140 agt gtt cat gag aaa att cct tgg cca tta ttt gtt cat tac gca gca       480
Ser Val His Glu Lys Ile Pro Trp Pro Leu Phe Val His Tyr Ala Ala
145                 150                 155                 160 agt aaa ggt ggc atg aag ctc atg act gaa aca ctt gca tta gaa tat       528
Ser Lys Gly Gly Met Lys Leu Met Thr Glu Thr Leu Ala Leu Glu Tyr
                165                 170                 175 gct cca aaa ggt att cgt gta aat aac att ggg ccg gga gcg att aat       576
Ala Pro Lys Gly Ile Arg Val Asn Asn Ile Gly Pro Gly Ala Ile Asn
            180                 185                 190 aca ccg att aac gct gag aaa ttt gct gat cct aag cag cgc gca gat       624
Thr Pro Ile Asn Ala Glu Lys Phe Ala Asp Pro Lys Gln Arg Ala Asp
        195                 200                 205 gta gaa agc atg att cca atg gga tac atc gga gag ccg gaa gaa att       672
Val Glu Ser Met Ile Pro Met Gly Tyr Ile Gly Glu Pro Glu Glu Ile
    210                 215                 220 gca gcg gtt gct gca tgg cta gct tct tca gaa gca agt tat gta aca       720
Ala Ala Val Ala Ala Trp Leu Ala Ser Ser Glu Ala Ser Tyr Val Thr
225                 230                 235                 240 ggg att acg ctc ttt gct gac ggc ggt atg aca cag tac cca tca ttc       768
Gly Ile Thr Leu Phe Ala Asp Gly Gly Met Thr Gln Tyr Pro Ser Phe
                245                 250                 255 caa gca gga cgc gga taa                                               786
Gln Ala Gly Arg Gly *
            260
```

<210> SEQ ID NO 12
<211> LENGTH: 261
<212> TYPE: PRT
<213> ORGANISM: Bacillus Sp.

<400> SEQUENCE: 12

```
Met Tyr Lys Asp Leu Glu Gly Lys Val Val Ile Thr Gly Ser Ser
 1               5                  10                  15

Thr Gly Leu Gly Lys Ala Met Ala Ile Arg Phe Ala Thr Glu Lys Ala
                20                  25                  30

Lys Val Val Asn Tyr Arg Ser Lys Glu Glu Ala Asn Ser Val
         35                  40                  45

Leu Glu Glu Ile Lys Lys Val Gly Gly Glu Ala Ile Ala Val Lys Gly
    50                  55                  60

Asp Val Thr Val Glu Ser Asp Val Ile Asn Leu Val Gln Ser Ala Ile
65                  70                  75                  80

Lys Glu Phe Gly Lys Leu Asp Val Met Ile Asn Asn Ala Gly Met Glu
                85                  90                  95

Asn Pro Val Ser Ser His Glu Met Ser Leu Ser Asp Trp Asn Lys Val
            100                 105                 110

Ile Asp Thr Asn Leu Thr Gly Ala Phe Leu Gly Ser Arg Glu Ala Ile
        115                 120                 125

Lys Tyr Phe Val Glu Asn Asp Ile Lys Gly Thr Val Ile Asn Met Ser
    130                 135                 140

Ser Val His Glu Lys Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190
```

Thr Pro Ile Asn Ala Glu Lys Phe Ala Asp Pro Lys Gln Arg Ala Asp
            195                 200                 205

Val Glu Ser Met Ile Pro Met Gly Tyr Ile Gly Glu Pro Glu Glu Ile
            210                 215                 220

Ala Ala Val Ala Ala Trp Leu Ala Ser Ser Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 13
<211> LENGTH: 765
<212> TYPE: DNA
<213> ORGANISM: Artificial Sequence
<220> FEATURE:
<221> NAME/KEY: CDS
<222> LOCATION: (1)...(765)
<223> OTHER INFORMATION: HHDH.1
<220> FEATURE:
<223> OTHER INFORMATION: HHDH.1

<400> SEQUENCE: 13

```
atg agc acc gct atc gtc acc aac gtc aaa cat ttt ggt ggt atg ggt        48
Met Ser Thr Ala Ile Val Thr Asn Val Lys His Phe Gly Gly Met Gly
 1               5                  10                  15 agc gct ctg agg ctg agc gaa gct ggt cat acc gtc gct tgc cat gat        96
Ser Ala Leu Arg Leu Ser Glu Ala Gly His Thr Val Ala Cys His Asp
                20                  25                  30 gaa agc ttt aaa cag aaa gat gaa ctg gaa gct ttt gct gaa acc tac       144
Glu Ser Phe Lys Gln Lys Asp Glu Leu Glu Ala Phe Ala Glu Thr Tyr
            35                  40                  45 cca cag ctg aaa cca atg agc gaa cag gaa cca gct gaa ctg atc gaa       192
Pro Gln Leu Lys Pro Met Ser Glu Gln Glu Pro Ala Glu Leu Ile Glu
     50                  55                  60 gct gtc acc agc gct tac ggt cag gtc gat gtc ctg gtc agc aac gat       240
Ala Val Thr Ser Ala Tyr Gly Gln Val Asp Val Leu Val Ser Asn Asp
 65                  70                  75                  80 atc ttt gct cca gaa ttt cag cca atc gat aaa tac gct gtc gaa gat       288
Ile Phe Ala Pro Glu Phe Gln Pro Ile Asp Lys Tyr Ala Val Glu Asp
                 85                  90                  95 tac agg ggt gct gtc gaa gct ctg cag atc agg cca ttt gct cta gtg       336
Tyr Arg Gly Ala Val Glu Ala Leu Gln Ile Arg Pro Phe Ala Leu Val
                100                 105                 110 aat gct gtg gct tcg caa atg aag aag cga aag tcg ggg cac atc atc       384
Asn Ala Val Ala Ser Gln Met Lys Lys Arg Lys Ser Gly His Ile Ile
            115                 120                 125 ttc atc act tcg gct act ccg ttc ggg ccg tgg aag gag cta tcg act       432
Phe Ile Thr Ser Ala Thr Pro Phe Gly Pro Trp Lys Glu Leu Ser Thr
        130                 135                 140 tac act tcg gct cga gct ggg gct tgt act cta gct aat gct cta tcg       480
Tyr Thr Ser Ala Arg Ala Gly Ala Cys Thr Leu Ala Asn Ala Leu Ser
145                 150                 155                 160 aag gag cta ggg gag tac aat atc ccg gtg ttc gct atc ggg ccg aat       528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg       576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta       624
Lys Thr Asn Pro Glu His Val Ala His Val Lys Lys Val Thr Ala Leu
```

```
                                                          672
caa cga cta ggg act caa aaa gag ttg ggg gaa ttg gtg gca ttt ttg
Gln Arg Leu Gly Thr Gln Lys Glu Leu Gly Glu Leu Val Ala Phe Leu
    210                 215                 220

720
gca tct ggc tct tgt gat tat ttg act ggc cag gtg ttt tgg ttg gca
Ala Ser Gly Ser Cys Asp Tyr Leu Thr Gly Gln Val Phe Trp Leu Ala
225                 230                 235                 240

765
ggc ggc ttt ccc atg ata gaa cgt tgg ccc ggc atg ccc gaa taa
Gly Gly Phe Pro Met Ile Glu Arg Trp Pro Gly Met Pro Glu  *
                245                 250
```

<210> SEQ ID NO 14
<211> LENGTH: 254
<212> TYPE: PRT
<213> ORGANISM: Agrobacterium sp.

<400> SEQUENCE: 14

```
Met Ser Thr Ala Ile Val Thr Asn Val Lys His Phe Gly Gly Met Gly
  1               5                  10                  15

Ser Ala Leu Arg Leu Ser Glu Ala Gly His Thr Val Ala Cys His Asp
             20                  25                  30

Glu Ser Phe Lys Gln Lys Asp Glu Leu Glu Ala Phe Ala Glu Thr Tyr
         35                  40                  45

Pro Gln Leu Lys Pro Met Ser Glu Gln Glu Pro Ala Glu Leu Ile Glu
     50                  55                  60

Ala Val Thr Ser Ala Tyr Gly Gln Val Asp Val Leu Val Ser Asn Asp
 65                  70                  75                  80

Ile Phe Ala Pro Glu Phe Gln Pro Ile Asp Lys Tyr Ala Val Glu Asp
                 85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
    130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250
```

<210> SEQ ID NO 15
<211> LENGTH: 765
<212> TYPE: DNA
<213> ORGANISM: Artificial Sequence
<220> FEATURE:
<221> NAME/KEY: CDS
<222> LOCATION: (1)...(765)

<223> OTHER INFORMATION: HHDH.2
<220> FEATURE:
<223> OTHER INFORMATION: HHDH.2

<400> SEQUENCE: 15

```
atg agc acc gct atc gtc acc aac gtc aaa cat ttt ggt ggt atg ggt       48
Met Ser Thr Ala Ile Val Thr Asn Val Lys His Phe Gly Gly Met Gly
 1               5                  10                  15 agc gct ctg agg ctg agc gaa gct ggt cat acc gtc gct tgc cat gat       96
Ser Ala Leu Arg Leu Ser Glu Ala Gly His Thr Val Ala Cys His Asp
                20                  25                  30 gaa agc ttt aaa cag aaa gat gaa ctg gaa gct ttt gct gaa acc tac      144
Glu Ser Phe Lys Gln Lys Asp Glu Leu Glu Ala Phe Ala Glu Thr Tyr
            35                  40                  45 cca cag ctg aaa cca atg agc gaa cag gaa cca gct gaa ctg atc gaa      192
Pro Gln Leu Lys Pro Met Ser Glu Gln Glu Pro Ala Glu Leu Ile Glu
        50                  55                  60 gct gtc acc agc gct tac ggt caa gtc gat gtc ctg gtc agc aac gat      240
Ala Val Thr Ser Ala Tyr Gly Gln Val Asp Val Leu Val Ser Asn Asp
 65                  70                  75                  80 atc ttt gct cca gaa ttt cag cca atc gat aaa tac gct gtc gaa gat      288
Ile Phe Ala Pro Glu Phe Gln Pro Ile Asp Lys Tyr Ala Val Glu Asp
                85                  90                  95 tac agg ggt gct gtc gaa gct ctg cag atc agg cca ttt gct cta gtg      336
Tyr Arg Gly Ala Val Glu Ala Leu Gln Ile Arg Pro Phe Ala Leu Val
               100                 105                 110 aat gct gtg gct tcg caa atg aag aag cga aag tcg ggg cac atc atc      384
Asn Ala Val Ala Ser Gln Met Lys Lys Arg Lys Ser Gly His Ile Ile
            115                 120                 125 ttc atc act tcg gct act ccg ttc ggg ccg tgg aag gag cta tcg act      432
Phe Ile Thr Ser Ala Thr Pro Phe Gly Pro Trp Lys Glu Leu Ser Thr
        130                 135                 140 tac act tcg gct cga gct ggg gct tgt act cta gct aat gct cta tcg      480
Tyr Thr Ser Ala Arg Ala Gly Ala Cys Thr Leu Ala Asn Ala Leu Ser
145                 150                 155                 160 aag gag cta ggg gag tac aat atc ccg gtg ttc gct atc ggg ccg aat      528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg      576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta      624
Lys Thr Asn Pro Glu His Val Ala His Val Lys Lys Val Thr Ala Leu
        195                 200                 205 caa cga tta ggg act caa aaa gag ttg ggg gaa ttg gtg gca ttt ttg      672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca      720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa          765
Gly Gly Phe Pro Met Ile Glu Arg Trp Pro Gly Met Pro Glu *
                245                 250
```

<210> SEQ ID NO 16
<211> LENGTH: 254
<212> TYPE: PRT
<213> ORGANISM: Agrobacterium sp.

<400> SEQUENCE: 16

Met Ser Thr Ala Ile Val Thr Asn Val Lys His Phe Gly Gly Met Gly

```
            1               5                   10                  15
          Ser Ala Leu Arg Leu Ser Glu Ala Gly His Thr Val Ala Cys His Asp
                        20                  25                  30

Glu Ser Phe Lys Gln Lys Asp Glu Leu Glu Ala Phe Ala Glu Thr Tyr
                        35                  40                  45

Pro Gln Leu Lys Pro Met Ser Glu Gln Glu Pro Ala Glu Leu Ile Glu
                        50                  55                  60

Ala Val Thr Ser Ala Tyr Gly Gln Val Asp Val Leu Val Ser Asn Asp
           65                  70                  75                  80

Ile Phe Ala Pro Glu Phe Gln Pro Ile Asp Lys Tyr Ala Val Glu Asp
                        85                  90                  95

Tyr Arg Gly Ala Val Glu Ala Leu Gln Ile Arg Pro Phe Ala Leu Val
                        100                 105                 110

Asn Ala Val Ala Ser Gln Met Lys Lys Arg Lys Ser Gly His Ile Ile
                        115                 120                 125

Phe Ile Thr Ser Ala Thr Pro Phe Gly Pro Trp Lys Glu Leu Ser Thr
                        130                 135                 140

Tyr Thr Ser Ala Arg Ala Gly Ala Cys Thr Leu Ala Asn Ala Leu Ser
          145                 150                 155                 160

Lys Glu Leu Gly Glu Tyr Asn Ile Pro Val Phe Ala Ile Gly Pro Asn
                        165                 170                 175

Tyr Leu His Ser Glu Asp Ser Pro Tyr Phe Tyr Pro Thr Glu Pro Trp
                        180                 185                 190

Lys Thr Asn Pro Glu His Val Ala His Val Lys Lys Val Thr Ala Leu
                        195                 200                 205

Gln Arg Leu Gly Thr Gln Lys Glu Leu Gly Glu Leu Val Ala Phe Leu
                        210                 215                 220

Ala Ser Gly Ser Cys Asp Tyr Leu Thr Gly Gln Val Phe Trp Leu Ala
          225                 230                 235                 240

Gly Gly Phe Pro Met Ile Glu Arg Trp Pro Gly Met Pro Glu
                        245                 250
```

<210> SEQ ID NO 17
<211> LENGTH: 765
<212> TYPE: DNA
<213> ORGANISM: Artificial Sequence
<220> FEATURE:
<221> NAME/KEY: CDS
<222> LOCATION: (1)...(765)
<223> OTHER INFORMATION: HHDH.16
<220> FEATURE:
<223> OTHER INFORMATION: HHDH.16

<400> SEQUENCE: 17

```
atg agc acc gct atc gtc acc aac gtc aaa cat ttt ggt ggt atg ggt      48
Met Ser Thr Ala Ile Val Thr Asn Val Lys His Phe Gly Gly Met Gly
 1               5                  10                  15 agc gct ctg agg ctg agc gaa gct ggt cat acc gtc gct tgc cat gat      96
Ser Ala Leu Arg Leu Ser Glu Ala Gly His Thr Val Ala Cys His Asp
                20                  25                  30 gaa agc ttt aaa cag aaa gat gaa ctg gaa gct ttt gct gaa acc tac     144
Glu Ser Phe Lys Gln Lys Asp Glu Leu Glu Ala Phe Ala Glu Thr Tyr
            35                  40                  45 cca cag ctg aaa cca atg agc gaa cag gaa cca gct gaa ctg atc gaa     192
Pro Gln Leu Lys Pro Met Ser Glu Gln Glu Pro Ala Glu Leu Ile Glu
        50                  55                  60 gct gtc acc agc gct tac ggt cag gtc gat gtc ctg gtc agc aac gat     240
Ala Val Thr Ser Ala Tyr Gly Gln Val Asp Val Leu Val Ser Asn Asp
```

```
                 65                  70                  75                  80
atc ttt gct cca gaa ttt cag cca atc gat aaa tac gct gtc gaa gat         288
Ile Phe Ala Pro Glu Phe Gln Pro Ile Asp Lys Tyr Ala Val Glu Asp
                     85                  90                  95 tac agg ggt gct gtc gaa gct ctg cag atc agg cca ttt gct cta gtg         336
Tyr Arg Gly Ala Val Glu Ala Leu Gln Ile Arg Pro Phe Ala Leu Val
                100                 105                 110 aat gct gtg gct tcg caa atg aag aag cga aag tcg ggg cac atc atc         384
Asn Ala Val Ala Ser Gln Met Lys Lys Arg Lys Ser Gly His Ile Ile
            115                 120                 125 ttc atc act tcg gct act ccg ttc ggg ccg tgg aag gag cta tcg act         432
Phe Ile Thr Ser Ala Thr Pro Phe Gly Pro Trp Lys Glu Leu Ser Thr
        130                 135                 140 tac act tcg gct cga gct ggg gct tgt act cta gct aat gct cta tcg         480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat         528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg         576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta         624
Lys Thr Asn Pro Glu His Val Ala His Val Lys Lys Val Thr Ala Leu
        195                 200                 205 caa cga cta ggg act caa aaa gag ttg ggg gaa ttg gtg gca ttt ttg         672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca         720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa             765
Gly Gly Phe Pro Met Ile Glu Arg Trp Pro Gly Met Pro Glu *
                245                 250

<210> SEQ ID NO 18
<211> LENGTH: 254
<212> TYPE: PRT
<213> ORGANISM: Agrobacterium sp.

<400> SEQUENCE: 18

Met Ser Thr Ala Ile Val Thr Asn Val Lys His Phe Gly Gly Met Gly
  1               5                  10                  15

Ser Ala Leu Arg Leu Ser Glu Ala Gly His Thr Val Ala Cys His Asp
                 20                  25                  30

Glu Ser Phe Lys Gln Lys Asp Glu Leu Glu Ala Phe Ala Glu Thr Tyr
             35                  40                  45

Pro Gln Leu Lys Pro Met Ser Glu Gln Glu Pro Ala Glu Leu Ile Glu
         50                  55                  60

Ala Val Thr Ser Ala Tyr Gly Gln Val Asp Val Leu Val Ser Asn Asp
 65                  70                  75                  80

Ile Phe Ala Pro Glu Phe Gln Pro Ile Asp Lys Tyr Ala Val Glu Asp
                 85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
```

-continued

```
            130                 135                 140
Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Val Thr Ala Leu
            195                 200                 205

Gln Arg Leu Gly Thr Gln Lys Glu Leu Gly Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250
```

<210> SEQ ID NO 19
<211> LENGTH: 32
<212> TYPE: DNA
<213> ORGANISM: Artificial Sequence
<220> FEATURE:
<223> OTHER INFORMATION: Synthetic primer

<400> SEQUENCE: 19
gaattcgccc atatgtatcc ggatttaaaa gg                                32

<210> SEQ ID NO 20
<211> LENGTH: 34
<212> TYPE: DNA
<213> ORGANISM: Artificial Sequence
<220> FEATURE:
<223> OTHER INFORMATION: Synthetic primer

<400> SEQUENCE: 20
tggccggatc ctcattaacc gcggcctgcc tgga                              34

<210> SEQ ID NO 21
<211> LENGTH: 32
<212> TYPE: DNA
<213> ORGANISM: Artificial Sequence
<220> FEATURE:
<223> OTHER INFORMATION: Synthetic primer

<400> SEQUENCE: 21
gaattcgccc atatgtataa agatttagaa gg                                32

<210> SEQ ID NO 22
<211> LENGTH: 33
<212> TYPE: DNA
<213> ORGANISM: Artificial Sequence
<220> FEATURE:
<223> OTHER INFORMATION: Synthetic primer

<400> SEQUENCE: 22
ggccggatcc tcattatccg cgtcctgctt gga                               33

<210> SEQ ID NO 23
<211> LENGTH: 765
<212> TYPE: DNA
<213> ORGANISM: Artificial Sequence
<220> FEATURE:
<223> OTHER INFORMATION: HHDH P016013-B-03
<220> FEATURE:

```
<221> NAME/KEY: CDS
<222> LOCATION: (1)...(765)

<400> SEQUENCE: 23 atg agc acc gct atc gtc acc aac gtc aaa cat ttt gga ggt atg ggt      48
Met Ser Thr Ala Ile Val Thr Asn Val Lys His Phe Gly Gly Met Gly
 1               5                  10                  15 agc gct ctg agg ctg agc gaa gct ggt cat acc gtc gct tgc cat gat      96
Ser Ala Leu Arg Leu Ser Glu Ala Gly His Thr Val Ala Cys His Asp
             20                  25                  30 gaa agc ttt aaa cag aaa gat gaa ctg gaa gct ttt gct gaa acc tac     144
Glu Ser Phe Lys Gln Lys Asp Glu Leu Glu Ala Phe Ala Glu Thr Tyr
         35                  40                  45 cca cag ctg aaa cca atg agc gaa cag gaa cca gct gaa ctg atc gaa     192
Pro Gln Leu Lys Pro Met Ser Glu Gln Glu Pro Ala Glu Leu Ile Glu
     50                  55                  60 gct gtc acc agc gct tac ggt cag gtc gat gtc ctg gtc agc aac gat     240
Ala Val Thr Ser Ala Tyr Gly Gln Val Asp Val Leu Val Ser Asn Asp
 65                  70                  75                  80 atc ttt gct cca gaa ttt cag cca atc gat aaa tac gct gtc gaa gat     288
Ile Phe Ala Pro Glu Phe Gln Pro Ile Asp Lys Tyr Ala Val Glu Asp
                 85                  90                  95 tac agg ggt gct gtc gaa gct ctg cag atc agg cca ttt gct cta gtg     336
Tyr Arg Gly Ala Val Glu Ala Leu Gln Ile Arg Pro Phe Ala Leu Val
            100                 105                 110 aat gct gtg gct tcg caa atg aag aag cga aag tcg ggg cac atc atc     384
Asn Ala Val Ala Ser Gln Met Lys Lys Arg Lys Ser Gly His Ile Ile
        115                 120                 125 ttc atc act tcg gct gct ccg ttc ggg cca tgg aaa gag cta tcg act     432
Phe Ile Thr Ser Ala Ala Pro Phe Gly Pro Trp Lys Glu Leu Ser Thr
    130                 135                 140 tac act tcg gct cga gct ggg gct tgt act cta gct aat gct cta tcg     480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat     528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg     576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta     624
Lys Thr Asn Pro Glu His Val Ala His Val Lys Lys Val Thr Ala Leu
        195                 200                 205 caa cga cta ggg act caa aaa gag ttg ggg gaa ttg gtg gca ttc ttg     672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca     720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa         765
Gly Gly Phe Pro Met Ile Glu Arg Trp Pro Gly Met Pro Glu  *
                245                 250

<210> SEQ ID NO 24
<211> LENGTH: 254
<212> TYPE: PRT
<213> ORGANISM: Artificial Sequence
<220> FEATURE:
<223> OTHER INFORMATION: HHDH P016013-B-03

<400> SEQUENCE: 24
```

```
Met Ser Thr Ala Ile Val Thr Asn Val Lys His Phe Gly Gly Met Gly
 1               5                  10                  15

Ser Ala Leu Arg Leu Ser Glu Ala Gly His Thr Val Ala Cys His Asp
             20                  25                  30

Glu Ser Phe Lys Gln Lys Asp Glu Leu Glu Ala Phe Ala Glu Thr Tyr
             35                  40                  45

Pro Gln Leu Lys Pro Met Ser Glu Gln Glu Pro Ala Glu Leu Ile Glu
 50                  55                  60

Ala Val Thr Ser Ala Tyr Gly Gln Val Asp Val Leu Val Ser Asn Asp
 65                  70                  75                  80

Ile Phe Ala Pro Glu Phe Gln Pro Ile Asp Lys Tyr Ala Val Glu Asp
             85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
            115                 120                 125

Phe Ile Thr Ser Ala Ala Pro Phe Gly Pro Trp Lys Glu Leu Ser Thr
130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
            165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
            195                 200                 205

Gln Arg Leu Gly Thr Gln Lys Glu Leu Gly Glu Leu Val Ala Phe Leu
            210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
            245                 250
```

<210> SEQ ID NO 25
<211> LENGTH: 765
<212> TYPE: DNA
<213> ORGANISM: Artificial Sequence
<220> FEATURE:
<223> OTHER INFORMATION: HHDH P016015-C-04
<220> FEATURE:
<221> NAME/KEY: CDS
<222> LOCATION: (1)...(765)

<400> SEQUENCE: 25

```
atg agc acc gct atc gtc acc aac gtc aaa cat ttt gga ggt atg ggt      48
Met Ser Thr Ala Ile Val Thr Asn Val Lys His Phe Gly Gly Met Gly
 1               5                  10                  15 agc gct ctg agg ctg agc gaa gct ggt cat acc gtc gct tgc cat gat      96
Ser Ala Leu Arg Leu Ser Glu Ala Gly His Thr Val Ala Cys His Asp
             20                  25                  30 gaa agc ttt aaa cag aaa gat gaa ctg gaa gct ttt gct gaa acc tac     144
Glu Ser Phe Lys Gln Lys Asp Glu Leu Glu Ala Phe Ala Glu Thr Tyr
             35                  40                  45 cca cag ctg aaa cca atg agc gaa cag gaa cca gct gaa ctg atc gaa     192
Pro Gln Leu Lys Pro Met Ser Glu Gln Glu Pro Ala Glu Leu Ile Glu
 50                  55                  60 gct gtc acc agc gct tac ggt cag gtc gat gtc ctg gtc agc aac gat     240
Ala Val Thr Ser Ala Tyr Gly Gln Val Asp Val Leu Val Ser Asn Asp
```

```
atc ttt gct cca gaa ttt cag cca atc gat aaa tac gct gtc cag gat      288
Ile Phe Ala Pro Glu Phe Gln Pro Ile Asp Lys Tyr Ala Val Gln Asp
                85                  90                  95 tac agg ggt gct gtc gaa gct ctg cag atc agg cca ttt gct ctg gcg      336
Tyr Arg Gly Ala Val Glu Ala Leu Gln Ile Arg Pro Phe Ala Leu Ala
            100                 105                 110 aat gct gtg gct tcg caa atg aag aag cga aag tcg ggg cac atc atc      384
Asn Ala Val Ala Ser Gln Met Lys Lys Arg Lys Ser Gly His Ile Ile
        115                 120                 125 ttc atc act tcg gct gct ccg ttc ggg cca tgg aag gag cta tcg act      432
Phe Ile Thr Ser Ala Ala Pro Phe Gly Pro Trp Lys Glu Leu Ser Thr
    130                 135                 140 tac act tcg gct cga gct ggg gct tgt act cta gct aat gct cta tcg      480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat      528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg      576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta      624
Lys Thr Asn Pro Glu His Val Ala His Val Lys Lys Val Thr Ala Leu
        195                 200                 205 caa cga cta ggg act caa aaa gag ttg ggg gaa ttg gtg gca ttt ttg      672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca      720
Ala Ser Gly Ser Cys Asp Tyr Leu Thr Gly Gln Val Phe Trp Leu Ala
225                 230                 235                 240 ggc ggt ttt ccc atg ata gaa cgt tgg ccc ggc atg ccc gaa taa           765
Gly Gly Phe Pro Met Ile Glu Arg Trp Pro Gly Met Pro Glu *
                245                 250
```

<210> SEQ ID NO 26
<211> LENGTH: 254
<212> TYPE: PRT
<213> ORGANISM: Artificial Sequence
<220> FEATURE:
<223> OTHER INFORMATION: HHDH P016015-C-04

<400> SEQUENCE: 26

```
Met Ser Thr Ala Ile Val Thr Asn Val Lys His Phe Gly Gly Met Gly
 1               5                  10                  15

Ser Ala Leu Arg Leu Ser Glu Ala Gly His Thr Val Ala Cys His Asp
            20                  25                  30

Glu Ser Phe Lys Gln Lys Asp Glu Leu Glu Ala Phe Ala Glu Thr Tyr
        35                  40                  45

Pro Gln Leu Lys Pro Met Ser Glu Gln Glu Pro Ala Glu Leu Ile Glu
    50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Gln Asp
                85                  90                  95

Tyr Arg Gly Ala Val Glu Ala Leu Gln Ile Arg Pro Phe Ala Leu Ala
            100                 105                 110

Asn Ala Val Ala Ser Gln Met Lys Lys Arg Lys Ser Gly His Ile Ile
        115                 120                 125
```

```
Phe Ile Thr Ser Ala Ala Pro Phe Gly Pro Trp Lys Glu Leu Ser Thr
        130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250

<210> SEQ ID NO 27
<211> LENGTH: 765
<212> TYPE: DNA
<213> ORGANISM: Artificial Sequence
<220> FEATURE:
<223> OTHER INFORMATION: HHDH P016014-E-01
<220> FEATURE:
<221> NAME/KEY: CDS
<222> LOCATION: (1)...(765)

<400> SEQUENCE: 27 atg agc acc gct atc gtc acc aac gtc aaa cat ttt gga ggt atg ggt      48
Met Ser Thr Ala Ile Val Thr Asn Val Lys His Phe Gly Gly Met Gly
  1               5                  10                  15 agc gct ctg agg ctg agc gaa gct ggt cat acc gtc gct tgc cat gat      96
Ser Ala Leu Arg Leu Ser Glu Ala Gly His Thr Val Ala Cys His Asp
                 20                  25                  30 gaa agc ttt aaa cag aaa gat gaa ctg gaa gct ttt gct gaa acc tac     144
Glu Ser Phe Lys Gln Lys Asp Glu Leu Glu Ala Phe Ala Glu Thr Tyr
             35                  40                  45 cca cag ctg aaa cca atg agc gaa cag gaa cca gct gac ctg att gaa     192
Pro Gln Leu Lys Pro Met Ser Glu Gln Glu Pro Ala Asp Leu Ile Glu
         50                  55                  60 gct gtc acc agc gct tac ggt cag gtc gat gtc ctg gtc agc aac gat     240
Ala Val Thr Ser Ala Tyr Gly Gln Val Asp Val Leu Val Ser Asn Asp
 65                  70                  75                  80 atc ttt gct cca gaa ttt cag cca atc gat aaa tac gct gtc gaa gac     288
Ile Phe Ala Pro Glu Phe Gln Pro Ile Asp Lys Tyr Ala Val Glu Asp
                 85                  90                  95 tac agg ggt gct gtc gaa gct ctg cag atc agg cca ttt gct cta gtg     336
Tyr Arg Gly Ala Val Glu Ala Leu Gln Ile Arg Pro Phe Ala Leu Val
            100                 105                 110 aat gct gtg gct tcg caa atg aag aaa cga aag tcg ggg cac atc atc     384
Asn Ala Val Ala Ser Gln Met Lys Lys Arg Lys Ser Gly His Ile Ile
        115                 120                 125 ttc atc act tcg gct act ccg ttc ggg cca tgg aaa gag cta tcg act     432
Phe Ile Thr Ser Ala Thr Pro Phe Gly Pro Trp Lys Glu Leu Ser Thr
    130                 135                 140 tac act tcg gct cga gct ggg gct tgt act cta gct aat gct cta tcg     480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat     528
```

```
Lys Glu Leu Gly Glu Tyr Asn Ile Pro Val Phe Ala Ile Gly Pro Asn
            165                 170                 175 tac cta cac tcg gag gat tcg ccg tac ttc tac ccg act gag ccg tgg      576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta      624
Lys Thr Asn Pro Glu His Val Ala His Val Lys Lys Val Thr Ala Leu
            195                 200                 205 caa cga cta ggg act caa aaa gag ttg ggg gaa ttg gtg gca ttc ctg      672
Gln Arg Leu Gly Thr Gln Lys Glu Leu Gly Glu Leu Val Ala Phe Leu
            210                 215                 220 gca tct ggc tct tgt gat tat ttg act ggc cag gtg ttt tgg ttg gca      720
Ala Ser Gly Ser Cys Asp Tyr Leu Thr Gly Gln Val Phe Trp Leu Ala
225                 230                 235                 240 ggc ggc ttt ccc att ata gaa cgt tgg ccc ggc atg ccc gaa taa          765
Gly Gly Phe Pro Ile Ile Glu Arg Trp Pro Gly Met Pro Glu *
            245                 250

<210> SEQ ID NO 28
<211> LENGTH: 254
<212> TYPE: PRT
<213> ORGANISM: Artificial Sequence
<220> FEATURE:
<223> OTHER INFORMATION: HHDH P016014-E-01

<400> SEQUENCE: 28

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys Gln Lys Asp Glu Leu Glu Ala Phe Ala Glu Thr Tyr
        35                  40                  45

Pro Gln Leu Lys Pro Met Ser Glu Gln Glu Pro Ala Asp Leu Ile Glu
    50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Glu Asp
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
    130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Ile Ile Glu Arg Trp Pro Gly Met Pro Glu
```

<210> SEQ ID NO 29
<211> LENGTH: 765
<212> TYPE: DNA
<213> ORGANISM: Artificial Sequence
<220> FEATURE:
<223> OTHER INFORMATION: HHDH P016014-G-08
<220> FEATURE:
<221> NAME/KEY: CDS
<222> LOCATION: (1)...(765)

<400> SEQUENCE: 29

| | | | | | | | | | | | | | | | | |
|---|---|---|---|---|---|---|---|---|---|---|---|---|---|---|---|---|
| atg | agc | acc | gct | atc | gtc | acc | aac | ttc | aaa | cat | ttt | gga | ggt | atg | ggt | 48 |
| Met | Ser | Thr | Ala | Ile | Val | Thr | Asn | Phe | Lys | His | Phe | Gly | Gly | Met | Gly | |
| 1 | | | | 5 | | | | | 10 | | | | | 15 | | |
| agc | gct | ctg | agg | ctg | agc | gaa | gct | ggt | cat | acc | gtc | gct | tgc | cat | gat | 96 |
| Ser | Ala | Leu | Arg | Leu | Ser | Glu | Ala | Gly | His | Thr | Val | Ala | Cys | His | Asp | |
| | | | 20 | | | | | 25 | | | | | 30 | | | |
| gaa | agc | ttt | aaa | cag | aaa | gat | gaa | ctg | gaa | gct | ttt | gct | gaa | acc | tac | 144 |
| Glu | Ser | Phe | Lys | Gln | Lys | Asp | Glu | Leu | Glu | Ala | Phe | Ala | Glu | Thr | Tyr | |
| | 35 | | | | | 40 | | | | | 45 | | | | | |
| cca | cag | ctg | aaa | cca | atg | agc | gaa | cag | gaa | cca | gct | gac | ctg | att | gaa | 192 |
| Pro | Gln | Leu | Lys | Pro | Met | Ser | Glu | Gln | Glu | Pro | Ala | Asp | Leu | Ile | Glu | |
| 50 | | | | | 55 | | | | | 60 | | | | | | |
| gct | gtc | acc | agc | gct | tac | ggt | cag | gtc | gat | gtc | ctg | gtc | agc | aac | gat | 240 |
| Ala | Val | Thr | Ser | Ala | Tyr | Gly | Gln | Val | Asp | Val | Leu | Val | Ser | Asn | Asp | |
| 65 | | | | | 70 | | | | | 75 | | | | | 80 | |
| atc | ttt | gct | cca | gaa | ttt | cag | cca | atc | gat | aaa | tac | gct | gtc | gaa | aac | 288 |
| Ile | Phe | Ala | Pro | Glu | Phe | Gln | Pro | Ile | Asp | Lys | Tyr | Ala | Val | Glu | Asn | |
| | | | | 85 | | | | | 90 | | | | | 95 | | |
| tac | agg | ggt | gct | gtc | gaa | gct | ctg | cag | atc | agg | cca | ttt | gct | cta | gtg | 336 |
| Tyr | Arg | Gly | Ala | Val | Glu | Ala | Leu | Gln | Ile | Arg | Pro | Phe | Ala | Leu | Val | |
| | | | 100 | | | | | 105 | | | | | 110 | | | |
| aat | gct | gtg | gct | tcg | caa | atg | aag | aaa | cga | aag | tcg | ggg | cac | atc | atc | 384 |
| Asn | Ala | Val | Ala | Ser | Gln | Met | Lys | Lys | Arg | Lys | Ser | Gly | His | Ile | Ile | |
| | | 115 | | | | | 120 | | | | | 125 | | | | |
| ttc | atc | act | tcg | tct | act | ccg | ttc | ggg | cca | tgg | aaa | gag | cta | tcg | act | 432 |
| Phe | Ile | Thr | Ser | Ser | Thr | Pro | Phe | Gly | Pro | Trp | Lys | Glu | Leu | Ser | Thr | |
| 130 | | | | | 135 | | | | | 140 | | | | | | |
| tac | act | tcg | gct | cga | gct | ggg | gct | tgt | act | cta | gct | aat | gct | cta | tcg | 480 |
| Tyr | Thr | Ser | Ala | Arg | Ala | Gly | Ala | Cys | Thr | Leu | Ala | Asn | Ala | Leu | Ser | |
| 145 | | | | | 150 | | | | | 155 | | | | | 160 | |
| aag | gag | cta | gga | gag | tac | aat | atc | ccg | gtg | ttc | gct | atc | ggg | ccg | aat | 528 |
| Lys | Glu | Leu | Gly | Glu | Tyr | Asn | Ile | Pro | Val | Phe | Ala | Ile | Gly | Pro | Asn | |
| | | | | 165 | | | | | 170 | | | | | 175 | | |
| tac | cta | cac | tcg | gag | gat | tcg | ccg | tac | ttc | tac | ccg | act | gag | ccg | tgg | 576 |
| Tyr | Leu | His | Ser | Glu | Asp | Ser | Pro | Tyr | Phe | Tyr | Pro | Thr | Glu | Pro | Trp | |
| | | | 180 | | | | | 185 | | | | | 190 | | | |
| aag | act | aat | ccg | gag | cac | gtg | gct | cac | gtg | aag | aag | gtg | act | gct | cta | 624 |
| Lys | Thr | Asn | Pro | Glu | His | Val | Ala | His | Val | Lys | Lys | Val | Thr | Ala | Leu | |
| | | 195 | | | | | 200 | | | | | 205 | | | | |
| caa | cga | cta | ggg | act | caa | aaa | gag | ttg | ggg | gaa | ttg | gtg | gca | ttc | ctg | 672 |
| Gln | Arg | Leu | Gly | Thr | Gln | Lys | Glu | Leu | Gly | Glu | Leu | Val | Ala | Phe | Leu | |
| 210 | | | | | 215 | | | | | 220 | | | | | | |
| gca | tct | ggc | tct | tgt | gat | tat | ttg | act | ggc | cag | gtg | ttt | tgg | ttg | gca | 720 |
| Ala | Ser | Gly | Ser | Cys | Asp | Tyr | Leu | Thr | Gly | Gln | Val | Phe | Trp | Leu | Ala | |
| 225 | | | | | 230 | | | | | 235 | | | | | 240 | |
| ggc | ggc | ttt | ccc | ata | ata | gaa | cgt | tgg | ccc | ggc | atg | ccc | gaa | taa | | 765 |
| Gly | Gly | Phe | Pro | Ile | Ile | Glu | Arg | Trp | Pro | Gly | Met | Pro | Glu | * | | |
| | | | | 245 | | | | | 250 | | | | | | | |

<210> SEQ ID NO 30
<211> LENGTH: 254
<212> TYPE: PRT
<213> ORGANISM: Artificial Sequence
<220> FEATURE:
<223> OTHER INFORMATION: HHDH P016014-G-08

<400> SEQUENCE: 30

Met Ser Thr Ala Ile Val Thr Asn Phe Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys Gln Lys Asp Glu Leu Glu Ala Phe Ala Glu Thr Tyr
        35                  40                  45

Pro Gln Leu Lys Pro Met Ser Glu Gln Glu Pro Ala Asp Leu Ile Glu
    50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Glu Asn
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
            115                 120                 125

Phe Ile Thr Ser Ser Thr Pro Phe Gly Pro Trp Lys Glu Leu Ser Thr
        130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Ile Ile Glu Arg Trp Pro Gly Met Pro Glu
                245                 250

<210> SEQ ID NO 31
<211> LENGTH: 765
<212> TYPE: DNA
<213> ORGANISM: Artificial Sequence
<220> FEATURE:
<223> OTHER INFORMATION: HHDH Mz1/2G5
<220> FEATURE:
<221> NAME/KEY: CDS
<222> LOCATION: (1)...(765)

<400> SEQUENCE: 31 atg agc acc gct atc gtc acc aac gtc aaa cat ttt gga ggt atg ggt     48
Met Ser Thr Ala Ile Val Thr Asn Val Lys His Phe Gly Gly Met Gly
1               5                   10                  15 agc gct ctg agg ctg agc gaa gct ggt cat acc gtc gct tgc cat gat     96
Ser Ala Leu Arg Leu Ser Glu Ala Gly His Thr Val Ala Cys His Asp
            20                  25                  30

```
gaa agc ttt aaa cag aaa gat gaa ctg gaa gct ttt gct gaa acc tac      144
Glu Ser Phe Lys Gln Lys Asp Glu Leu Glu Ala Phe Ala Glu Thr Tyr
         35                  40                  45 cca cag ctg aaa cca atg agc gaa cag gaa cca gct gaa ctg atc gaa      192
Pro Gln Leu Lys Pro Met Ser Glu Gln Glu Pro Ala Glu Leu Ile Glu
 50                  55                  60 gct gtc acc agc gct tac ggt cag gtc gat gtc ctg gtc agc aac gat      240
Ala Val Thr Ser Ala Tyr Gly Gln Val Asp Val Leu Val Ser Asn Asp
 65                  70                  75                  80 atc ttt gct cca gaa ttt cag cca atc gat aaa tac gct gtc gaa gat      288
Ile Phe Ala Pro Glu Phe Gln Pro Ile Asp Lys Tyr Ala Val Glu Asp
                 85                  90                  95 tac agg ggt gct gtc gaa gct ctg cag atc agg cca ttt gct cta gtg      336
Tyr Arg Gly Ala Val Glu Ala Leu Gln Ile Arg Pro Phe Ala Leu Val
             100                 105                 110 aat gct gtg gct tcg caa atg aag aag cga aag tcg ggg cac atc atc      384
Asn Ala Val Ala Ser Gln Met Lys Lys Arg Lys Ser Gly His Ile Ile
         115                 120                 125 ttc atc act tcg gct act ccg ttc ggg cca tgg aag gag cta tcg act      432
Phe Ile Thr Ser Ala Thr Pro Phe Gly Pro Trp Lys Glu Leu Ser Thr
130                 135                 140 tac act tcg gct cga gct ggg gct tgt act cta gct aat gct cta tcg      480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat      528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg      576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta      624
Lys Thr Asn Pro Glu His Val Ala His Val Lys Lys Val Thr Ala Leu
        195                 200                 205 caa cga cta ggg act caa aaa gag ttg ggg gaa ttg gtg gca ttt ttg      672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca      720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa          765
Gly Gly Phe Pro Met Ile Glu Arg Trp Pro Gly Met Pro Glu *
                245                 250

<210> SEQ ID NO 32
<211> LENGTH: 254
<212> TYPE: PRT
<213> ORGANISM: Artificial Sequence
<220> FEATURE:
<223> OTHER INFORMATION: HHDH Mz1/2G5

<400> SEQUENCE: 32

Met Ser Thr Ala Ile Val Thr Asn Val Lys His Phe Gly Gly Met Gly
 1               5                  10                  15

Ser Ala Leu Arg Leu Ser Glu Ala Gly His Thr Val Ala Cys His Asp
             20                  25                  30

Glu Ser Phe Lys Gln Lys Asp Glu Leu Glu Ala Phe Ala Glu Thr Tyr
         35                  40                  45

Pro Gln Leu Lys Pro Met Ser Glu Gln Glu Pro Ala Glu Leu Ile Glu
     50                  55                  60

Ala Val Thr Ser Ala Tyr Gly Gln Val Asp Val Leu Val Ser Asn Asp
```

```
                65                  70                  75                  80
        Ile Phe Ala Pro Glu Phe Gln Pro Ile Asp Lys Tyr Ala Val Glu Asp
                            85                  90                  95

Tyr Arg Gly Ala Val Glu Ala Leu Gln Ile Arg Pro Phe Ala Leu Val
                        100                 105                 110

Asn Ala Val Ala Ser Gln Met Lys Lys Arg Lys Ser Gly His Ile Ile
                    115                 120                 125

Phe Ile Thr Ser Ala Thr Pro Phe Gly Pro Trp Lys Glu Leu Ser Thr
                130                 135                 140

Tyr Thr Ser Ala Arg Ala Gly Ala Cys Thr Leu Ala Asn Ala Leu Ser
        145                 150                 155                 160

Lys Glu Leu Gly Glu Tyr Asn Ile Pro Val Phe Ala Ile Gly Pro Asn
                        165                 170                 175

Tyr Leu His Ser Glu Asp Ser Pro Tyr Phe Tyr Pro Thr Glu Pro Trp
                    180                 185                 190

Lys Thr Asn Pro Glu His Val Ala His Val Lys Val Thr Ala Leu
                195                 200                 205

Gln Arg Leu Gly Thr Gln Lys Glu Leu Gly Glu Leu Val Ala Phe Leu
                210                 215                 220

Ala Ser Gly Ser Cys Asp Tyr Leu Thr Gly Gln Val Phe Trp Leu Ala
        225                 230                 235                 240

Gly Gly Phe Pro Met Ile Glu Arg Trp Pro Gly Met Pro Glu
                        245                 250
```

<210> SEQ ID NO 33
<211> LENGTH: 765
<212> TYPE: DNA
<213> ORGANISM: Artificial Sequence
<220> FEATURE:
<223> OTHER INFORMATION: HHDH Mz1.1A5
<220> FEATURE:
<221> NAME/KEY: CDS
<222> LOCATION: (1)...(765)

<400> SEQUENCE: 33

```
atg agc ccc gct atc gtc act aac gtc aaa cat ttt ggt ggt atg ggt        48
Met Ser Pro Ala Ile Val Thr Asn Val Lys His Phe Gly Gly Met Gly
 1               5                  10                  15 acc gct ctg agg ctg agc gaa gct ggt caa acc gtc gct tgc cat gat        96
Thr Ala Leu Arg Leu Ser Glu Ala Gly Gln Thr Val Ala Cys His Asp
                20                  25                  30 gaa agc ttt aaa cag aaa gat gaa ctg gaa gct ttt gct gaa acc tac       144
Glu Ser Phe Lys Gln Lys Asp Glu Leu Glu Ala Phe Ala Glu Thr Tyr
            35                  40                  45 cca cag ctg aaa cca atg agc gaa cag gaa cca gct gaa ctg atc gaa       192
Pro Gln Leu Lys Pro Met Ser Glu Gln Glu Pro Ala Glu Leu Ile Glu
        50                  55                  60 gct gtc acc agc gct tac ggt cag gtc gat gtc ctg gtc agc aac gat       240
Ala Val Thr Ser Ala Tyr Gly Gln Val Asp Val Leu Val Ser Asn Asp
 65                  70                  75                  80 atc ttt gct cca gaa ttt cag cca atc gat aaa tac gct gtc gaa gat       288
Ile Phe Ala Pro Glu Phe Gln Pro Ile Asp Lys Tyr Ala Val Glu Asp
                85                  90                  95 tac agg ggt gct gtc gaa gct ctg cag atc agg cca ttt gct cta gtg       336
Tyr Arg Gly Ala Val Glu Ala Leu Gln Ile Arg Pro Phe Ala Leu Val
                100                 105                 110 aat gct gtg gct tcg caa atg aag aag cga aag tcg ggg cac atc atc       384
Asn Ala Val Ala Ser Gln Met Lys Lys Arg Lys Ser Gly His Ile Ile
            115                 120                 125
```

```
ttc atc act tcg gct act ccg ttc ggg ccg tgg aag gag cta tcg act       432
Phe Ile Thr Ser Ala Thr Pro Phe Gly Pro Trp Lys Glu Leu Ser Thr
    130                 135                 140 tac act tcg gct cga gct ggg gct tgt act cta gct aat gct cta tcg       480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat       528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg       576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta       624
Lys Thr Asn Pro Glu His Val Ala His Val Lys Lys Val Thr Ala Leu
        195                 200                 205 caa cga cta ggg act caa aaa gag ttg ggg gaa ttg gtg gca ttt ttg       672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca       720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa           765
Gly Gly Phe Pro Met Ile Glu Arg Trp Pro Gly Met Pro Glu *
                245                 250

<210> SEQ ID NO 34
<211> LENGTH: 254
<212> TYPE: PRT
<213> ORGANISM: Artificial Sequence
<220> FEATURE:
<223> OTHER INFORMATION: HHDH Mz1.1A5

<400> SEQUENCE: 34

Met Ser Pro Ala Ile Val Thr Asn Val Lys His Phe Gly Gly Met Gly
1               5                   10                  15

Thr Ala Leu Arg Leu Ser Glu Ala Gly Gln Thr Val Ala Cys His Asp
            20                  25                  30

Glu Ser Phe Lys Gln Lys Asp Glu Leu Glu Ala Phe Ala Glu Thr Tyr
        35                  40                  45

Pro Gln Leu Lys Pro Met Ser Glu Gln Glu Pro Ala Glu Leu Ile Glu
    50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Glu Asp
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
    130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190
```

```
                Lys Thr Asn Pro Glu His Val Ala His Val Lys Lys Val Thr Ala Leu
                            195                 200                 205

Gln Arg Leu Gly Thr Gln Lys Glu Leu Gly Glu Leu Val Ala Phe Leu
                            210                 215                 220

Ala Ser Gly Ser Cys Asp Tyr Leu Thr Gly Gln Val Phe Trp Leu Ala
                225                 230                 235                 240

Gly Gly Phe Pro Met Ile Glu Arg Trp Pro Gly Met Pro Glu
                                    245                 250

<210> SEQ ID NO 35
<211> LENGTH: 765
<212> TYPE: DNA
<213> ORGANISM: Artificial Sequence
<220> FEATURE:
<223> OTHER INFORMATION: HHDH cys1.10
<220> FEATURE:
<221> NAME/KEY: CDS
<222> LOCATION: (1)...(765)

<400> SEQUENCE: 35 atg agc acc gct atc gtc acc aac gtc aaa cat ttt gga ggt atg ggt      48
Met Ser Thr Ala Ile Val Thr Asn Val Lys His Phe Gly Gly Met Gly
  1               5                  10                  15 agc gct ctg agg ctg agc gaa gct ggt cat acc gtc gct tgc cat gat      96
Ser Ala Leu Arg Leu Ser Glu Ala Gly His Thr Val Ala Cys His Asp
                 20                  25                  30 gaa agc ttt aaa cag aaa gat gaa ctg gaa gct ttt gct gaa acc tac     144
Glu Ser Phe Lys Gln Lys Asp Glu Leu Glu Ala Phe Ala Glu Thr Tyr
             35                  40                  45 cca cag ctg aaa cca atg agc gaa cag gaa cca gct gaa ctg atc gaa     192
Pro Gln Leu Lys Pro Met Ser Glu Gln Glu Pro Ala Glu Leu Ile Glu
         50                  55                  60 gct gtc acc agc gct tac ggt cag gtc gat gtc ctg gtc agc aac gat     240
Ala Val Thr Ser Ala Tyr Gly Gln Val Asp Val Leu Val Ser Asn Asp
 65                  70                  75                  80 atc ttt gct cca gaa ttt cag cca atc gat aaa tac gct gtc gaa gat     288
Ile Phe Ala Pro Glu Phe Gln Pro Ile Asp Lys Tyr Ala Val Glu Asp
                 85                  90                  95 tac agg ggt gct gtc gaa gct ctg cag atc agg cca ttt gct cta gtg     336
Tyr Arg Gly Ala Val Glu Ala Leu Gln Ile Arg Pro Phe Ala Leu Val
            100                 105                 110 aat gct gtg gct tcg caa atg aag aag cga aag tcg ggg cac atc atc     384
Asn Ala Val Ala Ser Gln Met Lys Lys Arg Lys Ser Gly His Ile Ile
            115                 120                 125 ttc atc act tcg gct act ccg ttc ggg cca tgg aag gag cta tcg act     432
Phe Ile Thr Ser Ala Thr Pro Phe Gly Pro Trp Lys Glu Leu Ser Thr
        130                 135                 140 tac act tcg gct cga gct ggg gct agt act cta gct aat gct cta tcg     480
Tyr Thr Ser Ala Arg Ala Gly Ala Ser Thr Leu Ala Asn Ala Leu Ser
145                 150                 155                 160 aag gag cta gga gag tac aat atc ccg gtg ttc gct atc ggg ccg aat     528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg     576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta     624
Lys Thr Asn Pro Glu His Val Ala His Val Lys Lys Val Thr Ala Leu
            195                 200                 205 caa cga cta ggg act caa aaa gag ttg ggg gaa ttg gtg gca ttt ttg     672
Gln Arg Leu Gly Thr Gln Lys Glu Leu Gly Glu Leu Val Ala Phe Leu
```

```
      210                 215                 220
gca tct ggc tct tgt gat tat ttg act ggc cag gtg ttt tgg ttg gca    720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa        765
Gly Gly Phe Pro Met Ile Glu Arg Trp Pro Gly Met Pro Glu *
                245                 250
```

<210> SEQ ID NO 36
<211> LENGTH: 254
<212> TYPE: PRT
<213> ORGANISM: Artificial Sequence
<220> FEATURE:
<223> OTHER INFORMATION: HHDH cys1.10

<400> SEQUENCE: 36

```
Met Ser Thr Ala Ile Val Thr Asn Val Lys His Phe Gly Gly Met Gly
 1               5                  10                  15

Ser Ala Leu Arg Leu Ser Glu Ala Gly His Thr Val Ala Cys His Asp
                20                  25                  30

Glu Ser Phe Lys Gln Lys Asp Glu Leu Glu Ala Phe Ala Glu Thr Tyr
            35                  40                  45

Pro Gln Leu Lys Pro Met Ser Glu Gln Glu Pro Ala Glu Leu Ile Glu
        50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Glu Asp
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
    130                 135                 140

Tyr Thr Ser Ala Arg Ala Gly Ala Ser Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250
```

<210> SEQ ID NO 37
<211> LENGTH: 765
<212> TYPE: DNA
<213> ORGANISM: Artificial Sequence
<220> FEATURE:
<223> OTHER INFORMATION: HHDH cys2.12
<220> FEATURE:
<221> NAME/KEY: CDS
<222> LOCATION: (1)...(765)

<400> SEQUENCE: 37

```
atg agc acc gct atc gtc acc aac gtc aaa cat ttt gga ggt atg ggt      48
Met Ser Thr Ala Ile Val Thr Asn Val Lys His Phe Gly Gly Met Gly
 1               5                  10                  15 agc gct ctg agg ctg agc gaa gct ggt cat acc gtc gct gcg cat gat      96
Ser Ala Leu Arg Leu Ser Glu Ala Gly His Thr Val Ala Ala His Asp
             20                  25                  30 gaa agc ttt aaa cag aaa gat gaa ctg gaa gct ttt gct gaa acc tac     144
Glu Ser Phe Lys Gln Lys Asp Glu Leu Glu Ala Phe Ala Glu Thr Tyr
         35                  40                  45 cca cag ctg aaa cca atg agc gaa cag gaa cca gct gaa ctg atc gaa     192
Pro Gln Leu Lys Pro Met Ser Glu Gln Glu Pro Ala Glu Leu Ile Glu
     50                  55                  60 gct gtc acc agc gct tac ggt cag gtc gat gtc ctg gtc agc aac gat     240
Ala Val Thr Ser Ala Tyr Gly Gln Val Asp Val Leu Val Ser Asn Asp
 65                  70                  75                  80 atc ttt gct cca gaa ttt cag cca atc gat aaa tac gct gtc gaa gat     288
Ile Phe Ala Pro Glu Phe Gln Pro Ile Asp Lys Tyr Ala Val Glu Asp
                 85                  90                  95 tac agg ggt gct gtc gaa gct ctg cag atc agg cca ttt gct cta gtg     336
Tyr Arg Gly Ala Val Glu Ala Leu Gln Ile Arg Pro Phe Ala Leu Val
            100                 105                 110 aat gct gtg gct tcg caa atg aag aag cga aag tcg ggg cac atc atc     384
Asn Ala Val Ala Ser Gln Met Lys Lys Arg Lys Ser Gly His Ile Ile
        115                 120                 125 ttc atc act tcg gct act ccg ttc ggg cca tgg aag gag cta tcg act     432
Phe Ile Thr Ser Ala Thr Pro Phe Gly Pro Trp Lys Glu Leu Ser Thr
    130                 135                 140 tac act tcg gct cga gct ggg gct tgt act cta gct aat gct cta tcg     480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat     528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg     576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta     624
Lys Thr Asn Pro Glu His Val Ala His Val Lys Lys Val Thr Ala Leu
        195                 200                 205 caa cga cta ggg act caa aaa gag ttg ggg gaa ttg gtg gca ttt ttg     672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca     720
Ala Ser Gly Ser Cys Asp Tyr Leu Thr Gly Gln Val Phe Trp Leu Ala
225                 230                 235                 240 ggc ggt ttt ccc atg ata gaa cgt tgg ccc ggc atg ccc gaa taa         765
Gly Gly Phe Pro Met Ile Glu Arg Trp Pro Gly Met Pro Glu *
                245                 250
```

<210> SEQ ID NO 38
<211> LENGTH: 254
<212> TYPE: PRT
<213> ORGANISM: Artificial Sequence
<220> FEATURE:
<223> OTHER INFORMATION: HHDH cys2.12

<400> SEQUENCE: 38

```
Met Ser Thr Ala Ile Val Thr Asn Val Lys His Phe Gly Gly Met Gly
 1               5                  10                  15
```

```
Ser Ala Leu Arg Leu Ser Glu Ala Gly His Thr Val Ala Ala His Asp
         20                  25                  30

Glu Ser Phe Lys Gln Lys Asp Glu Leu Glu Ala Phe Ala Glu Thr Tyr
             35                  40                  45

Pro Gln Leu Lys Pro Met Ser Glu Gln Glu Pro Ala Glu Leu Ile Glu
 50                  55                  60

Ala Val Thr Ser Ala Tyr Gly Gln Val Asp Val Leu Val Ser Asn Asp
 65                  70                  75                  80

Ile Phe Ala Pro Glu Phe Gln Pro Ile Asp Lys Tyr Ala Val Glu Asp
                 85                  90                  95

Tyr Arg Gly Ala Val Glu Ala Leu Gln Ile Arg Pro Phe Ala Leu Val
                100                 105                 110

Asn Ala Val Ala Ser Gln Met Lys Lys Arg Lys Ser Gly His Ile Ile
            115                 120                 125

Phe Ile Thr Ser Ala Thr Pro Phe Gly Pro Trp Lys Glu Leu Ser Thr
130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250

<210> SEQ ID NO 39
<211> LENGTH: 852
<212> TYPE: DNA
<213> ORGANISM: Artificial Sequence
<220> FEATURE:
<223> OTHER INFORMATION: KRED krh133c
<220> FEATURE:
<221> NAME/KEY: CDS
<222> LOCATION: (1)...(852)

<400> SEQUENCE: 39 atg gct aaa aac ttt agc aat gtc gaa tat cct gcc ccg ccg cca gct    48
Met Ala Lys Asn Phe Ser Asn Val Glu Tyr Pro Ala Pro Pro Pro Ala
 1               5                  10                  15 cat acc aaa aac gaa tca ctg cag gta ctg gat ctg ttc aaa ctg aac    96
His Thr Lys Asn Glu Ser Leu Gln Val Leu Asp Leu Phe Lys Leu Asn
             20                  25                  30 ggc aaa gtc gcg tct atc acc ggt agc agc tca ggc att ggt tac gcg   144
Gly Lys Val Ala Ser Ile Thr Gly Ser Ser Ser Gly Ile Gly Tyr Ala
         35                  40                  45 ctg gcc gaa gct ttt gcg cag gtt ggc gca gac gtt gcg atc tgg tat   192
Leu Ala Glu Ala Phe Ala Gln Val Gly Ala Asp Val Ala Ile Trp Tyr
 50                  55                  60 aac agc cag gat gcc acc ggt aaa gca gag gcc ctg gct aaa aaa tat   240
Asn Ser Gln Asp Ala Thr Gly Lys Ala Glu Ala Leu Ala Lys Lys Tyr
 65                  70                  75                  80 ggc gta aaa gtc aag gct tat aaa gct aat gtc agc tcg agt gat gcg   288
```

```
Gly Val Lys Val Lys Ala Tyr Lys Ala Asn Val Ser Ser Ser Asp Ala
            85                  90                  95 gtg aaa cag act att gag cag cag atc aag gat ttt ggc cac ctg gac      336
Val Lys Gln Thr Ile Glu Gln Gln Ile Lys Asp Phe Gly His Leu Asp
            100                 105                 110 att gtt gtg gcg aac gca ggc atc cca tgg act aag ggt gca tac atc      384
Ile Val Val Ala Asn Ala Gly Ile Pro Trp Thr Lys Gly Ala Tyr Ile
            115                 120                 125 gat cag gat gac gat aaa cat ttt gac cag gtg gtg gac gtc gac ctg      432
Asp Gln Asp Asp Asp Lys His Phe Asp Gln Val Val Asp Val Asp Leu
130                 135                 140 aaa ggc gta ggc tat gta gca aaa cat gcg ggt cgc cat tat cgt gaa      480
Lys Gly Val Gly Tyr Val Ala Lys His Ala Gly Arg His Tyr Arg Glu
145                 150                 155                 160 cgt ttc gaa aaa gaa ggc aaa aag ggc gcc ttg gtt ttt acg gct tcc      528
Arg Phe Glu Lys Glu Gly Lys Lys Gly Ala Leu Val Phe Thr Ala Ser
                165                 170                 175 atg tcg ggt cac atc gtt aac gtg ccg caa ttt cag gcg acc tac aat      576
Met Ser Gly His Ile Val Asn Val Pro Gln Phe Gln Ala Thr Tyr Asn
            180                 185                 190 gcg gcc aag gca ggc gtg cgt cat ttc gca aag tcc ctg gcc gtg gaa      624
Ala Ala Lys Ala Gly Val Arg His Phe Ala Lys Ser Leu Ala Val Glu
            195                 200                 205 ttt gct cct ttc gca cgt gtt aac tct gta tct cct ggc tat att aat      672
Phe Ala Pro Phe Ala Arg Val Asn Ser Val Ser Pro Gly Tyr Ile Asn
210                 215                 220 acc gag atc tct gat ttc gtc ccg caa gaa aca caa aat aaa tgg tgg      720
Thr Glu Ile Ser Asp Phe Val Pro Gln Glu Thr Gln Asn Lys Trp Trp
225                 230                 235                 240 agc tta gtt cca ttg ggt cgt ggt ggg gaa act gcg gaa tta gtt ggt      768
Ser Leu Val Pro Leu Gly Arg Gly Gly Glu Thr Ala Glu Leu Val Gly
                245                 250                 255 gcc tac ctg ttc ctg gca agt gat gcg ggc tcc tac gcc acg ggc aca      816
Ala Tyr Leu Phe Leu Ala Ser Asp Ala Gly Ser Tyr Ala Thr Gly Thr
            260                 265                 270 gat atc att gtg gat ggc ggc tac acg ctg ccg taa                      852
Asp Ile Ile Val Asp Gly Gly Tyr Thr Leu Pro  *
            275                 280
```

<210> SEQ ID NO 40
<211> LENGTH: 283
<212> TYPE: PRT
<213> ORGANISM: Artificial Sequence
<220> FEATURE:
<223> OTHER INFORMATION: KRED krh133c

<400> SEQUENCE: 40

```
Met Ala Lys Asn Phe Ser Asn Val Glu Tyr Pro Ala Pro Pro Pro Ala
1               5                   10                  15

His Thr Lys Asn Glu Ser Leu Gln Val Leu Asp Leu Phe Lys Leu Asn
            20                  25                  30

Gly Lys Val Ala Ser Ile Thr Gly Ser Ser Ser Gly Ile Gly Tyr Ala
            35                  40                  45

Leu Ala Glu Ala Phe Ala Gln Val Gly Ala Asp Val Ala Ile Trp Tyr
        50                  55                  60

Asn Ser Gln Asp Ala Thr Gly Lys Ala Glu Leu Ala Lys Lys Tyr
65                  70                  75                  80

Gly Val Lys Val Lys Ala Tyr Lys Ala Asn Val Ser Ser Ser Asp Ala
            85                  90                  95
```

```
Val Lys Gln Thr Ile Glu Gln Gln Ile Lys Asp Phe Gly His Leu Asp
            100                 105                 110

Ile Val Val Ala Asn Ala Gly Ile Pro Trp Thr Lys Gly Ala Tyr Ile
        115                 120                 125

Asp Gln Asp Asp Lys His Phe Asp Gln Val Asp Val Asp Leu
    130                 135                 140

Lys Gly Val Gly Tyr Val Ala Lys His Ala Gly Arg His Tyr Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Ala Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
    210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
        275                 280
```

<210> SEQ ID NO 41
<211> LENGTH: 855
<212> TYPE: DNA
<213> ORGANISM: Artificial Sequence
<220> FEATURE:
<223> OTHER INFORMATION: KRED krh215
<220> FEATURE:
<221> NAME/KEY: CDS
<222> LOCATION: (1)...(855)

<400> SEQUENCE: 41

```
atg gct aaa aac ttt agc aat gtc gaa tat cct gcc ccg ccg cca gct      48
Met Ala Lys Asn Phe Ser Asn Val Glu Tyr Pro Ala Pro Pro Pro Ala
 1               5                  10                  15 cat acc aaa aac gaa tca ctg cag gta ctg gat ctg ttc aaa ctg aac      96
His Thr Lys Asn Glu Ser Leu Gln Val Leu Asp Leu Phe Lys Leu Asn
                20                  25                  30 ggc aaa gtc gcg tct atc acc ggt agc agc tca ggc att ggt tac gcg     144
Gly Lys Val Ala Ser Ile Thr Gly Ser Ser Ser Gly Ile Gly Tyr Ala
            35                  40                  45 ctg gcc gaa gct ttt gcg cag gtt ggc gca gac gtt gcg atc tgg tat     192
Leu Ala Glu Ala Phe Ala Gln Val Gly Ala Asp Val Ala Ile Trp Tyr
        50                  55                  60 aac agc cag gat gcc acc ggt aaa gca gag gcc ctg gct aaa aaa tat     240
Asn Ser Gln Asp Ala Thr Gly Lys Ala Glu Ala Leu Ala Lys Lys Tyr
 65                  70                  75                  80 ggc gta aaa gtc aag gct tat aaa gct aat gtc agc tcg agt gat gcg     288
Gly Val Lys Val Lys Ala Tyr Lys Ala Asn Val Ser Ser Ser Asp Ala
                 85                  90                  95 gtg aaa cag act att gag cag cag atc aag gat ttt ggc cac ctg gac     336
Val Lys Gln Thr Ile Glu Gln Gln Ile Lys Asp Phe Gly His Leu Asp
            100                 105                 110 att gtt gtg gcg aac gca ggc atc cca tgg act aag ggt gca tac atc     384
Ile Val Val Ala Asn Ala Gly Ile Pro Trp Thr Lys Gly Ala Tyr Ile
        115                 120                 125
```

```
                   115                 120                 125
gat cag gat gac gat aaa cat ttt gac cag gtg att gac gtc gac ctg         432
Asp Gln Asp Asp Asp Lys His Phe Asp Gln Val Ile Asp Val Asp Leu
        130                 135                 140 aaa ggc gta ggc tat gta gca aaa cat gcg ggt cgc cat tat cgt gaa         480
Lys Gly Val Gly Tyr Val Ala Lys His Ala Gly Arg His Tyr Arg Glu
145                 150                 155                 160 cgt ttc gaa aaa gaa ggc ata aag ggc gcc ttg att ttt acg gct tcc         528
Arg Phe Glu Lys Glu Gly Ile Lys Gly Ala Leu Ile Phe Thr Ala Ser
                165                 170                 175 gtg tcg ggt cac atc gtt aac att ccg caa ttt cag gcg acc tac aat         576
Val Ser Gly His Ile Val Asn Ile Pro Gln Phe Gln Ala Thr Tyr Asn
            180                 185                 190 gcg gcc aag gca ggc gtg cgt cat ttc gca aag tcc ctg gcc gtg gaa         624
Ala Ala Lys Ala Gly Val Arg His Phe Ala Lys Ser Leu Ala Val Glu
        195                 200                 205 ttt gct cct ttc gca cgt gtt aac tct gta tct cct ggc tat att aat         672
Phe Ala Pro Phe Ala Arg Val Asn Ser Val Ser Pro Gly Tyr Ile Asn
    210                 215                 220 acc gag atc tct gat ttc gtc ccg caa gaa aca caa aat aaa tgg tgg         720
Thr Glu Ile Ser Asp Phe Val Pro Gln Glu Thr Gln Asn Lys Trp Trp
225                 230                 235                 240 agc tta gtt cca ttg ggt cgt ggt ggg gaa act gcg gaa tta gtt ggt         768
Ser Leu Val Pro Leu Gly Arg Gly Gly Glu Thr Ala Glu Leu Val Gly
                245                 250                 255 gcc tac ctg ttc ctg gca agt gat gcg ggc tcc tac gcc acg ggc aca         816
Ala Tyr Leu Phe Leu Ala Ser Asp Ala Gly Ser Tyr Ala Thr Gly Thr
            260                 265                 270 gat atc att gtg gat ggc ggc tac acg ctg ccg taa tga                     855
Asp Ile Ile Val Asp Gly Gly Tyr Thr Leu Pro *   *
        275                 280

<210> SEQ ID NO 42
<211> LENGTH: 283
<212> TYPE: PRT
<213> ORGANISM: Artificial Sequence
<220> FEATURE:
<223> OTHER INFORMATION: KRED krh215

<400> SEQUENCE: 42

Met Ala Lys Asn Phe Ser Asn Val Glu Tyr Pro Ala Pro Pro Pro Ala
1               5                   10                  15

His Thr Lys Asn Glu Ser Leu Gln Val Leu Asp Leu Phe Lys Leu Asn
            20                  25                  30

Gly Lys Val Ala Ser Ile Thr Gly Ser Ser Gly Ile Gly Tyr Ala
        35                  40                  45

Leu Ala Glu Ala Phe Ala Gln Val Gly Ala Asp Val Ala Ile Trp Tyr
    50                  55                  60

Asn Ser Gln Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Ser Asp Ala
                85                  90                  95

Val Lys Gln Thr Ile Glu Gln Ile Lys Asp Phe Gly His Leu Asp
            100                 105                 110

Ile Val Val Ala Asn Ala Gly Ile Pro Trp Thr Lys Gly Ala Tyr Ile
    115                 120                 125

Asp Gln Asp Asp Asp Lys His Phe Asp Gln Val Ile Asp Val Asp Leu
    130                 135                 140
```

```
Lys Gly Val Gly Tyr Val Ala Lys His Ala Gly Arg His Tyr Arg Glu
145                 150                 155                 160

Arg Phe Glu Lys Glu Gly Ile Lys Gly Ala Leu Ile Phe Thr Ala Ser
                165                 170                 175

Val Ser Gly His Ile Val Asn Ile Pro Gln Phe Gln Ala Thr Tyr Asn
            180                 185                 190

Ala Ala Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
    210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
        275                 280
```

<210> SEQ ID NO 43
<211> LENGTH: 855
<212> TYPE: DNA
<213> ORGANISM: Artificial Sequence
<220> FEATURE:
<223> OTHER INFORMATION: KRED krh267
<220> FEATURE:
<221> NAME/KEY: CDS
<222> LOCATION: (1)...(855)

<400> SEQUENCE: 43

```
atg gct aaa aac ttt agc aat gtc gaa tat cct gcc ccg ccg cca gct        48
Met Ala Lys Asn Phe Ser Asn Val Glu Tyr Pro Ala Pro Pro Pro Ala
 1               5                  10                  15 cat acc aaa aac gaa tca ctg cag gta ctg gat ctg ttc aaa ctg aac        96
His Thr Lys Asn Glu Ser Leu Gln Val Leu Asp Leu Phe Lys Leu Asn
                20                  25                  30 ggc aaa gtc gcg tct atc acc ggt agc agc tca ggc att ggt tac gcg       144
Gly Lys Val Ala Ser Ile Thr Gly Ser Ser Ser Gly Ile Gly Tyr Ala
            35                  40                  45 ctg gcc gaa gct ttt gcg cag gtt ggc gca gac gtt gcg atc tgg tat       192
Leu Ala Glu Ala Phe Ala Gln Val Gly Ala Asp Val Ala Ile Trp Tyr
        50                  55                  60 aac agc cag gat gcc acc ggt aaa gca gag gcc ctg gct aaa aaa tat       240
Asn Ser Gln Asp Ala Thr Gly Lys Ala Glu Ala Leu Ala Lys Lys Tyr
 65                 70                  75                  80 ggc gta aaa gtc aag gct tat aaa gct aat gtc agc tcg agt gat gcg       288
Gly Val Lys Val Lys Ala Tyr Lys Ala Asn Val Ser Ser Ser Asp Ala
                85                  90                  95 gtg aaa cag act att gag cag cag atc aag gat ttt ggc cac ctg gac       336
Val Lys Gln Thr Ile Glu Gln Gln Ile Lys Asp Phe Gly His Leu Asp
            100                 105                 110 att gtt gtg gcg aac gca ggc atc cca tgg act aag ggt gca tac atc       384
Ile Val Val Ala Asn Ala Gly Ile Pro Trp Thr Lys Gly Ala Tyr Ile
        115                 120                 125 gat cag gat gac gat aag cat ttt gac cag gtg att gac gtc gac ctg       432
Asp Gln Asp Asp Asp Lys His Phe Asp Gln Val Ile Asp Val Asp Leu
    130                 135                 140 aaa ggc gta ggc tat gta gca aaa cat gcg ggt cgc cat ctt cgt gaa       480
Lys Gly Val Gly Tyr Val Ala Lys His Ala Gly Arg His Leu Arg Glu
145                 150                 155                 160
```

```
cgt ttc gaa aaa gaa ggc aaa aag ggc gcc ttg gtt ttt acg gct tcc      528
Arg Phe Glu Lys Glu Gly Lys Lys Gly Ala Leu Val Phe Thr Ala Ser
                165                 170                 175 acg tcg ggt cac atc gtt aac att ccg caa ttt cag gcg acc tac aat      576
Thr Ser Gly His Ile Val Asn Ile Pro Gln Phe Gln Ala Thr Tyr Asn
            180                 185                 190 gcg gcc aag gca ggc gtg cgt cat ttc gca aag tcc ctg gcc gtg gaa      624
Ala Ala Lys Ala Gly Val Arg His Phe Ala Lys Ser Leu Ala Val Glu
        195                 200                 205 ttt gct cct ttc gca cgt gtt aac tct gta tct cct ggc tat att aat      672
Phe Ala Pro Phe Ala Arg Val Asn Ser Val Ser Pro Gly Tyr Ile Asn
    210                 215                 220 acc gag atc tct gat ttc gtc ccg caa gaa aca caa aat aaa tgg tgg      720
Thr Glu Ile Ser Asp Phe Val Pro Gln Glu Thr Gln Asn Lys Trp Trp
225                 230                 235                 240 agc tta gtt cca ttg ggt cgt ggt ggg gaa act gcg gaa tta gtt ggt      768
Ser Leu Val Pro Leu Gly Arg Gly Gly Glu Thr Ala Glu Leu Val Gly
                245                 250                 255 gcc tac ctg ttc ctg gca agt gat gcg ggc tcc tac gcc acg ggc aca      816
Ala Tyr Leu Phe Leu Ala Ser Asp Ala Gly Ser Tyr Ala Thr Gly Thr
            260                 265                 270 gat atc att gtg gat ggc ggc tac acg ctg ccg taa tga                  855
Asp Ile Ile Val Asp Gly Gly Tyr Thr Leu Pro *   *
        275                 280

<210> SEQ ID NO 44
<211> LENGTH: 283
<212> TYPE: PRT
<213> ORGANISM: Artificial Sequence
<220> FEATURE:
<223> OTHER INFORMATION: KRED krh267

<400> SEQUENCE: 44

Met Ala Lys Asn Phe Ser Asn Val Glu Tyr Pro Ala Pro Pro Ala
 1               5                  10                  15

His Thr Lys Asn Glu Ser Leu Gln Val Leu Asp Leu Phe Lys Leu Asn
                20                  25                  30

Gly Lys Val Ala Ser Ile Thr Gly Ser Ser Gly Ile Gly Tyr Ala
            35                  40                  45

Leu Ala Glu Ala Phe Ala Gln Val Gly Ala Asp Val Ala Ile Trp Tyr
        50                  55                  60

Asn Ser Gln Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Asp Ala
                85                  90                  95

Val Lys Gln Thr Ile Glu Gln Ile Lys Asp Phe Gly His Leu Asp
            100                 105                 110

Ile Val Val Ala Asn Ala Gly Ile Pro Trp Thr Lys Gly Ala Tyr Ile
        115                 120                 125

Asp Gln Asp Asp Asp Lys His Phe Asp Gln Val Ile Asp Val Asp Leu
    130                 135                 140

Lys Gly Val Gly Tyr Val Ala Lys His Ala Gly Arg His Leu Arg Glu
145                 150                 155                 160

Arg Phe Glu Lys Glu Gly Lys Lys Gly Ala Leu Val Phe Thr Ala Ser
                165                 170                 175

Thr Ser Gly His Ile Val Asn Ile Pro Gln Phe Gln Ala Thr Tyr Asn
            180                 185                 190
```

```
Ala Ala Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
        210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
            275                 280

<210> SEQ ID NO 45
<211> LENGTH: 855
<212> TYPE: DNA
<213> ORGANISM: Artificial Sequence
<220> FEATURE:
<223> OTHER INFORMATION: KRED krh287
<220> FEATURE:
<221> NAME/KEY: CDS
<222> LOCATION: (1)...(855)

<400> SEQUENCE: 45 atg gct aaa aac ttt agc aat gtc gaa tac cct gcc ccg ccg cca gct      48
Met Ala Lys Asn Phe Ser Asn Val Glu Tyr Pro Ala Pro Pro Pro Ala
1               5                   10                  15 cat acc aaa aac gaa tca ctg cag gta ctg gat ctg ttc aaa ctg aac      96
His Thr Lys Asn Glu Ser Leu Gln Val Leu Asp Leu Phe Lys Leu Asn
            20                  25                  30 ggc aaa gtc gcg tct atc acc ggt agc aac tca ggc att ggt tac gcg     144
Gly Lys Val Ala Ser Ile Thr Gly Ser Asn Ser Gly Ile Gly Tyr Ala
        35                  40                  45 ctg gcc gaa gct ttt gcg cag gtt ggc gca gac gtt gcg atc tgg tat     192
Leu Ala Glu Ala Phe Ala Gln Val Gly Ala Asp Val Ala Ile Trp Tyr
    50                  55                  60 aac agc cat gat gcc acc ggt aaa gca gag gcc ctg gct aaa aaa tat     240
Asn Ser His Asp Ala Thr Gly Lys Ala Glu Ala Leu Ala Lys Lys Tyr
65                  70                  75                  80 ggc gta aaa gtc aag gct tat aaa gct aat gtc agc tcg agt gat gcg     288
Gly Val Lys Val Lys Ala Tyr Lys Ala Asn Val Ser Ser Ser Asp Ala
                85                  90                  95 gtg aaa cag act att gag cag cag atc aag gat ttt ggc cac ctg gac     336
Val Lys Gln Thr Ile Glu Gln Gln Ile Lys Asp Phe Gly His Leu Asp
            100                 105                 110 att gtt gtg gcg aac gca ggc atc cca tgg act aag ggt gca tac atc     384
Ile Val Val Ala Asn Ala Gly Ile Pro Trp Thr Lys Gly Ala Tyr Ile
        115                 120                 125 gat cag gat gac gat aaa cat ttt gac cag gtg gtg gac gtc gac ctg     432
Asp Gln Asp Asp Asp Lys His Phe Asp Gln Val Val Asp Val Asp Leu
    130                 135                 140 aaa ggc gta ggc tat gta gca aaa cat gcg ggt cgc cat ttt cgt gaa     480
Lys Gly Val Gly Tyr Val Ala Lys His Ala Gly Arg His Phe Arg Glu
145                 150                 155                 160 cgt ttc gaa aaa gaa ggc aaa aag ggc gcc ttg gtt ttt acg gct tcc     528
Arg Phe Glu Lys Glu Gly Lys Lys Gly Ala Leu Val Phe Thr Ala Ser
                165                 170                 175 atg tcg ggt cac atc gtt aac gtg ccg caa ttt cag gcg acc tac aat     576
Met Ser Gly His Ile Val Asn Val Pro Gln Phe Gln Ala Thr Tyr Asn
            180                 185                 190
```

```
gcg gcc aag gca ggc gtg cgt cat ttc gca aag tcc ctg gcc gtg gaa      624
Ala Ala Lys Ala Gly Val Arg His Phe Ala Lys Ser Leu Ala Val Glu
        195                 200                 205 ttt gct cct ttc gca cgt gtt aac tct gta tct cct ggc tat att aat      672
Phe Ala Pro Phe Ala Arg Val Asn Ser Val Ser Pro Gly Tyr Ile Asn
210                 215                 220 acc gag atc tct gat ttc gtc ccg caa gaa aca caa aat aaa tgg tgg      720
Thr Glu Ile Ser Asp Phe Val Pro Gln Glu Thr Gln Asn Lys Trp Trp
225                 230                 235                 240 agc tta gtt cca ttg ggc cgt ggt ggg gaa act gcg gaa tta gtt ggt      768
Ser Leu Val Pro Leu Gly Arg Gly Gly Glu Thr Ala Glu Leu Val Gly
            245                 250                 255 gcc tac ctg ttc ctg gca agt gat gcg ggc tcc tac gcc acg ggc aca      816
Ala Tyr Leu Phe Leu Ala Ser Asp Ala Gly Ser Tyr Ala Thr Gly Thr
        260                 265                 270 gat atc att gtg gac ggc ggc tac acg ctg ccg taa tga                  855
Asp Ile Ile Val Asp Gly Gly Tyr Thr Leu Pro *   *
        275                 280
```

<210> SEQ ID NO 46
<211> LENGTH: 283
<212> TYPE: PRT
<213> ORGANISM: Artificial Sequence
<220> FEATURE:
<223> OTHER INFORMATION: KRED krh287

<400> SEQUENCE: 46

```
Met Ala Lys Asn Phe Ser Asn Val Glu Tyr Pro Ala Pro Pro Pro Ala
1               5                   10                  15

His Thr Lys Asn Glu Ser Leu Gln Val Leu Asp Leu Phe Lys Leu Asn
                20                  25                  30

Gly Lys Val Ala Ser Ile Thr Gly Ser Asn Ser Gly Ile Gly Tyr Ala
            35                  40                  45

Leu Ala Glu Ala Phe Ala Gln Val Gly Ala Asp Val Ala Ile Trp Tyr
        50                  55                  60

Asn Ser His Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Ser Asp Ala
                85                  90                  95

Val Lys Gln Thr Ile Glu Gln Gln Ile Lys Asp Phe Gly His Leu Asp
            100                 105                 110

Ile Val Val Ala Asn Ala Gly Ile Pro Trp Thr Lys Gly Ala Tyr Ile
        115                 120                 125

Asp Gln Asp Asp Asp Lys His Phe Asp Gln Val Val Asp Val Asp Leu
    130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Ala Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
    210                 215                 220

Thr Glu Ile Ser Asp Phe Val Pro Gln Glu Thr Gln Asn Lys Trp Trp
225                 230                 235                 240
```

```
Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
        275                 280

<210> SEQ ID NO 47
<211> LENGTH: 855
<212> TYPE: DNA
<213> ORGANISM: Artificial Sequence
<220> FEATURE:
<223> OTHER INFORMATION: KRED krh320
<220> FEATURE:
<221> NAME/KEY: CDS
<222> LOCATION: (1)...(855)

<400> SEQUENCE: 47 atg gct aaa aac ttt agc aat gtc gaa tac cct gcc ccg ccg cca gct     48
Met Ala Lys Asn Phe Ser Asn Val Glu Tyr Pro Ala Pro Pro Pro Ala
 1               5                  10                  15 cat acc aaa aac gaa tca ctg cag gta ctg gat ctg ttc aaa ctg aac     96
His Thr Lys Asn Glu Ser Leu Gln Val Leu Asp Leu Phe Lys Leu Asn
             20                  25                  30 ggc aaa gtc gcg tct atc acc ggt agc aac tca ggc att ggt tac gcg    144
Gly Lys Val Ala Ser Ile Thr Gly Ser Asn Ser Gly Ile Gly Tyr Ala
         35                  40                  45 ctg gcc gaa gct ttt gcg cag gtt ggc gca gac gtt gcg atc tgg tat    192
Leu Ala Glu Ala Phe Ala Gln Val Gly Ala Asp Val Ala Ile Trp Tyr
     50                  55                  60 aac agc cat gat gcc acc ggt aaa gca gag gcc ctg gct aaa aaa tat    240
Asn Ser His Asp Ala Thr Gly Lys Ala Glu Ala Leu Ala Lys Lys Tyr
 65                  70                  75                  80 ggc gta aaa gtc aag gct tat aaa gct aat gtc agc tcg agt tat gcg    288
Gly Val Lys Val Lys Ala Tyr Lys Ala Asn Val Ser Ser Ser Tyr Ala
                 85                  90                  95 gtg aaa cag act att gag cag cag atc aag gat ttt ggc cac ctg gac    336
Val Lys Gln Thr Ile Glu Gln Gln Ile Lys Asp Phe Gly His Leu Asp
            100                 105                 110 att gtt gtg gcg aac gca ggc atc cca tgg act aag ggt gca tac atc    384
Ile Val Val Ala Asn Ala Gly Ile Pro Trp Thr Lys Gly Ala Tyr Ile
        115                 120                 125 gat cag gat gac gat aaa cat ttt gac cag gtg gtg gac gtc gac ctg    432
Asp Gln Asp Asp Asp Lys His Phe Asp Gln Val Val Asp Val Asp Leu
    130                 135                 140 aaa ggc gta ggc tat gta gca aaa cat gcg ggt cgc cat ttt cgt gaa    480
Lys Gly Val Gly Tyr Val Ala Lys His Ala Gly Arg His Phe Arg Glu
145                 150                 155                 160 cgt ttc gaa aaa gaa ggc aaa aag ggc gcc ttg gtt ttt acg gct tcc    528
Arg Phe Glu Lys Glu Gly Lys Lys Gly Ala Leu Val Phe Thr Ala Ser
                165                 170                 175 atg tcg ggt cac atc gtt aac gtg ccg caa ttt cag gcg acc tac aat    576
Met Ser Gly His Ile Val Asn Val Pro Gln Phe Gln Ala Thr Tyr Asn
            180                 185                 190 gcg gcc aag gca ggc gtg cgt cat ttc gca aag tcc ctg gcc gtg gaa    624
Ala Ala Lys Ala Gly Val Arg His Phe Ala Lys Ser Leu Ala Val Glu
        195                 200                 205 ttt gct cct ttc gca cgt gtt aac tct gta tct cct ggc tat att aat    672
Phe Ala Pro Phe Ala Arg Val Asn Ser Val Ser Pro Gly Tyr Ile Asn
    210                 215                 220 acc gag atc tct gat ttc gtc ccg caa gaa aca caa aat aaa tgg tgg    720
Thr Glu Ile Ser Asp Phe Val Pro Gln Glu Thr Gln Asn Lys Trp Trp
```

```
Thr Glu Ile Ser Asp Phe Val Pro Gln Glu Thr Gln Asn Lys Trp Trp
225                 230                 235                 240 agc tta gtt cca ttg ggc cgt ggt ggg gaa act gcg gaa tta gtt ggt    768
Ser Leu Val Pro Leu Gly Arg Gly Gly Glu Thr Ala Glu Leu Val Gly
                245                 250                 255 gcc tac ctg ttc ctg gca agt gat gcg ggc tcc tac gcc acg ggc aca    816
Ala Tyr Leu Phe Leu Ala Ser Asp Ala Gly Ser Tyr Ala Thr Gly Thr
                260                 265                 270 gat atc att gtg gac ggc ggc tac acg ctg ccg taa tga                855
Asp Ile Ile Val Asp Gly Gly Tyr Thr Leu Pro *   *
                275                 280
```

<210> SEQ ID NO 48
<211> LENGTH: 283
<212> TYPE: PRT
<213> ORGANISM: Artificial Sequence
<220> FEATURE:
<223> OTHER INFORMATION: KRED krh320

<400> SEQUENCE: 48

```
Met Ala Lys Asn Phe Ser Asn Val Glu Tyr Pro Ala Pro Pro Pro Ala
1               5                   10                  15

His Thr Lys Asn Glu Ser Leu Gln Val Leu Asp Leu Phe Lys Leu Asn
                20                  25                  30

Gly Lys Val Ala Ser Ile Thr Gly Ser Asn Ser Gly Ile Gly Tyr Ala
            35                  40                  45

Leu Ala Glu Ala Phe Ala Gln Val Gly Ala Asp Val Ala Ile Trp Tyr
50                  55                  60

Asn Ser His Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Ser Tyr Ala
                85                  90                  95

Val Lys Gln Thr Ile Glu Gln Ile Lys Asp Phe Gly His Leu Asp
                100                 105                 110

Ile Val Val Ala Asn Ala Gly Ile Pro Trp Thr Lys Gly Ala Tyr Ile
            115                 120                 125

Asp Gln Asp Asp Asp Lys His Phe Asp Gln Val Val Asp Val Asp Leu
130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Ala Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
            275                 280
```

-continued

```
<210> SEQ ID NO 49
<211> LENGTH: 852
<212> TYPE: DNA
<213> ORGANISM: Artificial Sequence
<220> FEATURE:
<223> OTHER INFORMATION: KRED krh326
<220> FEATURE:
<221> NAME/KEY: CDS
<222> LOCATION: (1)...(852)

<400> SEQUENCE: 49 atg gct aaa aac ttt agc aat gtc gaa tac cct gcc ccg ccg cca gct       48
Met Ala Lys Asn Phe Ser Asn Val Glu Tyr Pro Ala Pro Pro Pro Ala
 1               5                  10                  15 cat acc aaa aac gaa tca ctg cag gta ctg gat ctg ttc aaa ctg aac       96
His Thr Lys Asn Glu Ser Leu Gln Val Leu Asp Leu Phe Lys Leu Asn
             20                  25                  30 ggc aaa gtc gcg tct atc acc ggt agc aac tca ggc att ggt tac gcg      144
Gly Lys Val Ala Ser Ile Thr Gly Ser Asn Ser Gly Ile Gly Tyr Ala
         35                  40                  45 ctg gcc gaa gct ttt gcg cag gtt ggc gca gac gtt gcg atc tgg tat      192
Leu Ala Glu Ala Phe Ala Gln Val Gly Ala Asp Val Ala Ile Trp Tyr
     50                  55                  60 aac agc cat gat gcc acc ggt aaa gca gag gcc ctg gct aaa aaa tat      240
Asn Ser His Asp Ala Thr Gly Lys Ala Glu Ala Leu Ala Lys Lys Tyr
 65                  70                  75                  80 ggc gta aaa gtc aag gct tat aaa gct aat gtc agc tcg agt gat gcg      288
Gly Val Lys Val Lys Ala Tyr Lys Ala Asn Val Ser Ser Ser Asp Ala
                 85                  90                  95 gtg aaa cag act att gag cag cag atc aag gat ttt ggc cac ctg gac      336
Val Lys Gln Thr Ile Glu Gln Gln Ile Lys Asp Phe Gly His Leu Asp
            100                 105                 110 att gtt gtg gcg aac gca ggc atc cca tgg act aag ggt gca tac atc      384
Ile Val Val Ala Asn Ala Gly Ile Pro Trp Thr Lys Gly Ala Tyr Ile
        115                 120                 125 gat cag gat gac gat aaa cat ttt gac cag gtg gtg gac gtc gac ctg      432
Asp Gln Asp Asp Asp Lys His Phe Asp Gln Val Val Asp Val Asp Leu
    130                 135                 140 aaa ggc gta ggc tat gta gca aaa cat gcg ggt cgc cat ttt cgt gaa      480
Lys Gly Val Gly Tyr Val Ala Lys His Ala Gly Arg His Phe Arg Glu
145                 150                 155                 160 cgt ttc gaa aaa gaa ggc aaa aag ggc gcc ttg gtt ttt acg gct tcc      528
Arg Phe Glu Lys Glu Gly Lys Lys Gly Ala Leu Val Phe Thr Ala Ser
                165                 170                 175 atg tcg ggt cac atc gtt aac gtg ccg caa ttt cag gcg acc tac aat      576
Met Ser Gly His Ile Val Asn Val Pro Gln Phe Gln Ala Thr Tyr Asn
            180                 185                 190 gcg gtc aag gca ggc gtg cgt cac ttc gca aag tcc ctg gcc gtg gaa      624
Ala Val Lys Ala Gly Val Arg His Phe Ala Lys Ser Leu Ala Val Glu
        195                 200                 205 ttt gct cct ttc gca cgt gtt aac tct gta tct cct ggc tat att aat      672
Phe Ala Pro Phe Ala Arg Val Asn Ser Val Ser Pro Gly Tyr Ile Asn
    210                 215                 220 acc gag atc tct gat ttc gtc ccg caa gaa aca caa aat aaa tgg tgg      720
Thr Glu Ile Ser Asp Phe Val Pro Gln Glu Thr Gln Asn Lys Trp Trp
225                 230                 235                 240 agc tta gtt cca ttg ggt cgt ggt ggg gaa act gcg gaa tta gtt ggt      768
Ser Leu Val Pro Leu Gly Arg Gly Gly Glu Thr Ala Glu Leu Val Gly
                245                 250                 255 gcc tac ctg ttc ctg gca agt gat gcg ggc tcc tac gcc acg ggc aca      816
Ala Tyr Leu Phe Leu Ala Ser Asp Ala Gly Ser Tyr Ala Thr Gly Thr
```

```
             260                 265                 270
gat atc att gtg gac ggc ggc tac acg ctg ccg taa                        852
Asp Ile Ile Val Asp Gly Gly Tyr Thr Leu Pro *
        275                 280
```

<210> SEQ ID NO 50
<211> LENGTH: 283
<212> TYPE: PRT
<213> ORGANISM: Artificial Sequence
<220> FEATURE:
<223> OTHER INFORMATION: KRED krh326

<400> SEQUENCE: 50

```
Met Ala Lys Asn Phe Ser Asn Val Glu Tyr Pro Ala Pro Pro Ala
1               5                   10                  15

His Thr Lys Asn Glu Ser Leu Gln Val Leu Asp Leu Phe Lys Leu Asn
            20                  25                  30

Gly Lys Val Ala Ser Ile Thr Gly Ser Asn Ser Gly Ile Gly Tyr Ala
        35                  40                  45

Leu Ala Glu Ala Phe Ala Gln Val Gly Ala Asp Val Ala Ile Trp Tyr
50                  55                  60

Asn Ser His Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Ser Asp Ala
                85                  90                  95

Val Lys Gln Thr Ile Glu Gln Gln Ile Lys Asp Phe Gly His Leu Asp
            100                 105                 110

Ile Val Val Ala Asn Ala Gly Ile Pro Trp Thr Lys Gly Ala Tyr Ile
        115                 120                 125

Asp Gln Asp Asp Asp Lys His Phe Asp Gln Val Val Asp Val Asp Leu
130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Val Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
        275                 280
```

<210> SEQ ID NO 51
<211> LENGTH: 852
<212> TYPE: DNA
<213> ORGANISM: Artificial Sequence
<220> FEATURE:
<223> OTHER INFORMATION: KRED krh408
<220> FEATURE:
<221> NAME/KEY: CDS -continued

<222> LOCATION: (1)...(852)

<400> SEQUENCE: 51

```
atg gct aaa aac ttt agc aat gtc gaa tac cct gcc ccg ccg cca gct    48
Met Ala Lys Asn Phe Ser Asn Val Glu Tyr Pro Ala Pro Pro Pro Ala
1               5                  10                  15 cat acc aaa aac gaa tca ctg cag gta ctg gat ctg ttc aaa ctg aac    96
His Thr Lys Asn Glu Ser Leu Gln Val Leu Asp Leu Phe Lys Leu Asn
            20                  25                  30 ggc aaa gtc gcg tct atc acc ggt agc aac tca ggc att ggt tac gcg   144
Gly Lys Val Ala Ser Ile Thr Gly Ser Asn Ser Gly Ile Gly Tyr Ala
        35                  40                  45 ctg gcc gaa gct ttt gcg cag gct ggc gca gac gtt gcg atc tgg tat   192
Leu Ala Glu Ala Phe Ala Gln Ala Gly Ala Asp Val Ala Ile Trp Tyr
    50                  55                  60 aac agc cat gat gcc acc ggt aaa gca gag gcc ctg gct aaa aaa tat   240
Asn Ser His Asp Ala Thr Gly Lys Ala Glu Ala Leu Ala Lys Lys Tyr
65                  70                  75                  80 ggc gta aaa gtc aag gct tat aaa gct aat gtc agc tcg agt gat gcg   288
Gly Val Lys Val Lys Ala Tyr Lys Ala Asn Val Ser Ser Ser Asp Ala
                85                  90                  95 gtg aaa cag act att gag cag cag atc aag gat ttt ggc cac ctg gac   336
Val Lys Gln Thr Ile Glu Gln Gln Ile Lys Asp Phe Gly His Leu Asp
            100                 105                 110 att gtt gtg gcg aac gca ggc atc cca tgg act aag ggt gca tac atc   384
Ile Val Val Ala Asn Ala Gly Ile Pro Trp Thr Lys Gly Ala Tyr Ile
        115                 120                 125 gat cag gat gac gat aaa cat ttt gac cag gtg gtg gac gtc gac ctg   432
Asp Gln Asp Asp Asp Lys His Phe Asp Gln Val Val Asp Val Asp Leu
    130                 135                 140 aaa ggc gta ggc tat gta gca aaa cat gcg ggt cgc cat ttt cgt gaa   480
Lys Gly Val Gly Tyr Val Ala Lys His Ala Gly Arg His Phe Arg Glu
145                 150                 155                 160 cgt tcc gaa aaa gaa ggc aaa aag ggc gcc ttg gtt ttt acg gct tcc   528
Arg Ser Glu Lys Glu Gly Lys Lys Gly Ala Leu Val Phe Thr Ala Ser
                165                 170                 175 atg tcg ggt cac atc gtt aac gtg ccg caa ttt cag gcg acc tac aac   576
Met Ser Gly His Ile Val Asn Val Pro Gln Phe Gln Ala Thr Tyr Asn
            180                 185                 190 gcg gtc aag gca ggc gtg cgt cat ttc gca aag tcc ctg gcc gtg gaa   624
Ala Val Lys Ala Gly Val Arg His Phe Ala Lys Ser Leu Ala Val Glu
        195                 200                 205 ttt gct cct ttc gca cgt gtt aac tct gta tct cct ggc tat att aat   672
Phe Ala Pro Phe Ala Arg Val Asn Ser Val Ser Pro Gly Tyr Ile Asn
    210                 215                 220 acc gag atc tct gat ttc gtc ccg caa gaa aca caa aat aaa tgg tgg   720
Thr Glu Ile Ser Asp Phe Val Pro Gln Glu Thr Gln Asn Lys Trp Trp
225                 230                 235                 240 agc tta gtt cca ttg ggt cgt ggt ggg gaa act gcg gaa tta gtt ggt   768
Ser Leu Val Pro Leu Gly Arg Gly Gly Glu Thr Ala Glu Leu Val Gly
                245                 250                 255 gcc tac ctg ttc ctg gca agt gat gcg ggc tcc tac gcc acg ggc aca   816
Ala Tyr Leu Phe Leu Ala Ser Asp Ala Gly Ser Tyr Ala Thr Gly Thr
            260                 265                 270 gat atc att gtg gac ggc ggc tac acg ctg ccg taa                   852
Asp Ile Ile Val Asp Gly Gly Tyr Thr Leu Pro *
        275                 280
```

<210> SEQ ID NO 52
<211> LENGTH: 283

```
<212> TYPE: PRT
<213> ORGANISM: Artificial Sequence
<220> FEATURE:
<223> OTHER INFORMATION: KRED krh408

<400> SEQUENCE: 52

Met Ala Lys Asn Phe Ser Asn Val Glu Tyr Pro Ala Pro Pro Pro Ala
1               5                   10                  15

His Thr Lys Asn Glu Ser Leu Gln Val Leu Asp Leu Phe Lys Leu Asn
            20                  25                  30

Gly Lys Val Ala Ser Ile Thr Gly Ser Asn Ser Gly Ile Gly Tyr Ala
        35                  40                  45

Leu Ala Glu Ala Phe Ala Gln Ala Gly Ala Asp Val Ala Ile Trp Tyr
    50                  55                  60

Asn Ser His Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Ser Asp Ala
                85                  90                  95

Val Lys Gln Thr Ile Glu Gln Gln Ile Lys Asp Phe Gly His Leu Asp
            100                 105                 110

Ile Val Val Ala Asn Ala Gly Ile Pro Trp Thr Lys Gly Ala Tyr Ile
        115                 120                 125

Asp Gln Asp Asp Asp Lys His Phe Asp Gln Val Asp Val Asp Leu
    130                 135                 140

Lys Gly Val Gly Tyr Val Ala Lys His Ala Gly Arg His Phe Arg Glu
145                 150                 155                 160

Arg Ser Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Val Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
    210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
        275                 280

<210> SEQ ID NO 53
<211> LENGTH: 852
<212> TYPE: DNA
<213> ORGANISM: Artificial Sequence
<220> FEATURE:
<223> OTHER INFORMATION: KRED krh417
<220> FEATURE:
<221> NAME/KEY: CDS
<222> LOCATION: (1)...(852)

<400> SEQUENCE: 53 atg gct aaa aac ttt agc aat gtc gaa tat cct gcc ccg ccg cca gct    48
Met Ala Lys Asn Phe Ser Asn Val Glu Tyr Pro Ala Pro Pro Pro Ala
1               5                   10                  15 cat acc aaa aac gaa tca ctg cag gta ctg gat ctg ttc aaa ctg aac    96
```

|     |     |     |     |     |     |     |     |     |     |     |     |     |     |     | |
|-----|-----|-----|-----|-----|-----|-----|-----|-----|-----|-----|-----|-----|-----|-----|---|
| His | Thr | Lys | Asn | Glu | Ser | Leu | Gln | Val | Leu | Asp | Leu | Phe | Lys | Leu | Asn |
|     |     |     | 20  |     |     |     |     | 25  |     |     |     |     | 30  |     |   |

```
ggc aaa gtc gcg tct atc acc ggt agc aac tca ggc att ggt tac gcg        144
Gly Lys Val Ala Ser Ile Thr Gly Ser Asn Ser Gly Ile Gly Tyr Ala
         35                  40                  45 ctg gcc gaa gct ttt gcg cag gtt ggc gca gac gtt gcg atc tgg tat        192
Leu Ala Glu Ala Phe Ala Gln Val Gly Ala Asp Val Ala Ile Trp Tyr
     50                  55                  60 aac agc cat gat gcc acc ggt aaa gca gag gcc ctg gct aaa aaa tat        240
Asn Ser His Asp Ala Thr Gly Lys Ala Glu Ala Leu Ala Lys Lys Tyr
 65                  70                  75                  80 ggc gta aaa gtc aag gct tat aaa gct aat gtc agc tcg agt gat gcg        288
Gly Val Lys Val Lys Ala Tyr Lys Ala Asn Val Ser Ser Ser Asp Ala
                 85                  90                  95 gtg aaa cag act att gag cag cag atc aag gat ttt ggc cac ctg gac        336
Val Lys Gln Thr Ile Glu Gln Gln Ile Lys Asp Phe Gly His Leu Asp
             100                 105                 110 att gtt gtg gcg aac gca ggc atc cca tgg act aag ggt gca tac atc        384
Ile Val Val Ala Asn Ala Gly Ile Pro Trp Thr Lys Gly Ala Tyr Ile
         115                 120                 125 gat cag gat gac gat aaa cat ttt gac cag gtg gtg gac gtc gac ctg        432
Asp Gln Asp Asp Asp Lys His Phe Asp Gln Val Val Asp Val Asp Leu
     130                 135                 140 aaa ggc gta ggc tat gta gca aaa cat gcg ggt cgc cat ttt cgt gaa        480
Lys Gly Val Gly Tyr Val Ala Lys His Ala Gly Arg His Phe Arg Glu
145                 150                 155                 160 cgt ttc gaa aaa gaa ggc aaa aag ggc gcc ttg gtt ttt acg gct tcc        528
Arg Phe Glu Lys Glu Gly Lys Lys Gly Ala Leu Val Phe Thr Ala Ser
                 165                 170                 175 atg tcg ggt cac atc gtt aac att ccg caa ttt cag gcg acc tac aat        576
Met Ser Gly His Ile Val Asn Ile Pro Gln Phe Gln Ala Thr Tyr Asn
             180                 185                 190 gcg gcc aag gca ggc gtg cgt cat ttc gca aag tcc ctg gcc gtg gaa        624
Ala Ala Lys Ala Gly Val Arg His Phe Ala Lys Ser Leu Ala Val Glu
         195                 200                 205 ttt gct cct ttc gca cgt gtt aac tct gta tct cct ggc tat att aat        672
Phe Ala Pro Phe Ala Arg Val Asn Ser Val Ser Pro Gly Tyr Ile Asn
     210                 215                 220 acc gag atc tct gat ttc gtc ccg caa gaa aca caa aat aaa tgg tgg        720
Thr Glu Ile Ser Asp Phe Val Pro Gln Glu Thr Gln Asn Lys Trp Trp
225                 230                 235                 240 agc tta gtc cca ttg ggt cgt ggt ggg gaa act gcg gaa tta gtt ggt        768
Ser Leu Val Pro Leu Gly Arg Gly Gly Glu Thr Ala Glu Leu Val Gly
                 245                 250                 255 gcc tac ctg ttc ctg gca agt gat gcg ggc tcc tac gcc acg ggc aca        816
Ala Tyr Leu Phe Leu Ala Ser Asp Ala Gly Ser Tyr Ala Thr Gly Thr
             260                 265                 270 gat atc att gtg gat ggc ggc tac acg ctg ccg taa                        852
Asp Ile Ile Val Asp Gly Gly Tyr Thr Leu Pro *
         275                 280

<210> SEQ ID NO 54
<211> LENGTH: 283
<212> TYPE: PRT
<213> ORGANISM: Artificial Sequence
<220> FEATURE:
<223> OTHER INFORMATION: KRED krh417

<400> SEQUENCE: 54

Met Ala Lys Asn Phe Ser Asn Val Glu Tyr Pro Ala Pro Pro Ala
  1               5                  10                  15
```

-continued

```
His Thr Lys Asn Glu Ser Leu Gln Val Leu Asp Leu Phe Lys Leu Asn
         20                  25                  30

Gly Lys Val Ala Ser Ile Thr Gly Ser Asn Ser Gly Ile Gly Tyr Ala
     35                  40                  45

Leu Ala Glu Ala Phe Ala Gln Val Gly Ala Asp Val Ala Ile Trp Tyr
 50                  55                  60

Asn Ser His Asp Ala Thr Gly Lys Ala Glu Ala Leu Ala Lys Lys Tyr
 65                  70                  75                  80

Gly Val Lys Val Lys Ala Tyr Lys Ala Asn Val Ser Ser Ser Asp Ala
                 85                  90                  95

Val Lys Gln Thr Ile Glu Gln Gln Ile Lys Asp Phe Gly His Leu Asp
            100                 105                 110

Ile Val Ala Asn Ala Gly Ile Pro Trp Thr Lys Gly Ala Tyr Ile
            115                 120                 125

Asp Gln Asp Asp Asp Lys His Phe Asp Gln Val Asp Val Asp Leu
        130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Ile Pro Gln Phe Gln Ala Thr Tyr Asn
            180                 185                 190

Ala Ala Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
    210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
        275                 280
```

```
<210> SEQ ID NO 55
<211> LENGTH: 852
<212> TYPE: DNA
<213> ORGANISM: Artificial Sequence
<220> FEATURE:
<223> OTHER INFORMATION: KRED krh483
<220> FEATURE:
<221> NAME/KEY: CDS
<222> LOCATION: (1)...(852)

<400> SEQUENCE: 55
```

```
atg gct aaa aac ttt tcc aat gtc gaa tat cct gcc ccg ccg cca gct      48
Met Ala Lys Asn Phe Ser Asn Val Glu Tyr Pro Ala Pro Pro Pro Ala
 1               5                  10                  15 cat acc aaa aac gaa tca ctg cag gta ctg gat ctg ttc aaa ctg aac      96
His Thr Lys Asn Glu Ser Leu Gln Val Leu Asp Leu Phe Lys Leu Asn
             20                  25                  30 ggc aaa gtc gcg tct atc acc ggt agc aac tca ggc att ggt tac gcg     144
Gly Lys Val Ala Ser Ile Thr Gly Ser Asn Ser Gly Ile Gly Tyr Ala
         35                  40                  45 ctg gcc gaa gct ttt gcg cag gtt ggc gca gac gtt gcg atc tgg tat     192
Leu Ala Glu Ala Phe Ala Gln Val Gly Ala Asp Val Ala Ile Trp Tyr
     50                  55                  60
```

```
                50                      55                      60
aac  agc  cat  gat  gcc  acc  ggt  aaa  gca  gag  gcc  ctg  gct  aaa  aaa  tat      240
Asn  Ser  His  Asp  Ala  Thr  Gly  Lys  Ala  Glu  Ala  Leu  Ala  Lys  Lys  Tyr
 65                      70                      75                      80 ggc  gta  aaa  gtc  aag  gct  tat  aaa  gct  aat  gtc  agc  tcg  agt  gat  gcg      288
Gly  Val  Lys  Val  Lys  Ala  Tyr  Lys  Ala  Asn  Val  Ser  Ser  Ser  Asp  Ala
                         85                      90                      95 gtg  aaa  cag  act  att  gag  cag  cag  atc  aag  gat  ttt  ggc  cac  ctg  gac      336
Val  Lys  Gln  Thr  Ile  Glu  Gln  Gln  Ile  Lys  Asp  Phe  Gly  His  Leu  Asp
100                     105                     110 ata  gtt  gtg  gcg  aac  gca  ggc  atc  cca  tgg  act  aag  ggt  gca  tac  atc      384
Ile  Val  Val  Ala  Asn  Ala  Gly  Ile  Pro  Trp  Thr  Lys  Gly  Ala  Tyr  Ile
               115                     120                     125 gat  cag  gat  gac  gat  aaa  cat  ttt  gac  cag  gtg  gtg  gac  gtc  gac  ctg      432
Asp  Gln  Asp  Asp  Asp  Lys  His  Phe  Asp  Gln  Val  Val  Asp  Val  Asp  Leu
130                     135                     140 aaa  ggc  gta  ggc  tat  gta  gca  aaa  cat  gcg  ggt  cgc  cat  ttt  cgt  gaa      480
Lys  Gly  Val  Gly  Tyr  Val  Ala  Lys  His  Ala  Gly  Arg  His  Phe  Arg  Glu
145                     150                     155                     160 cgt  ttc  gaa  aaa  gaa  ggc  aaa  aag  ggc  gcc  ttg  gtt  ttt  acg  gct  tcc      528
Arg  Phe  Glu  Lys  Glu  Gly  Lys  Lys  Gly  Ala  Leu  Val  Phe  Thr  Ala  Ser
                        165                     170                     175 atg  tcg  ggt  cac  atc  gtt  aac  gtg  ccg  caa  ttt  cag  gcg  acc  tac  aat      576
Met  Ser  Gly  His  Ile  Val  Asn  Val  Pro  Gln  Phe  Gln  Ala  Thr  Tyr  Asn
               180                     185                     190 gcg  gtc  aag  gca  ggc  gtg  cgt  cat  ttc  gca  aag  tcc  ctg  gcc  gtg  gaa      624
Ala  Val  Lys  Ala  Gly  Val  Arg  His  Phe  Ala  Lys  Ser  Leu  Ala  Val  Glu
195                     200                     205 ttt  gct  cct  ttc  gca  cgt  gtt  aac  tct  gta  tct  cct  ggc  tat  att  aat      672
Phe  Ala  Pro  Phe  Ala  Arg  Val  Asn  Ser  Val  Ser  Pro  Gly  Tyr  Ile  Asn
210                     215                     220 acc  gag  atc  tct  gat  ttc  gtc  ccg  caa  gaa  aca  caa  aat  aaa  tgg  tgg      720
Thr  Glu  Ile  Ser  Asp  Phe  Val  Pro  Gln  Glu  Thr  Gln  Asn  Lys  Trp  Trp
225                     230                     235                     240 agc  tta  gtt  cca  ttg  ggc  cgt  ggc  ggg  gaa  act  gcg  gaa  tta  gtt  ggt      768
Ser  Leu  Val  Pro  Leu  Gly  Arg  Gly  Gly  Glu  Thr  Ala  Glu  Leu  Val  Gly
                        245                     250                     255 gcc  tac  ctg  ttc  ctg  gca  agt  gat  gcg  ggc  tcc  tac  gcc  acg  ggc  aca      816
Ala  Tyr  Leu  Phe  Leu  Ala  Ser  Asp  Ala  Gly  Ser  Tyr  Ala  Thr  Gly  Thr
               260                     265                     270 gat  atc  att  gtg  gac  ggc  ggc  tac  acg  ctg  ccg  taa                           852
Asp  Ile  Ile  Val  Asp  Gly  Gly  Tyr  Thr  Leu  Pro   *
               275                     280

<210> SEQ ID NO 56
<211> LENGTH: 283
<212> TYPE: PRT
<213> ORGANISM: Artificial Sequence
<220> FEATURE:
<223> OTHER INFORMATION: KRED krh483

<400> SEQUENCE: 56

Met  Ala  Lys  Asn  Phe  Ser  Asn  Val  Glu  Tyr  Pro  Ala  Pro  Pro  Ala
 1                 5                      10                      15

His  Thr  Lys  Asn  Glu  Ser  Leu  Gln  Val  Leu  Asp  Leu  Phe  Lys  Leu  Asn
                    20                      25                      30

Gly  Lys  Val  Ala  Ser  Ile  Thr  Gly  Ser  Asn  Ser  Gly  Ile  Gly  Tyr  Ala
           35                      40                      45

Leu  Ala  Glu  Ala  Phe  Ala  Gln  Val  Gly  Ala  Asp  Val  Ala  Ile  Trp  Tyr
 50                     55                      60
```

```
Asn Ser His Asp Ala Thr Gly Lys Ala Glu Ala Leu Ala Lys Lys Tyr
 65                  70                  75                  80

Gly Val Lys Val Lys Ala Tyr Lys Ala Asn Val Ser Ser Ser Asp Ala
                 85                  90                  95

Val Lys Gln Thr Ile Glu Gln Ile Lys Asp Phe Gly His Leu Asp
            100                 105                 110

Ile Val Val Ala Asn Ala Gly Ile Pro Trp Thr Lys Gly Ala Tyr Ile
            115                 120                 125

Asp Gln Asp Asp Asp Lys His Phe Asp Gln Val Asp Val Asp Leu
130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Val Lys Ala Gly Val Arg His Phe Ala Lys Ser Leu Ala Val Glu
            195                 200                 205

Phe Ala Pro Phe Ala Arg Val Asn Ser Val Ser Pro Gly Tyr Ile Asn
210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
            275                 280

<210> SEQ ID NO 57
<211> LENGTH: 852
<212> TYPE: DNA
<213> ORGANISM: Artificial Sequence
<220> FEATURE:
<223> OTHER INFORMATION: KRED krh476
<220> FEATURE:
<221> NAME/KEY: CDS
<222> LOCATION: (1)...(852)

<400> SEQUENCE: 57 atg gct aaa aac ttt tcc aat gtc gaa tat cct gcc ccg ccg cca gct    48
Met Ala Lys Asn Phe Ser Asn Val Glu Tyr Pro Ala Pro Pro Pro Ala
  1               5                  10                  15 cat acc aaa gac gaa tca ctg cag gta ctg gat ctg ttc aaa ctg aac    96
His Thr Lys Asp Glu Ser Leu Gln Val Leu Asp Leu Phe Lys Leu Asn
             20                  25                  30 ggc aaa gtc gcg tct atc acc ggt agc aac tca ggc att ggt tac gcg   144
Gly Lys Val Ala Ser Ile Thr Gly Ser Asn Ser Gly Ile Gly Tyr Ala
         35                  40                  45 ctg gcc gaa gct ttt gcg cag gtt ggc gca gac gtt gcg atc tgg tat   192
Leu Ala Glu Ala Phe Ala Gln Val Gly Ala Asp Val Ala Ile Trp Tyr
     50                  55                  60 aac agc cat gat gcc acc ggt aaa gca gag gcc ctg gct aaa aaa tat   240
Asn Ser His Asp Ala Thr Gly Lys Ala Glu Ala Leu Ala Lys Lys Tyr
 65                  70                  75                  80 ggc gta aaa gtc aag gct tat aaa gct aat gtc agc tcg agt gat gcg   288
Gly Val Lys Val Lys Ala Tyr Lys Ala Asn Val Ser Ser Ser Asp Ala
                 85                  90                  95
```

```
gtg aaa cag act att gag cag cag atc aag gat ttt ggc cac ctg gac    336
Val Lys Gln Thr Ile Glu Gln Gln Ile Lys Asp Phe Gly His Leu Asp
            100                 105                 110 att gtt gtg gcg aac gca ggc atc cca tgg act aag ggt gca tac atc    384
Ile Val Val Ala Asn Ala Gly Ile Pro Trp Thr Lys Gly Ala Tyr Ile
            115                 120                 125 gat cag gat gac gat aaa cat ttt gac cag gtg gtg gac gtc gac ctg    432
Asp Gln Asp Asp Asp Lys His Phe Asp Gln Val Val Asp Val Asp Leu
        130                 135                 140 aaa ggc gta ggc tat gta gcg aaa cat gcg ggt cgc cat ttt cgt gaa    480
Lys Gly Val Gly Tyr Val Ala Lys His Ala Gly Arg His Phe Arg Glu
145                 150                 155                 160 cgt ttc gaa aaa gaa ggc aaa aag ggc gcc ttg gtt ttt acg gct tcc    528
Arg Phe Glu Lys Glu Gly Lys Lys Gly Ala Leu Val Phe Thr Ala Ser
                165                 170                 175 atg tcg ggt cac atc gtt aac gtg ccg caa ttt cag gcg acc tac aat    576
Met Ser Gly His Ile Val Asn Val Pro Gln Phe Gln Ala Thr Tyr Asn
            180                 185                 190 gcg gtc aag gca ggc gtg cgt cat ttc gca aag tcc ctg gcc gtg gaa    624
Ala Val Lys Ala Gly Val Arg His Phe Ala Lys Ser Leu Ala Val Glu
        195                 200                 205 ttt gct cct ttc gca cgt gtt aac tct gta tct cct ggc tat att aat    672
Phe Ala Pro Phe Ala Arg Val Asn Ser Val Ser Pro Gly Tyr Ile Asn
    210                 215                 220 acc gag atc tct gat ttc gtc ccg caa gaa aca cag aat aaa tgg tgg    720
Thr Glu Ile Ser Asp Phe Val Pro Gln Glu Thr Gln Asn Lys Trp Trp
225                 230                 235                 240 agc tta gtt cca ttg ggc cgt ggt ggg gaa act gcg gaa tta gtt ggt    768
Ser Leu Val Pro Leu Gly Arg Gly Gly Glu Thr Ala Glu Leu Val Gly
                245                 250                 255 gcc tac ctg ttc ctg gca agt gat gcg ggc tcc tac gcc acg ggc aca    816
Ala Tyr Leu Phe Leu Ala Ser Asp Ala Gly Ser Tyr Ala Thr Gly Thr
            260                 265                 270 gat atc att gtg gac ggc ggc tac acg ctg ccg taa                    852
Asp Ile Ile Val Asp Gly Gly Tyr Thr Leu Pro *
        275                 280
```

<210> SEQ ID NO 58
<211> LENGTH: 283
<212> TYPE: PRT
<213> ORGANISM: Artificial Sequence
<220> FEATURE:
<223> OTHER INFORMATION: KRED krh476

<400> SEQUENCE: 58

```
Met Ala Lys Asn Phe Ser Asn Val Glu Tyr Pro Ala Pro Pro Pro Ala
1               5                   10                  15

His Thr Lys Asp Glu Ser Leu Gln Val Leu Asp Leu Phe Lys Leu Asn
            20                  25                  30

Gly Lys Val Ala Ser Ile Thr Gly Ser Asn Ser Gly Ile Gly Tyr Ala
        35                  40                  45

Leu Ala Glu Ala Phe Ala Gln Val Gly Ala Asp Val Ala Ile Trp Tyr
    50                  55                  60

Asn Ser His Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Ser Asp Ala
                85                  90                  95

Val Lys Gln Thr Ile Glu Gln Gln Ile Lys Asp Phe Gly His Leu Asp
            100                 105                 110
```

```
Ile Val Val Ala Asn Ala Gly Ile Pro Trp Thr Lys Gly Ala Tyr Ile
            115                 120                 125

Asp Gln Asp Asp Lys His Phe Asp Gln Val Val Asp Val Asp Leu
130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Val Lys Ala Gly Val Arg His Phe Ala Lys Ser Leu Ala Val Glu
            195                 200                 205

Phe Ala Pro Phe Ala Arg Val Asn Ser Val Ser Pro Gly Tyr Ile Asn
            210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
            275                 280

<210> SEQ ID NO 59
<211> LENGTH: 852
<212> TYPE: DNA
<213> ORGANISM: Artificial Sequence
<220> FEATURE:
<223> OTHER INFORMATION: KRED krh495
<220> FEATURE:
<221> NAME/KEY: CDS
<222> LOCATION: (1)...(852)

<400> SEQUENCE: 59 atg gct aaa aac ttt tcc aat gtc gaa tat cct gcc ccg ccg cca gct      48
Met Ala Lys Asn Phe Ser Asn Val Glu Tyr Pro Ala Pro Pro Pro Ala
 1               5                  10                  15 cat acc aaa gac gaa tca ctg cag gta ctg gat ctg ttc aaa ctg aac      96
His Thr Lys Asp Glu Ser Leu Gln Val Leu Asp Leu Phe Lys Leu Asn
                20                  25                  30 ggc aaa gtc gcg tct atc acc ggt agc agc tca ggc att ggt tac gcg     144
Gly Lys Val Ala Ser Ile Thr Gly Ser Ser Ser Gly Ile Gly Tyr Ala
            35                  40                  45 ctg gcc gaa gcc ttt gcg cag gtt ggc gca gac gtt gcg atc tgg tat     192
Leu Ala Glu Ala Phe Ala Gln Val Gly Ala Asp Val Ala Ile Trp Tyr
        50                  55                  60 aac agc cag gat gcc acc ggt aaa gca gag gcc ctg gct aaa aaa tat     240
Asn Ser Gln Asp Ala Thr Gly Lys Ala Glu Ala Leu Ala Lys Lys Tyr
 65                  70                  75                  80 ggc gta aaa gtc aag gct tat aaa gct aat gtc agc tcg agt gat gcg     288
Gly Val Lys Val Lys Ala Tyr Lys Ala Asn Val Ser Ser Ser Asp Ala
                 85                  90                  95 gtg aaa cag act att gag cag cag atc aag gat ttt ggc cac ctg gac     336
Val Lys Gln Thr Ile Glu Gln Gln Ile Lys Asp Phe Gly His Leu Asp
            100                 105                 110 att gtt gtg gcg aac gca ggc atc cca tgg act aag ggt gca tac atc     384
Ile Val Val Ala Asn Ala Gly Ile Pro Trp Thr Lys Gly Ala Tyr Ile
        115                 120                 125
```

```
gat cag gat gac gat aaa cat ttt gac cag gtg att gac gtc gac ctg         432
Asp Gln Asp Asp Asp Lys His Phe Asp Gln Val Ile Asp Val Asp Leu
        130                 135                 140 aaa ggc gta ggc tat gta gca aaa cat gcg ggt cgc cat tat cgt gaa         480
Lys Gly Val Gly Tyr Val Ala Lys His Ala Gly Arg His Tyr Arg Glu
145                 150                 155                 160 cgt ttc gaa aaa gaa ggc ata aag ggc gcc ttg att ttt acg gct tcc         528
Arg Phe Glu Lys Glu Gly Ile Lys Gly Ala Leu Ile Phe Thr Ala Ser
                165                 170                 175 gtg tcg ggt cac atc gtt aac att ccg caa ttt cag gcg acc tac aat         576
Val Ser Gly His Ile Val Asn Ile Pro Gln Phe Gln Ala Thr Tyr Asn
            180                 185                 190 gcg gcc aag gca ggc gtg cgt cat ttc gca aag tcc ctg gcc gtg gaa         624
Ala Ala Lys Ala Gly Val Arg His Phe Ala Lys Ser Leu Ala Val Glu
        195                 200                 205 ttt gct cct ttc gca cgt gtt aac tct gta tct cct ggc tat att aat         672
Phe Ala Pro Phe Ala Arg Val Asn Ser Val Ser Pro Gly Tyr Ile Asn
    210                 215                 220 acc gag atc tct gat ttc gtc ccg caa gaa aca caa aat aaa tgg tgg         720
Thr Glu Ile Ser Asp Phe Val Pro Gln Glu Thr Gln Asn Lys Trp Trp
225                 230                 235                 240 agc tta gtt cca ttg ggt cgt ggt ggg gaa act gcg gaa tta gtt ggt         768
Ser Leu Val Pro Leu Gly Arg Gly Gly Glu Thr Ala Glu Leu Val Gly
                245                 250                 255 gcc tac ctg ttc ctg gca agt gat gcg ggc tcc tac gcc acg ggc aca         816
Ala Tyr Leu Phe Leu Ala Ser Asp Ala Gly Ser Tyr Ala Thr Gly Thr
            260                 265                 270 gat atc att gtg gat ggc ggc tac acg ctg ccg taa                         852
Asp Ile Ile Val Asp Gly Gly Tyr Thr Leu Pro *
        275                 280

<210> SEQ ID NO 60
<211> LENGTH: 283
<212> TYPE: PRT
<213> ORGANISM: Artificial Sequence
<220> FEATURE:
<223> OTHER INFORMATION: KRED krh495

<400> SEQUENCE: 60

Met Ala Lys Asn Phe Ser Asn Val Glu Tyr Pro Ala Pro Pro Ala
1               5                   10                  15

His Thr Lys Asp Glu Ser Leu Gln Val Leu Asp Leu Phe Lys Leu Asn
                20                  25                  30

Gly Lys Val Ala Ser Ile Thr Gly Ser Ser Ser Gly Ile Gly Tyr Ala
            35                  40                  45

Leu Ala Glu Ala Phe Ala Gln Val Gly Ala Asp Val Ala Ile Trp Tyr
        50                  55                  60

Asn Ser Gln Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Ser Asp Ala
                85                  90                  95

Val Lys Gln Thr Ile Glu Gln Gln Ile Lys Asp Phe Gly His Leu Asp
            100                 105                 110

Ile Val Val Ala Asn Ala Gly Ile Pro Trp Thr Lys Gly Ala Tyr Ile
        115                 120                 125

Asp Gln Asp Asp Asp Lys His Phe Asp Gln Val Ile Asp Val Asp Leu
    130                 135                 140

Lys Gly Val Gly Tyr Val Ala Lys His Ala Gly Arg His Tyr Arg Glu
145                 150                 155                 160
```

-continued

```
Arg Phe Glu Lys Glu Gly Ile Lys Gly Ala Leu Ile Phe Thr Ala Ser
                165                 170                 175
Val Ser Gly His Ile Val Asn Ile Pro Gln Phe Gln Ala Thr Tyr Asn
            180                 185                 190
Ala Ala Lys Ala Gly Val Arg His Phe Ala Lys Ser Leu Ala Val Glu
        195                 200                 205
Phe Ala Pro Phe Ala Arg Val Asn Ser Val Ser Pro Gly Tyr Ile Asn
    210                 215                 220
Thr Glu Ile Ser Asp Phe Val Pro Gln Glu Thr Gln Asn Lys Trp Trp
225                 230                 235                 240
Ser Leu Val Pro Leu Gly Arg Gly Glu Thr Ala Glu Leu Val Gly
                245                 250                 255
Ala Tyr Leu Phe Leu Ala Ser Asp Ala Gly Ser Tyr Ala Thr Gly Thr
            260                 265                 270
Asp Ile Ile Val Asp Gly Gly Tyr Thr Leu Pro
        275                 280
```

<210> SEQ ID NO 61
<211> LENGTH: 789
<212> TYPE: DNA
<213> ORGANISM: Artificial Sequence
<220> FEATURE:
<223> OTHER INFORMATION: GDH 2313
<220> FEATURE:
<221> NAME/KEY: CDS
<222> LOCATION: (1)...(789)

<400> SEQUENCE: 61

```
atg tat ccg gat tta aaa gga aaa gtc gtc gct att aca gga gct gct      48
Met Tyr Pro Asp Leu Lys Gly Lys Val Val Ala Ile Thr Gly Ala Ala
 1               5                  10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
             20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
         35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
     50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
```

```
Ser Lys Gly Gly Met Lys Leu Met Thr Glu Thr Leu Ala Leu Glu Tyr
            165                 170                 175 gcg ccg aag ggc att cgc gtc aat aat att ggg cca ggt gcg atc aac    576
Ala Pro Lys Gly Ile Arg Val Asn Asn Ile Gly Pro Gly Ala Ile Asn
            180                 185                 190 acg acg atc aat gct gag aaa ttt gct gac cct aaa cag aaa gct gat    624
Thr Thr Ile Asn Ala Glu Lys Phe Ala Asp Pro Lys Gln Lys Ala Asp
            195                 200                 205 gta gaa agc atg att cca atg gga tat atc ggc gaa ccg gag gag atc    672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                245                 250                 255 cag gca ggc cgc ggt taa tga                                        789
Gln Ala Gly Arg Gly *   *
            260
```

<210> SEQ ID NO 62
<211> LENGTH: 261
<212> TYPE: PRT
<213> ORGANISM: Artificial Sequence
<220> FEATURE:
<223> OTHER INFORMATION: GDH 2313

<400> SEQUENCE: 62

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65              70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220
```

```
Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
            245                 250                 255

Gln Ala Gly Arg Gly
        260

<210> SEQ ID NO 63
<211> LENGTH: 789
<212> TYPE: DNA
<213> ORGANISM: Artificial Sequence
<220> FEATURE:
<223> OTHER INFORMATION: GDH 2331
<220> FEATURE:
<221> NAME/KEY: CDS
<222> LOCATION: (1)...(789)

<400> SEQUENCE: 63
```

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |
| tca | ggg | ctc | gga | aag | gcg | atg | gcc | att | cgc | ttc | ggc | aag | gag | cag | gca | 96 |
| Ser | Gly | Leu | Gly | Lys | Ala | Met | Ala | Ile | Arg | Phe | Gly | Lys | Glu | Gln | Ala | |
| | | | 20 | | | | | 25 | | | | | 30 | | | |
| aaa | gtg | gtt | atc | aac | tat | tat | agt | aat | aaa | caa | gat | ccg | aac | gag | gta | 144 |
| Lys | Val | Val | Ile | Asn | Tyr | Tyr | Ser | Asn | Lys | Gln | Asp | Pro | Asn | Glu | Val | |
| | | 35 | | | | | 40 | | | | | 45 | | | | |
| aaa | gaa | gag | gtc | atc | aag | gcg | ggc | ggt | gaa | gct | gtt | gtc | gtc | caa | gga | 192 |
| Lys | Glu | Glu | Val | Ile | Lys | Ala | Gly | Gly | Glu | Ala | Val | Val | Val | Gln | Gly | |
| | 50 | | | | | 55 | | | | | 60 | | | | | |
| gat | gtc | acg | aaa | gag | gaa | gat | gta | aaa | aat | atc | gtg | caa | acg | gca | att | 240 |
| Asp | Val | Thr | Lys | Glu | Glu | Asp | Val | Lys | Asn | Ile | Val | Gln | Thr | Ala | Ile | |
| 65 | | | | 70 | | | | | 75 | | | | | 80 | | |
| aag | gag | ttc | ggc | aca | ctc | gat | att | atg | att | aat | aat | gcc | ggt | ctt | gaa | 288 |
| Lys | Glu | Phe | Gly | Thr | Leu | Asp | Ile | Met | Ile | Asn | Asn | Ala | Gly | Leu | Glu | |
| | | | 85 | | | | | 90 | | | | | 95 | | | |
| aat | cct | gtg | cca | tct | cac | gaa | atg | ccg | ctc | aag | gat | tgg | gat | aaa | gtc | 336 |
| Asn | Pro | Val | Pro | Ser | His | Glu | Met | Pro | Leu | Lys | Asp | Trp | Asp | Lys | Val | |
| | | | 100 | | | | | 105 | | | | | 110 | | | |
| atc | ggc | acg | aac | tta | acg | ggt | gcc | ttt | tta | gga | agc | cgt | gaa | gcg | att | 384 |
| Ile | Gly | Thr | Asn | Leu | Thr | Gly | Ala | Phe | Leu | Gly | Ser | Arg | Glu | Ala | Ile | |
| | | 115 | | | | | 120 | | | | | 125 | | | | |
| aaa | tat | ttc | gta | gaa | aac | gat | atc | aag | gga | aat | gtc | att | aac | atg | tcc | 432 |
| Lys | Tyr | Phe | Val | Glu | Asn | Asp | Ile | Lys | Gly | Asn | Val | Ile | Asn | Met | Ser | |
| | 130 | | | | | 135 | | | | | 140 | | | | | |
| agt | gtg | cac | gaa | gtg | att | cct | tgg | ccg | tta | ttt | gtc | cac | tat | gcg | gca | 480 |
| Ser | Val | His | Glu | Val | Ile | Pro | Trp | Pro | Leu | Phe | Val | His | Tyr | Ala | Ala | |
| 145 | | | | 150 | | | | | 155 | | | | | 160 | | |
| agt | aaa | ggc | ggg | atg | aag | ctg | atg | aca | gaa | aca | tta | gcg | ttg | gaa | tac | 528 |
| Ser | Lys | Gly | Gly | Met | Lys | Leu | Met | Thr | Glu | Thr | Leu | Ala | Leu | Glu | Tyr | |
| | | | 165 | | | | | 170 | | | | | 175 | | | |
| gcg | ccg | aag | ggc | att | cgc | gtc | aat | aat | att | ggg | cca | ggt | gcg | atc | aac | 576 |
| Ala | Pro | Lys | Gly | Ile | Arg | Val | Asn | Asn | Ile | Gly | Pro | Gly | Ala | Ile | Asn | |
| | | | 180 | | | | | 185 | | | | | 190 | | | |
| acg | cca | atc | aat | gct | gaa | aaa | ttc | gct | gac | cct | aaa | cag | aaa | gct | gat | 624 |
| Thr | Pro | Ile | Asn | Ala | Glu | Lys | Phe | Ala | Asp | Pro | Lys | Gln | Lys | Ala | Asp | |
| | | 195 | | | | | 200 | | | | | 205 | | | | |
| gcc | gaa | agc | atg | att | cca | atg | gga | tat | atc | ggc | gaa | ccg | gag | gag | atc | 672 |
| Ala | Glu | Ser | Met | Ile | Pro | Met | Gly | Tyr | Ile | Gly | Glu | Pro | Glu | Glu | Ile | |
| | 210 | | | | | 215 | | | | | 220 | | | | | |
| gcc | gca | gta | gca | gcc | tgg | ctt | gct | tcg | aag | gaa | gcc | agc | tac | gtc | aca | 720 |
| | | | | | | | | | | | | | | | | |

```
Ala Ala Val Ala Ala Trp Leu Ala Ser Lys Glu Ala Ser Tyr Val Thr
225                 230                 235                 240 ggc gtc acg tta ttc gcg gac ggc ggt atg aca cta tat cct tca ttc        768
Gly Val Thr Leu Phe Ala Asp Gly Gly Met Thr Leu Tyr Pro Ser Phe
                245                 250                 255 cag gca ggc cgc ggt taa tga                                            789
Gln Ala Gly Arg Gly *   *
            260
```

<210> SEQ ID NO 64
<211> LENGTH: 261
<212> TYPE: PRT
<213> ORGANISM: Artificial Sequence
<220> FEATURE:
<223> OTHER INFORMATION: GDH 2331

<400> SEQUENCE: 64

```
Met Tyr Pro Asp Leu Lys Gly Lys Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Val Gln Gly
50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
            195                 200                 205

Ala Glu Ser Met Ile Pro Met Gly Tyr Ile Gly Glu Pro Glu Glu Ile
210                 215                 220

Ala Ala Val Ala Ala Trp Leu Ala Ser Lys Glu Ala Ser Tyr Val Thr
225                 230                 235                 240

Gly Val Thr Leu Phe Ala Asp Gly Gly Met Thr Leu Tyr Pro Ser Phe
                245                 250                 255

Gln Ala Gly Arg Gly
            260
```

<210> SEQ ID NO 65
<211> LENGTH: 789
<212> TYPE: DNA
<213> ORGANISM: Artificial Sequence
<220> FEATURE:
<223> OTHER INFORMATION: GDH 2279

```
<220> FEATURE:
<221> NAME/KEY: CDS
<222> LOCATION: (1)...(789)

<400> SEQUENCE: 65 atg tat ccg gat tta aaa gga aaa gtc gtc gct att aca gga gct gct      48
Met Tyr Pro Asp Leu Lys Gly Lys Val Val Ala Ile Thr Gly Ala Ala
 1               5                  10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
             20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
         35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
     50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat     624
Thr Pro Ile Asn Ala Glu Lys Phe Ala Asp Pro Lys Gln Lys Ala Asp
        195                 200                 205 gcc gaa agc atg att cca atg gga tat atc ggc gaa ccg gag gag atc     672
Ala Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240 ggc gtc acg tta ttc gcg gac ggc ggt atg aca caa tat cct tca ttc     768
Gly Val Thr Leu Phe Ala Asp Gly Gly Met Thr Gln Tyr Pro Ser Phe
                245                 250                 255 cag gca ggc cgc ggt taa tga                                         789
Gln Ala Gly Arg Gly *   *
            260

<210> SEQ ID NO 66
<211> LENGTH: 261
<212> TYPE: PRT
<213> ORGANISM: Artificial Sequence
```

<220> FEATURE:
<223> OTHER INFORMATION: GDH 2279

<400> SEQUENCE: 66

| | | | | | | | | | | | | | | |
|---|---|---|---|---|---|---|---|---|---|---|---|---|---|---|
| Met | Tyr | Pro | Asp | Leu | Lys | Gly | Lys | Val | Val | Ala | Ile | Thr | Gly | Ala | Ala |
| 1 | | | | 5 | | | | | 10 | | | | | 15 | |
| Ser | Gly | Leu | Gly | Lys | Ala | Met | Ala | Ile | Arg | Phe | Gly | Lys | Glu | Gln | Ala |
| | | | 20 | | | | | 25 | | | | | 30 | | |
| Lys | Val | Val | Ile | Asn | Tyr | Tyr | Ser | Asn | Lys | Gln | Asp | Pro | Asn | Glu | Val |
| | | | 35 | | | | | 40 | | | | | 45 | | |
| Lys | Glu | Val | Ile | Lys | Ala | Gly | Gly | Glu | Ala | Val | Val | Gln | Gly |
| | 50 | | | | | 55 | | | | | 60 | | |
| Asp | Val | Thr | Lys | Glu | Glu | Asp | Val | Lys | Asn | Ile | Val | Gln | Thr | Ala | Ile |
| 65 | | | | | 70 | | | | | 75 | | | | | 80 |
| Lys | Glu | Phe | Gly | Thr | Leu | Asp | Ile | Met | Ile | Asn | Asn | Ala | Gly | Leu | Glu |
| | | | | 85 | | | | | 90 | | | | | 95 | |
| Asn | Pro | Val | Pro | Ser | His | Glu | Met | Pro | Leu | Lys | Asp | Trp | Asp | Lys | Val |
| | | | 100 | | | | | 105 | | | | | 110 | | |
| Ile | Gly | Thr | Asn | Leu | Thr | Gly | Ala | Phe | Leu | Gly | Ser | Arg | Glu | Ala | Ile |
| | | | 115 | | | | | 120 | | | | | 125 | | |
| Lys | Tyr | Phe | Val | Glu | Asn | Asp | Ile | Lys | Gly | Asn | Val | Ile | Asn | Met | Ser |
| | 130 | | | | | 135 | | | | | 140 | | | | |
| Ser | Val | His | Glu | Val | Ile | Pro | Trp | Pro | Leu | Phe | Val | His | Tyr | Ala | Ala |
| 145 | | | | | 150 | | | | | 155 | | | | | 160 |
| Ser | Lys | Gly | Gly | Met | Lys | Leu | Met | Thr | Glu | Thr | Leu | Ala | Leu | Glu | Tyr |
| | | | | 165 | | | | | 170 | | | | | 175 | |
| Ala | Pro | Lys | Gly | Ile | Arg | Val | Asn | Asn | Ile | Gly | Pro | Gly | Ala | Ile | Asn |
| | | | 180 | | | | | 185 | | | | | 190 | | |
| Thr | Pro | Ile | Asn | Ala | Glu | Lys | Phe | Ala | Asp | Pro | Lys | Gln | Lys | Ala | Asp |
| | | | 195 | | | | | 200 | | | | | 205 | | |
| Ala | Glu | Ser | Met | Ile | Pro | Met | Gly | Tyr | Ile | Gly | Glu | Pro | Glu | Glu | Ile |
| | 210 | | | | | 215 | | | | | 220 | | | | |
| Ala | Ala | Val | Ala | Ala | Trp | Leu | Ala | Ser | Lys | Glu | Ala | Ser | Tyr | Val | Thr |
| 225 | | | | | 230 | | | | | 235 | | | | | 240 |
| Gly | Val | Thr | Leu | Phe | Ala | Asp | Gly | Gly | Met | Thr | Gln | Tyr | Pro | Ser | Phe |
| | | | | 245 | | | | | 250 | | | | | 255 | |
| Gln | Ala | Gly | Arg | Gly |
| | | | 260 | |

<210> SEQ ID NO 67
<211> LENGTH: 789
<212> TYPE: DNA
<213> ORGANISM: Artificial Sequence
<220> FEATURE:
<223> OTHER INFORMATION: GDH 2379
<220> FEATURE:
<221> NAME/KEY: CDS
<222> LOCATION: (1)...(789)

<400> SEQUENCE: 67

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |
| tca | ggg | ctc | gga | aag | gcg | atg | gcc | att | cgc | ttc | ggc | aag | gag | cag | gca | 96 |
| Ser | Gly | Leu | Gly | Lys | Ala | Met | Ala | Ile | Arg | Phe | Gly | Lys | Glu | Gln | Ala | |
| | | | 20 | | | | | 25 | | | | | 30 | | | |
| aaa | gtg | gtt | atc | aac | tat | tat | agt | aat | aaa | caa | gat | ccg | aac | gag | gta | 144 |
| Lys | Val | Val | Ile | Asn | Tyr | Tyr | Ser | Asn | Lys | Gln | Asp | Pro | Asn | Glu | Val | |

```
                35                  40                  45
aaa gaa gag gtc atc aag gcg ggc ggt gaa gct gtt gtc gtc caa gga    192
Lys Glu Glu Val Ile Lys Ala Gly Gly Glu Ala Val Val Val Gln Gly
         50                  55                  60 gat gtc acg aaa gag gaa gat gta aaa aat atc gtg caa acg gca att    240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa    288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc    336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att    384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc    432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca    480
Ser Val His Glu Val Ile Pro Trp Pro Leu Phe Val His Tyr Ala Ala
145                 150                 155                 160 agt aaa ggc ggg ctt aag ctg atg aca gaa aca tta gcg ttg gaa tac    528
Ser Lys Gly Gly Leu Lys Leu Met Thr Glu Thr Leu Ala Leu Glu Tyr
                165                 170                 175 gcg ccg aag ggc att cgc gtc aat aat att ggg cca ggt gcg atc aac    576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat    624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc    672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                245                 250                 255 cag gca ggc cgc ggt taa tga                                        789
Gln Ala Gly Arg Gly *   *
            260

<210> SEQ ID NO 68
<211> LENGTH: 261
<212> TYPE: PRT
<213> ORGANISM: Artificial Sequence
<220> FEATURE:
<223> OTHER INFORMATION: GDH 2379

<400> SEQUENCE: 68

Met Tyr Pro Asp Leu Lys Gly Lys Val Val Ala Ile Thr Gly Ala Ala
 1               5                  10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60
```

```
Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
             85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Leu Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 69
<211> LENGTH: 1206
<212> TYPE: DNA
<213> ORGANISM: Artificial Sequence
<220> FEATURE:
<223> OTHER INFORMATION: FDH FDHPs3
<220> FEATURE:
<221> NAME/KEY: CDS
<222> LOCATION: (1)...(1206)

<400> SEQUENCE: 69

```
atg gca aaa gtt cta tgt gtt cta tat gat gat ccg gtt gat ggt tat      48
Met Ala Lys Val Leu Cys Val Leu Tyr Asp Asp Pro Val Asp Gly Tyr
 1               5                  10                  15 ccg aaa acc tat gca cgt gat gat cta ccg aaa att gat cat tat ccg      96
Pro Lys Thr Tyr Ala Arg Asp Asp Leu Pro Lys Ile Asp His Tyr Pro
             20                  25                  30 ggt ggt cag acc cta ccg acc ccg aaa gca att gat ttt acc ccg ggt     144
Gly Gly Gln Thr Leu Pro Thr Pro Lys Ala Ile Asp Phe Thr Pro Gly
         35                  40                  45 cag cta cta ggt agc gtt agc ggt gaa cta ggt cta cgt aaa tat cta     192
Gln Leu Leu Gly Ser Val Ser Gly Glu Leu Gly Leu Arg Lys Tyr Leu
     50                  55                  60 gaa agc aac ggt cat acc cta gtt gtt acc agc gat aag gac ggc cct     240
Glu Ser Asn Gly His Thr Leu Val Val Thr Ser Asp Lys Asp Gly Pro
 65                  70                  75                  80 gac agc gtg ttc gag cgc gag cta gtg gac gcc gac gtg gtg att agc     288
Asp Ser Val Phe Glu Arg Glu Leu Val Asp Ala Asp Val Val Ile Ser
             85                  90                  95 cag cct ttc tgg cct gcc tat cta acc cct gag cgc att gcc aag gcc     336
Gln Pro Phe Trp Pro Ala Tyr Leu Thr Pro Glu Arg Ile Ala Lys Ala
```

```
                100                 105                  110
aag aat cta aag cta gcc cta acc gcc ggc att ggc agc gac cat gtg        384
Lys Asn Leu Lys Leu Ala Leu Thr Ala Gly Ile Gly Ser Asp His Val
        115                 120                 125 gac cta cag agc gcc att gac cgc aat gtg acc gtg gcc gag gtg acc        432
Asp Leu Gln Ser Ala Ile Asp Arg Asn Val Thr Val Ala Glu Val Thr
130                 135                 140 tat tgt aat agc att agc gtg gcc gag cat gtg gtg atg atg att cta        480
Tyr Cys Asn Ser Ile Ser Val Ala Glu His Val Val Met Met Ile Leu
145                 150                 155                 160 agc cta gtg cgc aat tat cta cct tcc cat gaa tgg gcg cgt aaa ggc        528
Ser Leu Val Arg Asn Tyr Leu Pro Ser His Glu Trp Ala Arg Lys Gly
                165                 170                 175 ggc tgg aac atc gcg gat tgc gtc tcc cat gcg tat gat ctg gaa gcg        576
Gly Trp Asn Ile Ala Asp Cys Val Ser His Ala Tyr Asp Leu Glu Ala
            180                 185                 190 atg cat gtc ggc acg gtc gcg gcg ggc cgt atc gcc ctg gcg gtc ctg        624
Met His Val Gly Thr Val Ala Ala Gly Arg Ile Ala Leu Ala Val Leu
        195                 200                 205 cgt cgt ctg gcg ccg ttt gat gtc cat ctg cat tat acg gat cgt cat        672
Arg Arg Leu Ala Pro Phe Asp Val His Leu His Tyr Thr Asp Arg His
210                 215                 220 cgt ctg ccg gaa tcg gta gaa aaa gaa tta aac tta acg tgg cat gcg        720
Arg Leu Pro Glu Ser Val Glu Lys Glu Leu Asn Leu Thr Trp His Ala
225                 230                 235                 240 acg agg gaa gat atg tac cca gta tgt gat gta gta acg tta aac tgt        768
Thr Arg Glu Asp Met Tyr Pro Val Cys Asp Val Val Thr Leu Asn Cys
                245                 250                 255 cca tta cat cca gaa acg gaa cat atg att aac gat gaa acg tta aaa        816
Pro Leu His Pro Glu Thr Glu His Met Ile Asn Asp Glu Thr Leu Lys
            260                 265                 270 tta ttc aaa agg gga gcg tac att gtc aac acg gcg aga ggc aaa ttg        864
Leu Phe Lys Arg Gly Ala Tyr Ile Val Asn Thr Ala Arg Gly Lys Leu
        275                 280                 285 tgc gat aga gat gcg gtc gcg aga gcg ttg gaa tca ggc aga ttg gca        912
Cys Asp Arg Asp Ala Val Ala Arg Ala Leu Glu Ser Gly Arg Leu Ala
290                 295                 300 ggc tat gcg ggc gat gtc tgg ttt ccg caa ccg gcg ccg aaa gat cat        960
Gly Tyr Ala Gly Asp Val Trp Phe Pro Gln Pro Ala Pro Lys Asp His
305                 310                 315                 320 ccg tgg aga acg atg ccg tat aac ggc atg acg ccg cat att tca ggc       1008
Pro Trp Arg Thr Met Pro Tyr Asn Gly Met Thr Pro His Ile Ser Gly
                325                 330                 335 acg acg ttg acg gcg caa gcg aga tat gct gcg ggc acg aga gaa att       1056
Thr Thr Leu Thr Ala Gln Ala Arg Tyr Ala Ala Gly Thr Arg Glu Ile
            340                 345                 350 ttg gaa tgc ttt ttt gaa ggc aga cca atc cgt gac gaa tat ctg atc       1104
Leu Glu Cys Phe Phe Glu Gly Arg Pro Ile Arg Asp Glu Tyr Leu Ile
        355                 360                 365 gtc cag ggt ggt gcc ctg gcc ggt acc ggt gcc cat tct tat tct aaa       1152
Val Gln Gly Gly Ala Leu Ala Gly Thr Gly Ala His Ser Tyr Ser Lys
370                 375                 380 ggt aat gcc acc ggt ggt tct gaa gaa gcc aaa ttc aaa aaa gcc gtc       1200
Gly Asn Ala Thr Gly Gly Ser Glu Glu Ala Lys Phe Lys Lys Ala Val
385                 390                 395                 400 taa tga                                                                1206
 *   *
```

<210> SEQ ID NO 70

```
<211> LENGTH: 400
<212> TYPE: PRT
<213> ORGANISM: Pseudomonas sp. strain 101

<400> SEQUENCE: 70
```

| | | | | | | | | | | | | | | |
|---|---|---|---|---|---|---|---|---|---|---|---|---|---|---|
|Met|Ala|Lys|Val|Leu|Cys|Val|Leu|Tyr|Asp|Asp|Pro|Val|Asp|Gly|Tyr|
|1| | | |5| | | | |10| | | | |15| |

Pro Lys Thr Tyr Ala Arg Asp Asp Leu Pro Lys Ile Asp His Tyr Pro
            20                  25                  30

Gly Gly Gln Thr Leu Pro Thr Pro Lys Ala Ile Asp Phe Thr Pro Gly
                35                  40                  45

Gln Leu Leu Gly Ser Val Ser Gly Glu Leu Gly Leu Arg Lys Tyr Leu
    50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Val Ile Ser
                85                  90                  95

Gln Pro Phe Trp Pro Ala Tyr Leu Thr Pro Glu Arg Ile Ala Lys Ala
                100                 105                 110

Lys Asn Leu Lys Leu Ala Leu Thr Ala Gly Ile Gly Ser Asp His Val
            115                 120                 125

Asp Leu Gln Ser Ala Ile Asp Arg Asn Val Thr Val Ala Glu Val Thr
    130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Ala Leu Ala Val Leu
    195                 200                 205

Arg Arg Leu Ala Pro Phe Asp Val His Leu His Tyr Thr Asp Arg His
210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
    275                 280                 285

Cys Asp Arg Asp Ala Val Ala Arg Ala Leu Glu Ser Gly Arg Leu Ala
290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
    355                 360                 365

Val Gln Gly Gly Ala Leu Ala Gly Thr Gly Ala His Ser Tyr Ser Lys
370                 375                 380

Gly Asn Ala Thr Gly Gly Ser Glu Glu Ala Lys Phe Lys Lys Ala Val

<210> SEQ ID NO 71
<211> LENGTH: 1098
<212> TYPE: DNA
<213> ORGANISM: Artificial Sequence
<220> FEATURE:
<223> OTHER INFORMATION: FDH FDHCb13
<220> FEATURE:
<221> NAME/KEY: CDS
<222> LOCATION: (1)...(1098)

<400> SEQUENCE: 71

| | | | | | | | | | | | | | | | | |
|---|---|---|---|---|---|---|---|---|---|---|---|---|---|---|---|---|
| atg | aaa | atc | gta | ctc | gta | ctc | tac | gat | gca | ggc | aaa | cac | gca | gca | gat | 48 |
| Met | Lys | Ile | Val | Leu | Val | Leu | Tyr | Asp | Ala | Gly | Lys | His | Ala | Ala | Asp | |
| 1 | | | | 5 | | | | | 10 | | | | | 15 | | |
| gaa | gaa | aaa | ctc | tac | ggc | tgc | acg | gaa | aat | aag | ctg | ggc | att | gca | aat | 96 |
| Glu | Glu | Lys | Leu | Tyr | Gly | Cys | Thr | Glu | Asn | Lys | Leu | Gly | Ile | Ala | Asn | |
| | | | | 20 | | | | | 25 | | | | | 30 | | |
| tgg | ctg | aag | gat | cag | ggc | cac | gaa | ctg | att | acg | acg | tca | gat | aag | gaa | 144 |
| Trp | Leu | Lys | Asp | Gln | Gly | His | Glu | Leu | Ile | Thr | Thr | Ser | Asp | Lys | Glu | |
| | | 35 | | | | | 40 | | | | | 45 | | | | |
| ggc | ggt | aat | tcc | gtc | ttg | gat | caa | cac | atc | ccc | gat | gct | gat | atc | atc | 192 |
| Gly | Gly | Asn | Ser | Val | Leu | Asp | Gln | His | Ile | Pro | Asp | Ala | Asp | Ile | Ile | |
| | 50 | | | | | 55 | | | | | 60 | | | | | |
| atc | aca | aca | ccc | ttc | cac | ccc | gct | tac | atc | aca | aaa | gaa | aga | atc | gat | 240 |
| Ile | Thr | Thr | Pro | Phe | His | Pro | Ala | Tyr | Ile | Thr | Lys | Glu | Arg | Ile | Asp | |
| 65 | | | | | 70 | | | | | 75 | | | | | 80 | |
| aaa | gct | aaa | aaa | ttg | aaa | ttg | gtc | gtc | gtc | gct | ggt | gtc | ggt | tcc | gat | 288 |
| Lys | Ala | Lys | Lys | Leu | Lys | Leu | Val | Val | Val | Ala | Gly | Val | Gly | Ser | Asp | |
| | | | | 85 | | | | | 90 | | | | | 95 | | |
| cac | atc | gat | ttg | gat | tac | atc | aat | caa | aca | ggt | aaa | aaa | atc | tcc | gtc | 336 |
| His | Ile | Asp | Leu | Asp | Tyr | Ile | Asn | Gln | Thr | Gly | Lys | Lys | Ile | Ser | Val | |
| | | | | 100 | | | | | 105 | | | | | 110 | | |
| ttg | gaa | gtc | aca | ggt | tcc | aat | gtc | gtc | tcc | gtc | gct | gaa | cac | gtc | gtc | 384 |
| Leu | Glu | Val | Thr | Gly | Ser | Asn | Val | Val | Ser | Val | Ala | Glu | His | Val | Val | |
| | | 115 | | | | | 120 | | | | | 125 | | | | |
| atg | aca | atg | ttg | gtc | ttg | gtc | aga | aat | ttc | gtc | ccc | gct | cac | gaa | caa | 432 |
| Met | Thr | Met | Leu | Val | Leu | Val | Arg | Asn | Phe | Val | Pro | Ala | His | Glu | Gln | |
| | 130 | | | | | 135 | | | | | 140 | | | | | |
| atc | atc | aat | cac | gat | tgg | gaa | gtc | gct | gct | atc | gct | aaa | gat | gct | tac | 480 |
| Ile | Ile | Asn | His | Asp | Trp | Glu | Val | Ala | Ala | Ile | Ala | Lys | Asp | Ala | Tyr | |
| 145 | | | | | 150 | | | | | 155 | | | | | 160 | |
| gat | atc | gaa | ggt | aaa | aca | atc | gct | aca | atc | ggt | gct | ggt | aga | atc | ggt | 528 |
| Asp | Ile | Glu | Gly | Lys | Thr | Ile | Ala | Thr | Ile | Gly | Ala | Gly | Arg | Ile | Gly | |
| | | | | 165 | | | | | 170 | | | | | 175 | | |
| tac | aga | gtc | ttg | gaa | aga | ttg | gtc | ccc | ttc | aat | ccc | aaa | gaa | ttg | ttg | 576 |
| Tyr | Arg | Val | Leu | Glu | Arg | Leu | Val | Pro | Phe | Asn | Pro | Lys | Glu | Leu | Leu | |
| | | | 180 | | | | | 185 | | | | | 190 | | | |
| tac | tac | gat | tac | caa | gct | ttg | ccc | aaa | gat | gct | gaa | gaa | aaa | gtt | ggt | 624 |
| Tyr | Tyr | Asp | Tyr | Gln | Ala | Leu | Pro | Lys | Asp | Ala | Glu | Glu | Lys | Val | Gly | |
| | | 195 | | | | | 200 | | | | | 205 | | | | |
| gct | cgt | cgt | gtt | gaa | aac | ata | gaa | gaa | ttg | gtt | gct | cag | gct | gat | ata | 672 |
| Ala | Arg | Arg | Val | Glu | Asn | Ile | Glu | Glu | Leu | Val | Ala | Gln | Ala | Asp | Ile | |
| | 210 | | | | | 215 | | | | | 220 | | | | | |
| gtt | acc | gtt | aac | gct | ccg | ttg | cac | gct | ggt | acc | aaa | ggt | ttg | ata | aac | 720 |
| Val | Thr | Val | Asn | Ala | Pro | Leu | His | Ala | Gly | Thr | Lys | Gly | Leu | Ile | Asn | |
| 225 | | | | | 230 | | | | | 235 | | | | | 240 | |
| aaa | gaa | ttg | ttg | tca | aaa | ttt | aaa | aaa | ggt | gct | tgg | ttg | ctt | aac | acc | 768 |
| Lys | Glu | Leu | Leu | Ser | Lys | Phe | Lys | Lys | Gly | Ala | Trp | Leu | Leu | Asn | Thr | |
| | | | | 245 | | | | | 250 | | | | | 255 | | |

-continued

| | | |
|---|---|---|
| gct cgt ggt gct ata tgc gtt gct gaa gat gtt gct gct ttg gaa<br>Ala Arg Gly Ala Ile Cys Val Ala Glu Asp Val Ala Ala Leu Glu<br>260 265 270 | | 816 |
| tca ggt cag ttg cgt ggt tac ggt ggt gat gtt tgg ttt ccg cag ccg<br>Ser Gly Gln Leu Arg Gly Tyr Gly Gly Asp Val Trp Phe Pro Gln Pro<br>275 280 285 | | 864 |
| gct ccg aaa gat cac ccg tgg cgt gat atg cgt aac aaa tac ggt gct<br>Ala Pro Lys Asp His Pro Trp Arg Asp Met Arg Asn Lys Tyr Gly Ala<br>290 295 300 | | 912 |
| ggt aac gct atg acc ccg cac tac tca ggt acc acc ttg gat gct cag<br>Gly Asn Ala Met Thr Pro His Tyr Ser Gly Thr Thr Leu Asp Ala Gln<br>305 310 315 320 | | 960 |
| acc cgt tac gct cag ggt acc aaa aac atc ctc gaa tcg ttt ttt acc<br>Thr Arg Tyr Ala Gln Gly Thr Lys Asn Ile Leu Glu Ser Phe Phe Thr<br>325 330 335 | | 1008 |
| ggt aaa ttt gat tat cgt cca cag gat atc atc ctc ctc aac ggt gaa<br>Gly Lys Phe Asp Tyr Arg Pro Gln Asp Ile Ile Leu Leu Asn Gly Glu<br>340 345 350 | | 1056 |
| tat gtt acc aaa gcc tat ggt aaa cac gat aaa aaa taa tga<br>Tyr Val Thr Lys Ala Tyr Gly Lys His Asp Lys Lys * *<br>355 360 | | 1098 |

<210> SEQ ID NO 72
<211> LENGTH: 364
<212> TYPE: PRT
<213> ORGANISM: Candida boidinii

<400> SEQUENCE: 72

Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
                20                  25                  30

Trp Leu Lys Asp Gln Gly His Glu Leu Ile Thr Thr Ser Asp Lys Glu
            35                  40                  45

Gly Gly Asn Ser Val Leu Asp Gln His Ile Pro Asp Ala Asp Ile Ile
        50                  55                  60

Ile Thr Thr Pro Phe His Pro Ala Tyr Ile Thr Lys Glu Arg Ile Asp
65                  70                  75                  80

Lys Ala Lys Lys Leu Lys Leu Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Val Pro Phe Asn Pro Lys Glu Leu Leu
            180                 185                 190

Tyr Tyr Asp Tyr Gln Ala Leu Pro Lys Asp Ala Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn

-continued

```
            225                 230                 235                 240
Lys Glu Leu Leu Ser Lys Phe Lys Lys Gly Ala Trp Leu Leu Asn Thr
                    245                 250                 255

Ala Arg Gly Ala Ile Cys Val Ala Glu Asp Val Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Gln Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355                 360
```

<210> SEQ ID NO 73
<211> LENGTH: 765
<212> TYPE: DNA
<213> ORGANISM: Artificial Sequence
<220> FEATURE:
<223> OTHER INFORMATION: HHDH P016514-B-12
<220> FEATURE:
<221> NAME/KEY: CDS
<222> LOCATION: (1)...(765)

<400> SEQUENCE: 73

```
atg agc acc gct atc gtc acc aac gtc aaa cat ttt gga ggt atg ggt      48
Met Ser Thr Ala Ile Val Thr Asn Val Lys His Phe Gly Gly Met Gly
  1               5                  10                  15 agc gct ctg agg ctg agc gaa gct ggt cat acc gtc gct tgc cat gat      96
Ser Ala Leu Arg Leu Ser Glu Ala Gly His Thr Val Ala Cys His Asp
             20                  25                  30 gaa agc ttt aaa cag aaa gat gaa ctg gaa gct ttt gct gaa acc tac     144
Glu Ser Phe Lys Gln Lys Asp Glu Leu Glu Ala Phe Ala Glu Thr Tyr
         35                  40                  45 cca cag ctg aaa cca atg agc gaa cag gaa cca gct gaa ctg atc gaa     192
Pro Gln Leu Lys Pro Met Ser Glu Gln Glu Pro Ala Glu Leu Ile Glu
     50                  55                  60 gct gtc acc agc gct tac ggt cag gtc gat gtc ctg gtc agc aac gat     240
Ala Val Thr Ser Ala Tyr Gly Gln Val Asp Val Leu Val Ser Asn Asp
 65                  70                  75                  80 atc ttt gct cca gaa ttt cag cca atc gat aaa tac gct gtc cag gat     288
Ile Phe Ala Pro Glu Phe Gln Pro Ile Asp Lys Tyr Ala Val Gln Asp
                 85                  90                  95 tac agg ggt gct gtc gaa gct ctg cag atc agg cca ttt gct cta gtg     336
Tyr Arg Gly Ala Val Glu Ala Leu Gln Ile Arg Pro Phe Ala Leu Val
            100                 105                 110 aat gct gtg gct tcg caa atg aag aag cga aag tcg ggg cac atc atc     384
Asn Ala Val Ala Ser Gln Met Lys Lys Arg Lys Ser Gly His Ile Ile
        115                 120                 125 ttc atc act tcg gct gct ccg ttc ggg cca tgg aag gag cta tcg act     432
Phe Ile Thr Ser Ala Ala Pro Phe Gly Pro Trp Lys Glu Leu Ser Thr
    130                 135                 140 tac act tcg gct cga gct ggg gct tgt tcc cta gct aat gct cta tcg     480
Tyr Thr Ser Ala Arg Ala Gly Ala Cys Ser Leu Ala Asn Ala Leu Ser
145                 150                 155                 160
```

```
aag gag cta gga gag tac aat atc ccg gtg ttc gct atc ggg ccg aat      528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg      576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta      624
Lys Thr Asn Pro Glu His Val Ala His Val Lys Lys Val Thr Ala Leu
            195                 200                 205 caa cga cta ggg act caa aaa gag ttg ggg gaa ttg gtg gca ttt ttg      672
Gln Arg Leu Gly Thr Gln Lys Glu Leu Gly Glu Leu Val Ala Phe Leu
        210                 215                 220 gca tct ggc tct tgt gat tat ttg act ggc cag gtg ttt tgg ttg gca      720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa          765
Gly Gly Phe Pro Met Ile Glu Arg Trp Pro Gly Met Pro Glu *
                245                 250
```

<210> SEQ ID NO 74
<211> LENGTH: 254
<212> TYPE: PRT
<213> ORGANISM: Artificial Sequence
<220> FEATURE:
<223> OTHER INFORMATION: HHDH P016514-B-12

<400> SEQUENCE: 74

```
Met Ser Thr Ala Ile Val Thr Asn Val Lys His Phe Gly Gly Met Gly
 1               5                  10                  15

Ser Ala Leu Arg Leu Ser Glu Ala Gly His Thr Val Ala Cys His Asp
                20                  25                  30

Glu Ser Phe Lys Gln Lys Asp Glu Leu Glu Ala Phe Ala Glu Thr Tyr
            35                  40                  45

Pro Gln Leu Lys Pro Met Ser Glu Gln Glu Pro Ala Glu Leu Ile Glu
        50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Gln Asp
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Thr Ser Ala Arg Ala Gly Ala Cys Ser Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240
```

```
Gly Gly Phe Pro Met Ile Glu Arg Trp Pro Gly Met Pro Glu
                245                 250

<210> SEQ ID NO 75
<211> LENGTH: 765
<212> TYPE: DNA
<213> ORGANISM: Artificial Sequence
<220> FEATURE:
<223> OTHER INFORMATION: HHDH Mz1/4H6
<220> FEATURE:
<221> NAME/KEY: CDS
<222> LOCATION: (1)...(765)

<400> SEQUENCE: 75 atg agc acc gct atc gtc acc aac gtc aaa cat ttt ggt ggt atg ggt        48
Met Ser Thr Ala Ile Val Thr Asn Val Lys His Phe Gly Gly Met Gly
1               5                   10                  15 agc gct ctg agg ctg agc gaa gct ggt cat acc gtc gct tgc cat gat        96
Ser Ala Leu Arg Leu Ser Glu Ala Gly His Thr Val Ala Cys His Asp
                20                  25                  30 gaa agc ttt aaa cag aaa gat gaa ctg gaa gct ttt gct gaa acc tac       144
Glu Ser Phe Lys Gln Lys Asp Glu Leu Glu Ala Phe Ala Glu Thr Tyr
            35                  40                  45 cca cag ctg aaa cca atg agc gaa cag gaa cca gct gaa ctg atc gaa       192
Pro Gln Leu Lys Pro Met Ser Glu Gln Glu Pro Ala Glu Leu Ile Glu
        50                  55                  60 gct gtc acc agc gct tac ggt cag gtc gat gtc ctg gtc agc aac gat       240
Ala Val Thr Ser Ala Tyr Gly Gln Val Asp Val Leu Val Ser Asn Asp
65                  70                  75                  80 atc ttt gct cca gaa ttt cag cca atc gat aaa tac gct gtc gaa gat       288
Ile Phe Ala Pro Glu Phe Gln Pro Ile Asp Lys Tyr Ala Val Glu Asp
                85                  90                  95 tac agg ggt gct gtc gaa gct ctg cag atc agg cca ttt gct cta gtg       336
Tyr Arg Gly Ala Val Glu Ala Leu Gln Ile Arg Pro Phe Ala Leu Val
                100                 105                 110 aat gct gtg gct tcg caa atg aag aag cga aag tcg ggg cac atc atc       384
Asn Ala Val Ala Ser Gln Met Lys Lys Arg Lys Ser Gly His Ile Ile
            115                 120                 125 ttc atc act tcg gct act ccg ttc ggg ccg tgg aag gag cta tcg act       432
Phe Ile Thr Ser Ala Thr Pro Phe Gly Pro Trp Lys Glu Leu Ser Thr
        130                 135                 140 tac act tcg gct cga gct ggg gct tgt act cta gct aat gct cta tcg       480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat       528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg       576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta       624
Lys Thr Asn Pro Glu His Val Ala His Val Lys Lys Val Thr Ala Leu
        195                 200                 205 caa cga cta ggg act caa aaa gag ttg ggg gaa ttg gtg gca ttt ttg       672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca       720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa           765
Gly Gly Phe Pro Met Ile Glu Arg Trp Pro Gly Met Pro Glu *
                245                 250
```

<210> SEQ ID NO 76
<211> LENGTH: 254
<212> TYPE: PRT
<213> ORGANISM: Artificial Sequence
<220> FEATURE:
<223> OTHER INFORMATION: HHDH Mz1/4H6

<400> SEQUENCE: 76

```
Met Ser Thr Ala Ile Val Thr Asn Val Lys His Phe Gly Gly Met Gly
 1               5                  10                  15

Ser Ala Leu Arg Leu Ser Glu Ala Gly His Thr Val Ala Cys His Asp
            20                  25                  30

Glu Ser Phe Lys Gln Lys Asp Glu Leu Glu Ala Phe Ala Glu Thr Tyr
        35                  40                  45

Pro Gln Leu Lys Pro Met Ser Glu Gln Glu Pro Ala Glu Leu Ile Glu
    50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Glu Asp
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
    130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250
```

<210> SEQ ID NO 77
<211> LENGTH: 765
<212> TYPE: DNA
<213> ORGANISM: Artificial Sequence
<220> FEATURE:
<223> OTHER INFORMATION: HHDH P016229-F-04
<220> FEATURE:
<221> NAME/KEY: CDS
<222> LOCATION: (1)...(765)

<400> SEQUENCE: 77

```
atg agc acc gct atc gtc acc aac gtc aaa cat ttt gga ggt atg ggt      48
Met Ser Thr Ala Ile Val Thr Asn Val Lys His Phe Gly Gly Met Gly
 1               5                  10                  15 agt gct ctg agg ctg tcg gag gct ggt cac acc gtc gct tgc cat gat      96
Ser Ala Leu Arg Leu Ser Glu Ala Gly His Thr Val Ala Cys His Asp
            20                  25                  30
```

-continued

```
gaa agc ttt aaa cag aaa gat gaa ctg gag gct ttt gct gaa acc tac    144
Glu Ser Phe Lys Gln Lys Asp Glu Leu Glu Ala Phe Ala Glu Thr Tyr
        35                  40                  45 cca cag ctg aaa cca atg agc gaa cag gaa cca gct gga ctg att gaa    192
Pro Gln Leu Lys Pro Met Ser Glu Gln Glu Pro Ala Gly Leu Ile Glu
 50                  55                  60 gct gtc acc agc gct tac ggt cag gtc gat gtc ctg gtc agc aac gat    240
Ala Val Thr Ser Ala Tyr Gly Gln Val Asp Val Leu Val Ser Asn Asp
 65                  70                  75                  80 atc ttt gct cca gaa ttt cag cca atc gat aaa tac gct gtc gaa gat    288
Ile Phe Ala Pro Glu Phe Gln Pro Ile Asp Lys Tyr Ala Val Glu Asp
                85                  90                  95 tac agg ggt gct gtc gaa gct ctg cag atc agg cca ttt gct cta gtg    336
Tyr Arg Gly Ala Val Glu Ala Leu Gln Ile Arg Pro Phe Ala Leu Val
            100                 105                 110 aat gct gtg gct tcg caa atg aag aag cga aag tcg ggg cac atc atc    384
Asn Ala Val Ala Ser Gln Met Lys Lys Arg Lys Ser Gly His Ile Ile
        115                 120                 125 ttc atc act tcg gct act ccg ttc ggg cca tgg aag gag cta tcg act    432
Phe Ile Thr Ser Ala Thr Pro Phe Gly Pro Trp Lys Glu Leu Ser Thr
    130                 135                 140 tac act tcg gct cga gct ggg gct tgt act cta gct aat gct cta tcg    480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat    528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg    576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta    624
Lys Thr Asn Pro Glu His Val Ala His Val Lys Lys Val Thr Ala Leu
        195                 200                 205 caa cga cta ggg act caa aaa gag ttg ggg gaa ttg gtg gca ttt ttg    672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca    720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa       765
Gly Gly Phe Pro Met Ile Glu Arg Trp Pro Gly Met Pro Glu *
                245                 250
```

<210> SEQ ID NO 78
<211> LENGTH: 254
<212> TYPE: PRT
<213> ORGANISM: Artificial Sequence
<220> FEATURE:
<223> OTHER INFORMATION: HHDH P016229-F-04

<400> SEQUENCE: 78

```
Met Ser Thr Ala Ile Val Thr Asn Val Lys His Phe Gly Gly Met Gly
  1               5                  10                  15

Ser Ala Leu Arg Leu Ser Glu Ala Gly His Thr Val Ala Cys His Asp
                 20                  25                  30

Glu Ser Phe Lys Gln Lys Asp Glu Leu Glu Ala Phe Ala Glu Thr Tyr
         35                  40                  45

Pro Gln Leu Lys Pro Met Ser Glu Gln Glu Pro Ala Gly Leu Ile Glu
     50                  55                  60
```

```
Ala Val Thr Ser Ala Tyr Gly Gln Val Asp Val Leu Val Ser Asn Asp
 65                  70                  75                  80

Ile Phe Ala Pro Glu Phe Gln Pro Ile Asp Lys Tyr Ala Val Glu Asp
                 85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
    130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250

<210> SEQ ID NO 79
<211> LENGTH: 765
<212> TYPE: DNA
<213> ORGANISM: Artificial Sequence
<220> FEATURE:
<223> OTHER INFORMATION: HHDH P016230-A-08
<220> FEATURE:
<221> NAME/KEY: CDS
<222> LOCATION: (1)...(765)

<400> SEQUENCE: 79 atg agc acc gct atc gtc acc aac gtc aaa cat ttt gga ggt atg ggt      48
Met Ser Thr Ala Ile Val Thr Asn Val Lys His Phe Gly Gly Met Gly
  1               5                  10                  15 agc gct ctg agg ctg agc gaa gct ggt cat acc gtc gct tgc cat gat      96
Ser Ala Leu Arg Leu Ser Glu Ala Gly His Thr Val Ala Cys His Asp
             20                  25                  30 gaa agc ttt aaa cag aaa gat gaa ctg gaa gct ttt gct gaa acc tac     144
Glu Ser Phe Lys Gln Lys Asp Glu Leu Glu Ala Phe Ala Glu Thr Tyr
         35                  40                  45 cca cag ctg aaa cca atg agc gaa cag gaa cca gct gaa ctg atc gaa     192
Pro Gln Leu Lys Pro Met Ser Glu Gln Glu Pro Ala Glu Leu Ile Glu
     50                  55                  60 gct gtc acc agc gct tac ggt cag gtc gat gtc ctg gtc agc aac gat     240
Ala Val Thr Ser Ala Tyr Gly Gln Val Asp Val Leu Val Ser Asn Asp
 65                  70                  75                  80 atc ttt gct cca gaa ttt cag cca atc gat aaa tac gct gtc gaa gat     288
Ile Phe Ala Pro Glu Phe Gln Pro Ile Asp Lys Tyr Ala Val Glu Asp
                 85                  90                  95 tat cgt ggt gct gtc gaa gct ctg cag atc agg cca ttt gct cta gtg     336
Tyr Arg Gly Ala Val Glu Ala Leu Gln Ile Arg Pro Phe Ala Leu Val
            100                 105                 110 aat gct gtg gct tcg caa atg aag aag cga aag tcg ggg cac atc atc     384
Asn Ala Val Ala Ser Gln Met Lys Lys Arg Lys Ser Gly His Ile Ile
```

-continued

```
            115                 120                 125
ttc atc act tcg gct act ccg ttc ggg cca tgg aag gag cta tcg act    432
Phe Ile Thr Ser Ala Thr Pro Phe Gly Pro Trp Lys Glu Leu Ser Thr
    130                 135                 140 tac act tcg gct cga gct ggg gct tgt act cta gct aat gct cta tcg    480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat    528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg    576
Tyr Leu His Ser Glu Asp Ser Pro Tyr Phe Tyr Pro Thr Glu Pro Trp
            180                 185                 190 aag act aat ccg gaa cac gtg gct cac gtg aag aag gtg act gct cta    624
Lys Thr Asn Pro Glu His Val Ala His Val Lys Lys Val Thr Ala Leu
        195                 200                 205 caa cga cta ggg act caa aaa gag ttg ggg gaa ttg gtg gca ttt ttg    672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca    720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa       765
Gly Gly Phe Pro Met Ile Glu Arg Trp Pro Gly Met Pro Glu  *
                245                 250

<210> SEQ ID NO 80
<211> LENGTH: 254
<212> TYPE: PRT
<213> ORGANISM: Artificial Sequence
<220> FEATURE:
<223> OTHER INFORMATION: HHDH P016230-A-08

<400> SEQUENCE: 80

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys Gln Lys Asp Glu Leu Glu Ala Phe Ala Glu Thr Tyr
        35                  40                  45

Pro Gln Leu Lys Pro Met Ser Glu Gln Glu Pro Ala Glu Leu Ile Glu
    50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Glu Asp
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
    130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190
```

```
Lys Thr Asn Pro Glu His Val Ala His Val Lys Lys Val Thr Ala Leu
            195                 200                 205

Gln Arg Leu Gly Thr Gln Lys Glu Leu Gly Glu Leu Val Ala Phe Leu
        210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250

<210> SEQ ID NO 81
<211> LENGTH: 765
<212> TYPE: DNA
<213> ORGANISM: Artificial Sequence
<220> FEATURE:
<223> OTHER INFORMATION: HHDH P016096-G9
<220> FEATURE:
<221> NAME/KEY: CDS
<222> LOCATION: (1)...(765)

<400> SEQUENCE: 81
```

| | | | | | | | | | | | | | | | | |
|---|---|---|---|---|---|---|---|---|---|---|---|---|---|---|---|---|
| atg agc acc gct atc gtc acc aac gtc aaa cat ttt gga ggt atg ggt | | | | | | | | | | | | | | | | 48 |
| Met Ser Thr Ala Ile Val Thr Asn Val Lys His Phe Gly Gly Met Gly | | | | | | | | | | | | | | | | |
| 1 | | | 5 | | | | | 10 | | | | | 15 | | | |
| agc gct ctg agg ctg agc gaa gct ggt cat acc gtc gct tgc cat gat | | | | | | | | | | | | | | | | 96 |
| Ser Ala Leu Arg Leu Ser Glu Ala Gly His Thr Val Ala Cys His Asp | | | | | | | | | | | | | | | | |
| | | | 20 | | | | | 25 | | | | | 30 | | | |
| gaa agc ttt aaa cag aaa gat gaa ctg gaa gct ttt gct gaa acc tac | | | | | | | | | | | | | | | | 144 |
| Glu Ser Phe Lys Gln Lys Asp Glu Leu Glu Ala Phe Ala Glu Thr Tyr | | | | | | | | | | | | | | | | |
| | | 35 | | | | | 40 | | | | | 45 | | | | |
| cca cag ctg aaa cca atg agc gaa cag gaa cca gct gaa ctg atc gaa | | | | | | | | | | | | | | | | 192 |
| Pro Gln Leu Lys Pro Met Ser Glu Gln Glu Pro Ala Glu Leu Ile Glu | | | | | | | | | | | | | | | | |
| 50 | | | | | 55 | | | | | 60 | | | | | | |
| gct gtc acc agc gct tac ggt cag gtc gat gtc ctg gtc agc aac gat | | | | | | | | | | | | | | | | 240 |
| Ala Val Thr Ser Ala Tyr Gly Gln Val Asp Val Leu Val Ser Asn Asp | | | | | | | | | | | | | | | | |
| 65 | | | | 70 | | | | | 75 | | | | | 80 | | |
| atc ttt gct cca gaa ttt cag cca atc gat aaa tac gct gtc gaa gat | | | | | | | | | | | | | | | | 288 |
| Ile Phe Ala Pro Glu Phe Gln Pro Ile Asp Lys Tyr Ala Val Glu Asp | | | | | | | | | | | | | | | | |
| | | | | 85 | | | | | 90 | | | | | 95 | | |
| tac agg ggt gct gtc gaa gct ctg cag atc agg cca ttt gct cta gtg | | | | | | | | | | | | | | | | 336 |
| Tyr Arg Gly Ala Val Glu Ala Leu Gln Ile Arg Pro Phe Ala Leu Val | | | | | | | | | | | | | | | | |
| | | | 100 | | | | | 105 | | | | | 110 | | | |
| aat gct gtg gct tcg caa atg aag aag cga aag tcg ggg cac atc atc | | | | | | | | | | | | | | | | 384 |
| Asn Ala Val Ala Ser Gln Met Lys Lys Arg Lys Ser Gly His Ile Ile | | | | | | | | | | | | | | | | |
| | | | 115 | | | | | 120 | | | | | 125 | | | |
| ttc atc act tcg gct act ccg ttc ggg cca tgg aaa gag cta tcg act | | | | | | | | | | | | | | | | 432 |
| Phe Ile Thr Ser Ala Thr Pro Phe Gly Pro Trp Lys Glu Leu Ser Thr | | | | | | | | | | | | | | | | |
| | | 130 | | | | | 135 | | | | | 140 | | | | |
| tac act tcg gct cga gct ggg gct tgt act cta gct aat gct cta tcg | | | | | | | | | | | | | | | | 480 |
| Tyr Thr Ser Ala Arg Ala Gly Ala Cys Thr Leu Ala Asn Ala Leu Ser | | | | | | | | | | | | | | | | |
| 145 | | | | | 150 | | | | | 155 | | | | | 160 | |
| aag gag cta gga gag tac aat atc ccg gtg ttc gct atc ggg ccg aat | | | | | | | | | | | | | | | | 528 |
| Lys Glu Leu Gly Glu Tyr Asn Ile Pro Val Phe Ala Ile Gly Pro Asn | | | | | | | | | | | | | | | | |
| | | | | 165 | | | | | 170 | | | | | 175 | | |
| tac cta cac tcg gag gat tcg ccg tac ttc tac ccg act gag ccg tgg | | | | | | | | | | | | | | | | 576 |
| Tyr Leu His Ser Glu Asp Ser Pro Tyr Phe Tyr Pro Thr Glu Pro Trp | | | | | | | | | | | | | | | | |
| | | | 180 | | | | | 185 | | | | | 190 | | | |
| aag act aat ccg gag cac gtg gct cac gtg aag aag gtg act gct cta | | | | | | | | | | | | | | | | 624 |
| Lys Thr Asn Pro Glu His Val Ala His Val Lys Lys Val Thr Ala Leu | | | | | | | | | | | | | | | | |
| | | | 195 | | | | | 200 | | | | | 205 | | | |
| caa cga cta ggg act caa aaa gag ttg ggg gaa ttg gtg gca ttc ctg | | | | | | | | | | | | | | | | 672 |

```
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca      720
Ala Ser Gly Ser Cys Asp Tyr Leu Thr Gly Gln Val Phe Trp Leu Ala
225                 230                 235                 240 ggc ggc ttt ccc att atc gaa cgt tgg ccc ggc atg ccc gaa taa          765
Gly Gly Phe Pro Ile Ile Glu Arg Trp Pro Gly Met Pro Glu *
                245                 250
```

<210> SEQ ID NO 82
<211> LENGTH: 254
<212> TYPE: PRT
<213> ORGANISM: Artificial Sequence
<220> FEATURE:
<223> OTHER INFORMATION: HHDH P016096-G9

<400> SEQUENCE: 82

```
Met Ser Thr Ala Ile Val Thr Asn Val Lys His Phe Gly Gly Met Gly
 1               5                  10                  15

Ser Ala Leu Arg Leu Ser Glu Ala Gly His Thr Val Ala Cys His Asp
                20                  25                  30

Glu Ser Phe Lys Gln Lys Asp Glu Leu Glu Ala Phe Ala Glu Thr Tyr
            35                  40                  45

Pro Gln Leu Lys Pro Met Ser Glu Gln Glu Pro Ala Glu Leu Ile Glu
        50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Glu Asp
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Ile Ile Glu Arg Trp Pro Gly Met Pro Glu
                245                 250
```

<210> SEQ ID NO 83
<211> LENGTH: 765
<212> TYPE: DNA
<213> ORGANISM: Artificial Sequence
<220> FEATURE:
<223> OTHER INFORMATION: HHDH P016097-F9
<220> FEATURE:
<221> NAME/KEY: CDS
<222> LOCATION: (1)...(765)

<400> SEQUENCE: 83

```
atg acc acc gct atc gtc acc aac gtc aaa cat ttt gga ggt atg ggt      48
Met Thr Thr Ala Ile Val Thr Asn Val Lys His Phe Gly Gly Met Gly
1               5                   10                  15 agc gct ctg agg ctg agc gaa gct ggt cat acc gtc gct tgc cat gat      96
Ser Ala Leu Arg Leu Ser Glu Ala Gly His Thr Val Ala Cys His Asp
            20                  25                  30 gaa agc ttt aaa cag aaa gat gaa ctg gaa gct ttt gct gaa acc tac     144
Glu Ser Phe Lys Gln Lys Asp Glu Leu Glu Ala Phe Ala Glu Thr Tyr
        35                  40                  45 cca cag ctg aaa cca atg agc gaa cag gaa cca gct gaa ctg atc gaa     192
Pro Gln Leu Lys Pro Met Ser Glu Gln Glu Pro Ala Glu Leu Ile Glu
    50                  55                  60 gct gtc acc agc gct tac ggt cag gtc gat atc ctg gtc agc aac gat     240
Ala Val Thr Ser Ala Tyr Gly Gln Val Asp Ile Leu Val Ser Asn Asp
65                  70                  75                  80 atc ttt gct cca gaa ttt cag cca atc gat aaa tac gct gtc cag gat     288
Ile Phe Ala Pro Glu Phe Gln Pro Ile Asp Lys Tyr Ala Val Gln Asp
                85                  90                  95 tac agg ggt gct gtc gaa gct ctg cag atc agg cca ttt gct cta gtg     336
Tyr Arg Gly Ala Val Glu Ala Leu Gln Ile Arg Pro Phe Ala Leu Val
            100                 105                 110 aat gct gtg gct tcg caa atg aag aag cga aag tcg ggg cac atc atc     384
Asn Ala Val Ala Ser Gln Met Lys Lys Arg Lys Ser Gly His Ile Ile
        115                 120                 125 ttc atc act tcg gct gct ccg ttc ggg cca tgg aag gag cta tcg act     432
Phe Ile Thr Ser Ala Ala Pro Phe Gly Pro Trp Lys Glu Leu Ser Thr
    130                 135                 140 tac act tcg gct cga gct ggg gct tgt act cta gct aat gct cta tcg     480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat     528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg     576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta     624
Lys Thr Asn Pro Glu His Val Ala His Val Lys Lys Val Thr Ala Leu
        195                 200                 205 caa cga cta ggg act caa aaa gag ttg ggg gaa ttg gtg gca ttt ttg     672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca     720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa         765
Gly Gly Phe Pro Met Ile Glu Arg Trp Pro Gly Met Pro Glu *
                245                 250
```

<210> SEQ ID NO 84
<211> LENGTH: 254
<212> TYPE: PRT
<213> ORGANISM: Artificial Sequence
<220> FEATURE:
<223> OTHER INFORMATION: HHDH P016097-F9

<400> SEQUENCE: 84

```
Met Thr Thr Ala Ile Val Thr Asn Val Lys His Phe Gly Gly Met Gly
1               5                   10                  15
```

```
Ser Ala Leu Arg Leu Ser Glu Ala Gly His Thr Val Ala Cys His Asp
            20                  25                  30

Glu Ser Phe Lys Gln Lys Asp Glu Leu Glu Ala Phe Ala Glu Thr Tyr
        35                  40                  45

Pro Gln Leu Lys Pro Met Ser Glu Gln Glu Pro Ala Glu Leu Ile Glu
    50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Gln Asp
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
            115                 120                 125

Phe Ile Thr Ser Ala Ala Pro Phe Gly Pro Trp Lys Glu Leu Ser Thr
        130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250
```

<210> SEQ ID NO 85
<211> LENGTH: 765
<212> TYPE: DNA
<213> ORGANISM: Artificial Sequence
<220> FEATURE:
<223> OTHER INFORMATION: HHDH P016097-H10
<220> FEATURE:
<221> NAME/KEY: CDS
<222> LOCATION: (1)...(765)

<400> SEQUENCE: 85

```
atg acc acc gct atc gtc acc aac gtc aaa cat ttt gga ggt atg ggt      48
Met Thr Thr Ala Ile Val Thr Asn Val Lys His Phe Gly Gly Met Gly
 1               5                  10                  15 agc gct ctg agg ctg agc gaa gct ggt cat acc gtc gct tgc cat gat      96
Ser Ala Leu Arg Leu Ser Glu Ala Gly His Thr Val Ala Cys His Asp
            20                  25                  30 gaa agc ttt aaa cag aaa gat gaa ctg gaa gct ttt gct gaa acc tac     144
Glu Ser Phe Lys Gln Lys Asp Glu Leu Glu Ala Phe Ala Glu Thr Tyr
        35                  40                  45 cca cag ctg aaa cca atg agc gaa cag gaa cca gct gaa ctg atc gaa     192
Pro Gln Leu Lys Pro Met Ser Glu Gln Glu Pro Ala Glu Leu Ile Glu
    50                  55                  60 gct gtc acc agc gct tac ggt cag gtc gat gtc ctg gtc agc aac gat     240
Ala Val Thr Ser Ala Tyr Gly Gln Val Asp Val Leu Val Ser Asn Asp
65                  70                  75                  80
```

```
atc ttt gct cca gaa ttt cag cca atc gat aaa tac gct gtc cag gat    288
Ile Phe Ala Pro Glu Phe Gln Pro Ile Asp Lys Tyr Ala Val Gln Asp
             85                  90                  95 tac agg ggt gct gtc gaa gct ctg cag atc agg cca ttt gct cta gtg    336
Tyr Arg Gly Ala Val Glu Ala Leu Gln Ile Arg Pro Phe Ala Leu Val
        100                 105                 110 aat gct gtg gct tcg caa atg aag aag cga aag tcg ggg cac atc atc    384
Asn Ala Val Ala Ser Gln Met Lys Lys Arg Lys Ser Gly His Ile Ile
    115                 120                 125 ttc atc act tcg gct gct ccg ttc ggg cca tgg aag gag cta tcg act    432
Phe Ile Thr Ser Ala Ala Pro Phe Gly Pro Trp Lys Glu Leu Ser Thr
130                 135                 140 tac act tcg gct cga gct ggg gct tgt tcc cta gct aat gct cta tcg    480
Tyr Thr Ser Ala Arg Ala Gly Ala Cys Ser Leu Ala Asn Ala Leu Ser
145                 150                 155                 160 aag gag cta gga gag tac aat atc ccg gtg ttc gct atc ggg ccg aat    528
Lys Glu Leu Gly Glu Tyr Asn Ile Pro Val Phe Ala Ile Gly Pro Asn
                165                 170                 175 tac cta cac tcg gag gat tcg ccg tac ttc tac ccg act gag ccg tgg    576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta    624
Lys Thr Asn Pro Glu His Val Ala His Val Lys Lys Val Thr Ala Leu
        195                 200                 205 caa cga cta ggg act caa aaa gag ttg ggg gaa ttg gtg gca ttt ttg    672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca    720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa        765
Gly Gly Phe Pro Met Ile Glu Arg Trp Pro Gly Met Pro Glu *
                245                 250

<210> SEQ ID NO 86
<211> LENGTH: 254
<212> TYPE: PRT
<213> ORGANISM: Artificial Sequence
<220> FEATURE:
<223> OTHER INFORMATION: HHDH P016097-H10

<400> SEQUENCE: 86

Met Thr Thr Ala Ile Val Thr Asn Val Lys His Phe Gly Met Gly
 1               5                  10                  15

Ser Ala Leu Arg Leu Ser Glu Ala Gly His Thr Val Ala Cys His Asp
            20                  25                  30

Glu Ser Phe Lys Gln Lys Asp Glu Leu Glu Ala Phe Ala Glu Thr Tyr
        35                  40                  45

Pro Gln Leu Lys Pro Met Ser Glu Gln Glu Pro Ala Glu Leu Ile Glu
    50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Gln Asp
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
```

```
       130                 135                 140
Tyr Thr Ser Ala Arg Ala Gly Ala Cys Ser Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250

<210> SEQ ID NO 87
<211> LENGTH: 765
<212> TYPE: DNA
<213> ORGANISM: Artificial Sequence
<220> FEATURE:
<223> OTHER INFORMATION: HHDH P016099-A1
<220> FEATURE:
<221> NAME/KEY: CDS
<222> LOCATION: (1)...(765)

<400> SEQUENCE: 87 atg acc acc gct atc gtc acc aac gtc aaa cat ttt gga ggt atg ggt      48
Met Thr Thr Ala Ile Val Thr Asn Val Lys His Phe Gly Gly Met Gly
 1               5                  10                  15 agc gct ctg agg ctg agc gaa gct ggt cat acc gtc gct tgc cat gat      96
Ser Ala Leu Arg Leu Ser Glu Ala Gly His Thr Val Ala Cys His Asp
                20                  25                  30 gaa agc ttt aaa cag aaa gat gaa ctg gaa gct ttt gct gaa acc tac     144
Glu Ser Phe Lys Gln Lys Asp Glu Leu Glu Ala Phe Ala Glu Thr Tyr
            35                  40                  45 cca cag ctg aaa cca atg agc gaa cag gaa cca gct gaa ctg atc gaa     192
Pro Gln Leu Lys Pro Met Ser Glu Gln Glu Pro Ala Glu Leu Ile Glu
        50                  55                  60 gct gtc acc agc gct tac ggt cag gtc gat atc ctg gtc agc aac gat     240
Ala Val Thr Ser Ala Tyr Gly Gln Val Asp Ile Leu Val Ser Asn Asp
 65                 70                  75                  80 atc ttt gct cca gaa ttt cag cca atc gat aaa tac gct gtc cag gat     288
Ile Phe Ala Pro Glu Phe Gln Pro Ile Asp Lys Tyr Ala Val Gln Asp
                85                  90                  95 tac agg ggt gct gtc gaa gct ctg cag atc agg cca ttt gct cta gtg     336
Tyr Arg Gly Ala Val Glu Ala Leu Gln Ile Arg Pro Phe Ala Leu Val
            100                 105                 110 aat gct gtg gct tcg caa atg aag aag cga aag tcg ggg cac atc atc     384
Asn Ala Val Ala Ser Gln Met Lys Lys Arg Lys Ser Gly His Ile Ile
        115                 120                 125 ttc atc act tcg gct gct ccg ttc ggg cca tgg aag gag cta tcg act     432
Phe Ile Thr Ser Ala Ala Pro Phe Gly Pro Trp Lys Glu Leu Ser Thr
    130                 135                 140 tac act tcg gct cga gct ggg gct tgt act cta gct aat gct cta tcg     480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat     528
Lys Glu Leu Gly Glu Tyr Asn Ile Pro Val Phe Ala Ile Gly Pro Asn
                165                 170                 175
```

```
tac cta cac tcg gag gat tcg ccg tac ttc tac ccg act gag ccg tgg        576
Tyr Leu His Ser Glu Asp Ser Pro Tyr Phe Tyr Pro Thr Glu Pro Trp
        180                 185                 190 aag act aat ccg gag cac gtg gct cac gtg aag aag gtg act gct cta        624
Lys Thr Asn Pro Glu His Val Ala His Val Lys Lys Val Thr Ala Leu
            195                 200                 205 caa cga cta ggg act caa aaa gag ttg ggg gaa ttg gtg gca ttt ttg        672
Gln Arg Leu Gly Thr Gln Lys Glu Leu Gly Glu Leu Val Ala Phe Leu
        210                 215                 220 gca tct ggc tct tgt gat tat ttg act ggc cag gtg ttt tgg ttg gca        720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa            765
Gly Gly Phe Pro Met Ile Glu Arg Trp Pro Gly Met Pro Glu *
                245                 250

<210> SEQ ID NO 88
<211> LENGTH: 254
<212> TYPE: PRT
<213> ORGANISM: Artificial Sequence
<220> FEATURE:
<223> OTHER INFORMATION: HHDH P016099-A1

<400> SEQUENCE: 88

Met Thr Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys Gln Lys Asp Glu Leu Glu Ala Phe Ala Glu Thr Tyr
        35                  40                  45

Pro Gln Leu Lys Pro Met Ser Glu Gln Glu Pro Ala Glu Leu Ile Glu
    50                  55                  60

Ala Val Thr Ser Ala Tyr Gly Gln Val Asp Ile Leu Val Ser Asn Asp
65                  70                  75                  80

Ile Phe Ala Pro Glu Phe Gln Pro Ile Asp Lys Tyr Ala Val Gln Asp
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250
```

```
<210> SEQ ID NO 89
<211> LENGTH: 765
<212> TYPE: DNA
<213> ORGANISM: Artificial Sequence
<220> FEATURE:
<223> OTHER INFORMATION: HHDH P016231-A-03
<220> FEATURE:
<221> NAME/KEY: CDS
<222> LOCATION: (1)...(765)

<400> SEQUENCE: 89 atg agc acc gct atc gtc acc aac gtc aaa cat ttt gga ggt atg ggt      48
Met Ser Thr Ala Ile Val Thr Asn Val Lys His Phe Gly Gly Met Gly
 1               5                  10                  15 agc gct ctg agg ctg agc gaa gct ggt cat acc gtc gct tgc cat gat      96
Ser Ala Leu Arg Leu Ser Glu Ala Gly His Thr Val Ala Cys His Asp
             20                  25                  30 gaa agc ttt aaa cag aaa gat gaa ctg gaa gct ttt gct gaa acc tac     144
Glu Ser Phe Lys Gln Lys Asp Glu Leu Glu Ala Phe Ala Glu Thr Tyr
         35                  40                  45 cca cag ctg aaa cca atg agc gaa cag gaa cca gct gaa ctg atc gaa     192
Pro Gln Leu Lys Pro Met Ser Glu Gln Glu Pro Ala Glu Leu Ile Glu
     50                  55                  60 gct gtc acc agc gct tac ggt cag gtc gat gtc ctg gtc agc aac gat     240
Ala Val Thr Ser Ala Tyr Gly Gln Val Asp Val Leu Val Ser Asn Asp
 65                  70                  75                  80 atc ttt gct tca gaa ttt cag cca atc gat aaa tac gcc gtc gaa gat     288
Ile Phe Ala Ser Glu Phe Gln Pro Ile Asp Lys Tyr Ala Val Glu Asp
                 85                  90                  95 tac agg ggt gct gtc gaa gct ctg cag atc agg cca ttt gct cta gtg     336
Tyr Arg Gly Ala Val Glu Ala Leu Gln Ile Arg Pro Phe Ala Leu Val
            100                 105                 110 aat gct gtg gct tcg caa atg aag aag cga aag tcg ggg cac atc atc     384
Asn Ala Val Ala Ser Gln Met Lys Lys Arg Lys Ser Gly His Ile Ile
        115                 120                 125 ttc atc act tcg gct act ccg ttc ggg cca tgg aag gag cta tcg act     432
Phe Ile Thr Ser Ala Thr Pro Phe Gly Pro Trp Lys Glu Leu Ser Thr
    130                 135                 140 tac act tcg gct cga gct ggg gct tgt act cta gct aat gct cta tcg     480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat     528
Lys Glu Leu Gly Glu Tyr Asn Ile Pro Val Phe Ala Ile Gly Pro Asn
                165                 170                 175 tat cta cac tcg gag gat tcg ccg tac ttc tac ccg act gag ccg tgg     576
Tyr Leu His Ser Glu Asp Ser Pro Tyr Phe Tyr Pro Thr Glu Pro Trp
            180                 185                 190 aag act aat ccg gag cac gtg gct cac gtg aag aag gtg act gct cta     624
Lys Thr Asn Pro Glu His Val Ala His Val Lys Lys Val Thr Ala Leu
        195                 200                 205 caa cga cta ggg act caa aaa gag ttg ggg gaa ttg gtg gca ttt ttg     672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca     720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa         765
Gly Gly Phe Pro Met Ile Glu Arg Trp Pro Gly Met Pro Glu *
                245                 250

<210> SEQ ID NO 90
```

-continued

<211> LENGTH: 254
<212> TYPE: PRT
<213> ORGANISM: Artificial Sequence
<220> FEATURE:
<223> OTHER INFORMATION: HHDH P016231-A-03

<400> SEQUENCE: 90

```
Met Ser Thr Ala Ile Val Thr Asn Val Lys His Phe Gly Gly Met Gly
 1               5                  10                  15

Ser Ala Leu Arg Leu Ser Glu Ala Gly His Thr Val Ala Cys His Asp
            20                  25                  30

Glu Ser Phe Lys Gln Lys Asp Glu Leu Glu Ala Phe Ala Glu Thr Tyr
        35                  40                  45

Pro Gln Leu Lys Pro Met Ser Glu Gln Glu Pro Ala Glu Leu Ile Glu
    50                  55                  60

Ala Val Thr Ser Ala Tyr Gly Gln Val Asp Val Leu Val Ser Asn Asp
65                  70                  75                  80

Ile Phe Ala Ser Glu Phe Gln Pro Ile Asp Lys Tyr Ala Val Glu Asp
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
    130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250
```

<210> SEQ ID NO 91
<211> LENGTH: 765
<212> TYPE: DNA
<213> ORGANISM: Artificial Sequence
<220> FEATURE:
<223> OTHER INFORMATION: HHDH P016231-E-03
<220> FEATURE:
<221> NAME/KEY: CDS
<222> LOCATION: (1)...(765)

<400> SEQUENCE: 91

```
atg agc acc gct atc gtc acc aac gtc aag cat ttt gga ggt atg ggt        48
Met Ser Thr Ala Ile Val Thr Asn Val Lys His Phe Gly Gly Met Gly
 1               5                  10                  15 agc gct ctg agg ctg agc gaa gct ggt cat acc gtc gct tgc cat gat        96
Ser Ala Leu Arg Leu Ser Glu Ala Gly His Thr Val Ala Cys His Asp
            20                  25                  30 gaa agc ttt aaa cag aaa gat gaa ctg gaa gct ttt gct gaa acc tac       144
Glu Ser Phe Lys Gln Lys Asp Glu Leu Glu Ala Phe Ala Glu Thr Tyr
```

```
            35                  40                  45
cca cag ctg aaa cca atg agc gaa cag gaa cca gct gaa ctg atc gaa    192
Pro Gln Leu Lys Pro Met Ser Glu Gln Glu Pro Ala Glu Leu Ile Glu
    50                  55                  60 gct gtc acc agc gct tac ggt cag gtc gat gtc ctg gtc agc aac gat    240
Ala Val Thr Ser Ala Tyr Gly Gln Val Asp Val Leu Val Ser Asn Asp
65                  70                  75                  80 atc ttt gct cca gaa ttt cag cca atc gat aaa tac gct gtc gaa gat    288
Ile Phe Ala Pro Glu Phe Gln Pro Ile Asp Lys Tyr Ala Val Glu Asp
                85                  90                  95 tac agg ggt gct gtc gaa gct ctg cag atc agg cca ttt gct cta gtg    336
Tyr Arg Gly Ala Val Glu Ala Leu Gln Ile Arg Pro Phe Ala Leu Val
            100                 105                 110 aat gct gtg gct tcg caa atg aag aag cga aag tcg ggg cac atc atc    384
Asn Ala Val Ala Ser Gln Met Lys Lys Arg Lys Ser Gly His Ile Ile
        115                 120                 125 ttc atc act tcg gct act ccg ttc ggg cca tgg aag gag cta tcg act    432
Phe Ile Thr Ser Ala Thr Pro Phe Gly Pro Trp Lys Glu Leu Ser Thr
    130                 135                 140 tac act tcg gct cga gct ggg gct tgt act cta gct aat gct cta tcg    480
Tyr Thr Ser Ala Arg Ala Gly Ala Cys Thr Leu Ala Asn Ala Leu Ser
145                 150                 155                 160 aag gag cta gga gag tac aat atc ccg gtg ttc gct atc ggg ccg aat    528
Lys Glu Leu Gly Glu Tyr Asn Ile Pro Val Phe Ala Ile Gly Pro Asn
                165                 170                 175 tac cta cac tcg gag gat tcg ccg tac tat tat ccg act gag ccg tgg    576
Tyr Leu His Ser Glu Asp Ser Pro Tyr Tyr Tyr Pro Thr Glu Pro Trp
            180                 185                 190 aag act aat ccg gag cac gtg gct cac gtg aag aag gtg act gct cta    624
Lys Thr Asn Pro Glu His Val Ala His Val Lys Lys Val Thr Ala Leu
        195                 200                 205 caa cga cta ggg act caa aaa gag ttg ggg gaa ttg gtg gca ttt ttg    672
Gln Arg Leu Gly Thr Gln Lys Glu Leu Gly Glu Leu Val Ala Phe Leu
    210                 215                 220 gca tct ggc tct tgt gat tat ttg act ggc cag gtg ttt tgg ttg gca    720
Ala Ser Gly Ser Cys Asp Tyr Leu Thr Gly Gln Val Phe Trp Leu Ala
225                 230                 235                 240 ggc ggc ttt ccc atg ata gaa cgt tgg ccc ggc atg ccc gaa taa        765
Gly Gly Phe Pro Met Ile Glu Arg Trp Pro Gly Met Pro Glu *
                245                 250
```

<210> SEQ ID NO 92
<211> LENGTH: 254
<212> TYPE: PRT
<213> ORGANISM: Artificial Sequence
<220> FEATURE:
<223> OTHER INFORMATION: HHDH P016231-E-03

<400> SEQUENCE: 92

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys Gln Lys Asp Glu Leu Glu Ala Phe Ala Glu Thr Tyr
        35                  40                  45

Pro Gln Leu Lys Pro Met Ser Glu Gln Glu Pro Ala Glu Leu Ile Glu
    50                  55                  60

Ala Val Thr Ser Ala Tyr Gly Gln Val Asp Val Leu Val Ser Asn Asp
65                  70                  75                  80
```

```
Ile Phe Ala Pro Glu Phe Gln Pro Ile Asp Lys Tyr Ala Val Glu Asp
            85                  90              95

Tyr Arg Gly Ala Val Glu Ala Leu Gln Ile Arg Pro Phe Ala Leu Val
            100             105             110

Asn Ala Val Ala Ser Gln Met Lys Lys Arg Lys Ser Gly His Ile Ile
        115             120             125

Phe Ile Thr Ser Ala Thr Pro Phe Gly Pro Trp Lys Glu Leu Ser Thr
    130             135             140

Tyr Thr Ser Ala Arg Ala Gly Ala Cys Thr Leu Ala Asn Ala Leu Ser
145                 150             155                 160

Lys Glu Leu Gly Glu Tyr Asn Ile Pro Val Phe Ala Ile Gly Pro Asn
            165             170             175

Tyr Leu His Ser Glu Asp Ser Pro Tyr Tyr Pro Thr Glu Pro Trp
            180             185             190

Lys Thr Asn Pro Glu His Val Ala His Val Lys Lys Val Thr Ala Leu
        195             200             205

Gln Arg Leu Gly Thr Gln Lys Glu Leu Gly Glu Leu Val Ala Phe Leu
    210             215             220

Ala Ser Gly Ser Cys Asp Tyr Leu Thr Gly Gln Val Phe Trp Leu Ala
225             230             235             240

Gly Gly Phe Pro Met Ile Glu Arg Trp Pro Gly Met Pro Glu
            245             250
```

ENZYMATIC PROCESSES FOR THE PRODUCTION OF 4-SUBSTITUTED 3-HYDROXYBUTYRIC ACID DERIVATIVES

CROSS-REFERENCE TO RELATED APPLICATION

This application claims the benefit under 35 U.S.C. § 119(e) of U.S. Ser. No. 60/402,436, filed Aug. 9, 2002, which is incorporated herein by reference in its entirety.

COPYRIGHT NOTIFICATION

A portion of the disclosure of this patent document contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

Field of the Invention

The present invention relates to novel enzymatic methods and compositions for preparing 4-substituted 3-hydroxybutyric acid derivatives.

BACKGROUND 4-substituted 3-hydroxybutyric acid derivatives are commercially important intermediates in the synthesis of pharmaceuticals. Nonracemic chiral 4-substituted 3-hydroxybutyric acid esters maybe utilized in the synthesis of HMG-CoA reductase inhibitors, such as atorvastatin, fluvastatin, rosuvastatin, and itavastatin. For example, an ester of (R)-4-cyano-3-hydroxybutyric acid is a key intermediate for the production of the cholesterol lowering agent atorvastatin. Methods have been described for producing certain 4-substituted 3-hydroxybutyric acid esters. Isbell, et al., *Carbohydrate Res.*, 72:301 (1979), report a method for synthesizing an (R)-4-cyano-3-hydroxybutyric acid ester by reacting the monohydrate calcium salt of threonine with hydrogen bromide to produce a dibromo derivative of threonine, which is then converted to a vicinal bromohydrin. The hydroxyl group of the bromohydrin is protected prior to reaction with sodium cyanide. Id.

*Acta Chem. Scand.*, B37, 341 (1983) reports a method for producing a 4-cyano-3-hydroxybutyrate from a 4-bromo-3-hydroxybutyrate that requires protecting the hydroxy group with a protecting group prior to reaction with sodium cyanide. Recent routes to synthesize 4-cyano-3-hydroxybutyrate esters involve the uncatalyzed chemical reaction of a 4-bromo- or 4-chloro-3-hydroxybutyrate ester, without protection of the hydroxyl group, with a cyanide salt. By-products, however, are formed under the basic conditions created by the basic cyanide anion, which are particularly problematic to remove from the product. 4-Cyano-3-hydroxybutyrate esters are high boiling liquids and vacuum fractional distillation is required to separate the 4-cyano-3-hydroxybutyrate ester from these by-products. The distillation conditions are prone to generate additional by-products and the distillation is troublesome to operate successfully.

The use of a 4-chloro-3-hydroxybutyric acid ester as a starting material in the synthesis of a 4-cyano-3-hydroxybutyric acid ester is more economically attractive than the use of a 4-bromo-3-hydroxybutyric acid ester, but requires more forcing conditions in its reaction with cyanide salts due to the lower reactivity of the chloro substituent compared to the bromo substituent. While the cyanation of 4-chloro-3-hydroxybutyrate esters proceeds with alkali cyanide and high temperature, these forcing conditions lead to substantial by-product formation, requiring extensive isolation and purification procedures that result in additional yield loss. U.S. Pat. No. 5,908,953 discloses that, besides unreacted starting material, crude lower alkyl esters of (R)-4-cyano-3-hydroxybutyric acid may contain hydroxyacrylate, cyanoacrylate, 3-cyanobutyrolactone, 3-hydroxybutyrolactone, γ-crotonolactone, 3-cyano-4-hydroxybutyrate lower alkyl ester, 3,4-dicyanobutyrate lower alkyl ester and high-boiling uncharacterized compounds. U.S. Pat. No. 5,908,953 further describes a purification method for lower alkyl esters of (R)-4-cyano-3-hydroxybutyric acid that involves distillation of a crude mixture in the presence of a solvent that has a boiling point of 50° C. to 160° C. at 10 Torr. Using such distillation methods, the decomposition of unreacted starting material is said to be minimized, which otherwise can result in a dramatic overall loss in (R)-4-cyano-3-hydroxybutyric acid lower alkyl ester production. U.S. Pat. No. 6,140,527 describes an alternative approach for treating crude lower alkyl esters of (R)-4-cyano-3-hydroxybutyric acid that involves removal of the dehydrated by-products, such as 4-hydroxycrotonic acid esters, by chemical reaction, which renders these components water soluble and extractable. Thus, although these methods utilize a readily available starting material, significant yield loss and product purification requirements make them commercially undesirable. Accordingly, more efficient methods for producing nonracemic chiral 4-substituted 3-hydroxybutyric acid esters under milder conditions would be highly desirable.

Halohydrin dehalogenases, also referred to as haloalcohol dehalogenases or halohydrin hydrogen-halide lyases, catalyze the elimination of hydrogen halide, as proton and halide ion, from vicinal halohydrins to produce the corresponding epoxide. These enzymes also catalyze the reverse reaction. Nagasawa et al., *Appl. Microbiol. Biotechnol.* vol. 36 (1992) pp. 478–482, disclose activity of a certain halohydrin hydrogen-halide lyase on 4-chloro-3-hydroxybutyronitrile among other vicinal halohydrins. Nakamura et al., *Biochem. Biophys. Research Comm.* vol. 180 (1991) pp. 124–130 and *Tetrahedron* vol. 50 (1994) pp 11821–11826, disclose activity of a halohydrin hydrogen-halide lyase to catalyze the reaction of certain epoxides with cyanide to form the corresponding beta-hydroxynitriles. In these references and U.S. Pat. No. 5,210,031, Nakamura et al. disclose a reaction of epihalohydrin with alkali cyanide in the presence of a certain halohydrin hydrogen-halide lyase to produce the corresponding 4-halo-3-hydroxy-butyronitrile. In U.S. Pat. No. 5,166,061, Nakamura et al. disclose a reaction of a 1,3-dihalo-2-propanol with alkali cyanide in the presence of certain dehalogenating enzymes to produce the corresponding 4-halo-3-hydroxybutyronitrile. In *Tetrahedron* vol. 50 (1994) pp 11821–11826, Nakamura et al. disclose the reaction of 1,3-dichloro-2-propanol with cyanide using a purified halohydrin hydrogen-halide lyase to produce 4-chloro-3-hydroxybutyronitrile.

Lutje-Spelberg et al., *Org. Lett.*, vol. 2 (2001) pp 41–43, discloses activity of a halohydrin dehalogenase to catalyze the reaction of certain styrene oxides with azide to form the corresponding 1-phenyl-2-azido-ethanol.

SUMMARY OF THE INVENTION

In one aspect, the present invention is directed to a method for producing a 4-cyano-3-hydroxybutyric acid ester or amide from a 4-halo-3-hydroxybutyric acid ester or amide, the method comprising:
(a) providing a 4-halo-3-hydroxybutyric acid ester or amide, wherein the halo substituent is selected from the group consisting of chlorine, bromine, and iodine; and
(b) contacting the 4-halo-3-hydroxybutyric acid ester or amide with a halohydrin dehalogenase and cyanide under conditions sufficient to form a reaction mixture for converting the 4-halo-3-hydroxybutyric acid ester or amide to a 4-cyano-3-hydroxybutyric acid ester or amide.

In a further aspect of the present invention, the 4-halo-3-hydroxybutyric acid ester or amide in step (a) is provided by a method comprising:
providing a 4-halo-3-ketobutyric acid ester or amide, wherein the halo substituent is selected from the group consisting of chlorine, bromine, and iodine; and
contacting the 4-halo-3-ketobutyric acid ester or amide with a ketoreductase, a cofactor, and a cofactor regeneration system under conditions sufficient to form a reaction mixture for converting the 4-halo-3-ketobutyric acid ester or amide to the 4-halo-3-hydroxybutyric acid ester or amide.

In another aspect, the present invention is directed to a method for producing a 4-cyano-3-hydroxybutyric acid ester from a 4-halo-3-ketobutyric acid ester, the method comprising:
(a) providing a 4-halo-3-ketobutyric acid ester, wherein the halo substituent is selected from the group consisting of chlorine, bromine, and iodine; and
(b) contacting the 4-halo-3-ketobutyric acid ester with a ketoreductase, a cofactor, a cofactor regeneration system, cyanide, and a halohydrin dehalogenase to form a reaction mixture for converting the 4-halo-3-ketobutyric acid ester to a 4-cyano-3-hydroxybutyric acid ester.

In another embodiment, the present invention is directed to a method for producing a 4-nucleophile substituted-3-hydroxybutyric acid ester or amide from a 4-halo-3-hydroxybutyric acid ester or amide, the method comprising:
(a) providing a 4-halo-3-hydroxybutyric acid ester or amide, wherein the halo substituent is selected from the group consisting of chlorine, bromine, and iodine; and
(b) contacting the 4-halo-3-hydroxybutyric acid ester or amide with a halohydrin dehalogenase and a nucleophile under conditions suitable to form a reaction mixture for converting the 4-halo-3-hydroxybutyric acid ester or amide to a 4-nucleophile substituted-3-hydroxybutyric acid or amide.

In a further embodiment, the present invention is directed to a method for producing a 4-nucleophile substituted-3-hydroxybutyric acid esters or amide, the method comprising:
(a) providing a 4-halo-3-ketobutyric acid ester or amide wherein the halo substituent is selected from the group consisting of chlorine, bromine, and iodine; and
(b) contacting the 4-halo-3-ketobutyric acid ester or amide with a ketoreductase, a cofactor, a cofactor regeneration system, a nucleophile, and a halohydrin dehalogenase to form a reaction mixture for converting the 4-halo-3-ketobutyric acid ester or amide to a 4-nucleophile substituted-3-hydroxybutyric acid ester or amide.

In another aspect, the present invention is directed to a composition comprising:
(a) a halohydrin dehalogenase;
(b) a nucleophile; and
(c) a 4-halo-3-hydroxybutyric acid ester or amide.

DETAILED DESCRIPTION OF THE INVENTION

Figure 1:
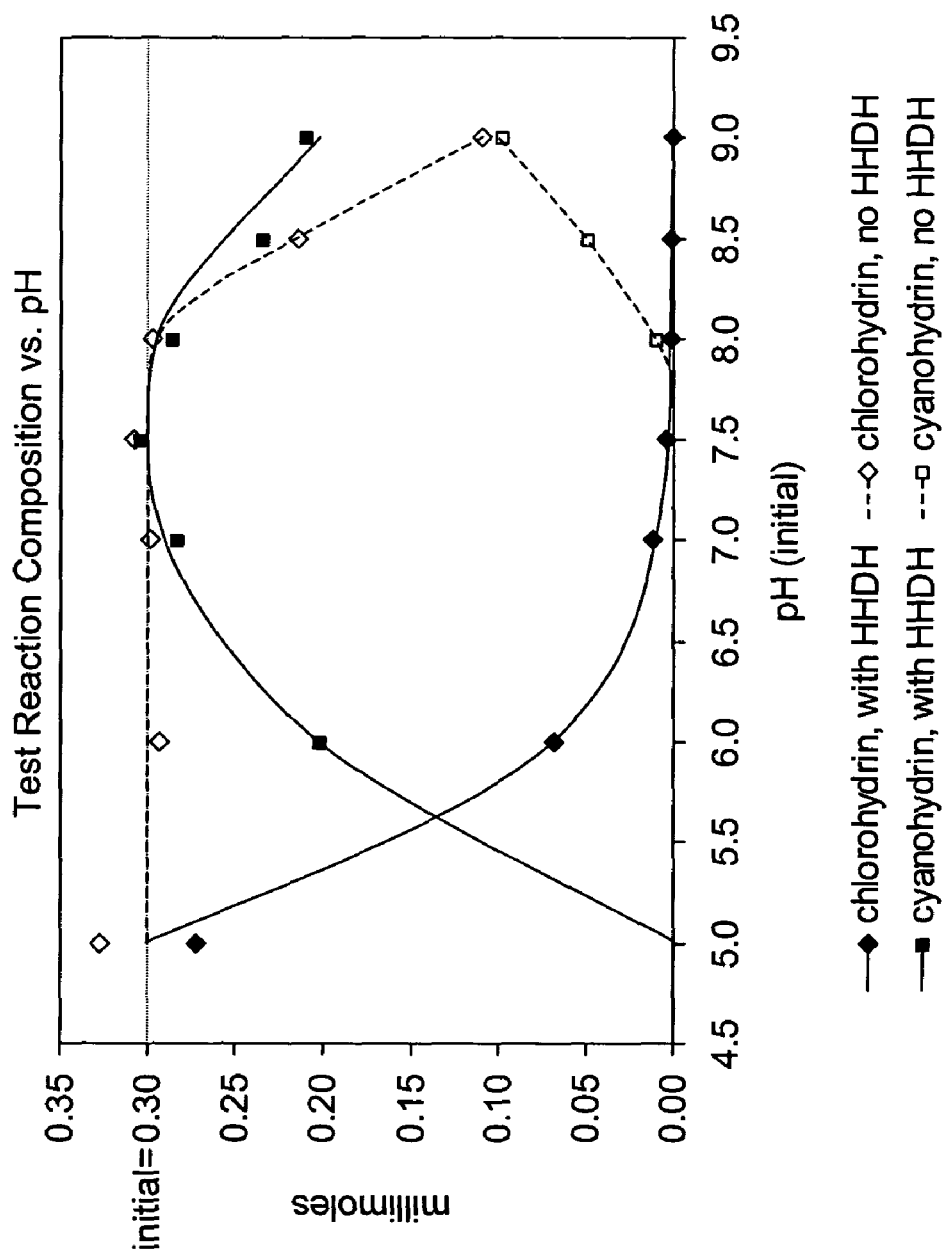
FIG. 1 depicts the amounts of ethyl 4-chloro-3-hydroxybutyrate (chlorohydrin) and ethyl 4-cyano-3-hydroxybutyrate (cyanohydrin) analyzed in test reactions of ethyl 4-chloro-3-hydroxybutyrate with cyanide in aqueous solutions at various pHs in the presence or absence of a halohydrin dehalogenase (HHDH), as described in Example 21.

The present invention provides enzymatic methods for producing various 4-substituted 3-hydroxybutyric acid esters and amides from corresponding 4-halo-3-hydroxybutyric acid ester and amide substrates.

I. Halohydrin Dehalogenase-Catalyzed Conversion of 4-Halo-3-Hydroxybutyric Acid Derivatives The present invention provides a method for producing a 4-nucleophile substituted-3-hydroxybutyric acid ester or amide from a 4-halo-3-hydroxybutyric acid ester or amide, the method comprising:
(a) providing a 4-halo-3-hydroxybutyric acid ester or amide,
wherein the halo substituent is selected from the group consisting of chlorine, bromine, and iodine; and
(b) contacting the 4-halo-3-hydroxybutyric acid ester or amide with a halohydrin dehalogenase and a nucleophile under conditions suitable to form a reaction mixture for converting the 4-halo-3-hydroxybutyric acid ester or amide to a 4-nucleophile substituted-3-hydroxybutyric acid ester or amide. Significantly, the invention method provides a process for the manufacture of 4-substituted 3-hydroxybutyric acid esters and amides in which by-product formation is minimized.

Nucleophiles suitable for use in the practice of the present invention are those that are capable of displacing the halo substituent of the 4-halo-3-hydroxybutyric acid ester or amide substrate. Typical nucleophiles utilized in the present invention are anionic nucleophiles. Exemplary nucleophiles include cyanide ($CN^-$), azide ($N_3^-$), and nitrite ($ONO^-$).

In a specific embodiment, the present invention provides a method for producing 4-cyano-3-hydroxybutyric acid esters or amides from 4-halo-3-hydroxybutyric acid esters or amides via a halohydrin dehalogenase-catalyzed reaction, the method comprising:
(a) providing a 4-halo-3-hydroxybutyric acid ester or amide;
wherein the halo substituent is selected from the group consisting of chlorine, bromine, and iodine; and
(b) contacting the 4-halo-3-hydroxybutyric acid ester or amide with a halohydrin dehalogenase and cyanide under conditions suitable to form a reaction mixture for converting the 4-halo-3-hydroxybutyric acid ester or amide to a 4-cyano-3-hydroxybutyric acid ester or amide.

As used herein, the term "cyanide" refers to cyanide anion (CN⁻), hydrocyanic acid (HCN), and mixtures thereof. Cyanide may be provided in the form of a cyanide salt, typically an alkali salt (for example, NaCN, KCN, and the like), in the form of hydrocyanic acid (gaseous or in solution), or mixtures thereof.

4-halo-3-hydroxybutyric acid esters and amides employed in the practice of the present invention may be prepared according to the methods described herein, or alternatively, using methods that are well known to those having ordinary skill in the art. Such methods are described, for example, in U.S. Pat. No. 5,891,685; Hallinan, et al., *Biocatalysis and Biotransformation*, 12:179–191 (1995); *Russ. Chem. Rev.*, 41:740 (1972); Kataoka, et al., *Appl. Microbiol. Biotechnol.*, 48:699–703 (1997); and U.S. Pat. No. 5,430,171.

Suitable 4-halo-3-hydroxybutyric acid ester and amide substrates employed in the practice of the present invention include those having the structure IA and IB, respectively:

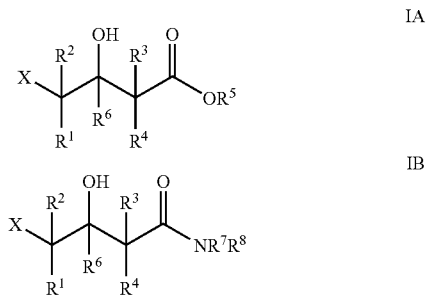

wherein:
- X is a halogen selected from the group consisting of chlorine, bromine, and iodine;
- $R^1$, $R^2$, $R^3$, $R^4$, and $R^6$ are each independently selected from the group consisting of hydrogen, fluorine, an optionally substituted lower alkyl, an optionally substituted cycloalkyl, an optionally substituted lower alkenyl, an optionally substituted aryl, an optionally substituted arylalkyl, amino, an optionally substituted lower alkylamino, an optionally substituted cycloalkylamino, an optionally substituted lower alkoxy, an optionally substituted cycloalkoxy, an optionally substituted aryloxy, and an optionally substituted arylalkoxy; and
- $R^5$ is selected from the group consisting of an optionally substituted lower alkyl, an optionally substituted cycloalkyl, an optionally substituted aryl, and an optionally substituted arylalkyl; and
- $R^7$ and $R^8$ are each independently selected from the group consisting of hydrogen, an optionally substituted lower alkyl, an optionally substituted cycloalkyl, an optionally substituted aryl, and an optionally substituted arylalkyl.

"Optionally substituted" refers herein to the replacement of hydrogen with a monovalent radical. Suitable substitution groups include, for example, hydroxyl, alkyl, a lower alkyl, an alkoxy, a lower alkoxy, an alkenyl, a lower alkenyl, nitro, amino, cyano, halogen (i.e., halo), thio, and the like.

The term "lower alkyl" is used herein to refer to branched or straight chain alkyl groups having from one to about six carbon atoms that are unsubstituted or substituted, e.g., with one or more halo, hydroxyl or other groups, including, e.g., methyl, ethyl, propyl, isopropyl, n-butyl, i-butyl, t-butyl, trifluoromethyl, and the like. The term "cycloalkyl" refers to carbocyclic alkyl moieties having from three to about 6 carbon atoms, as well as heterocyclic alkyl moieties having from three to about 6 atoms, where at least one ring atom is a heteroatom, and the other atoms are carbon atoms. "Heteroatom" refers herein to oxygen, nitrogen, or sulfur.

The term "lower alkenyl" is used herein to refer to a branched or straight chain group having one or more double bonds and from 2 to about 6 carbon atoms. Lower alkenyl groups employed in the practice of the present invention may be optionally substituted with the groups described herein, including, for example, halo, hydroxyl, lower alkyl, and the like.

As used herein, the term "lower alkoxy" refers to —OR where R is a lower alkyl or a lower alkenyl. Suitable lower alkoxy groups employed in the practice of the present invention include methoxy, ethoxy, t-butoxy, trifluoromethoxy, and the like. The term "aryloxy" refers herein to RO—, where R is an aryl. As used herein, the term "aryl" refers to monocyclic and polycyclic aromatic groups having from 3 to about 14 backbone carbon or heteroatoms, and includes both carbocyclic aryl groups and heterocyclic aryl groups. Carbocyclic aryl groups are aryl groups in which all ring atoms in the aromatic ring are carbon. Heterocyclic aryl groups are aryl groups that have from 1 to about 4 heteroatoms as ring atoms in an aromatic ring with the remainder of the ring atoms being carbon atoms. Exemplary aryl groups employed as substituents in the present invention include, for example, phenyl, pyridyl, pyrimidinyl, naphthyl, and the like.

The term "arylalkyl" refers herein to an alkyl group substituted with an aryl group. Exemplary arylalkyl groups include benzyl, picolyl, and the like. Substituted arylalkyl groups may be substituted in either or both aryl and alkyl portions of the arylalkyl group. As used herein, the term "arylalkoxy" refers to RO— where R is an arylalkyl.

The term "cycloalkoxy" refers herein to RO—, where R is an optionally substituted $C_3$–$C_8$ cycloalkyl. The term "amino" is used herein to refer to the group —NH₂. The term "lower alkylamino" refers herein to the group —NRR' where R is hydrogen or a lower alkyl, and R' is a lower alkyl. The term "cycloalkylamino" refers herein to the group —NR where R is an optionally substituted divalent aliphatic radical having from 3 to about 8 carbon atoms, so that N and R form a cyclic structure, for example, pyrollidino, piperidino, and the like.

Specific 4-halo-3-hydroxybutyric acid esters of compound IA that may be employed in the practice of the present invention include ethyl 4-chloro-3-hydroxybutyric acid ester (i.e., where X is chlorine, $R^1$, $R^2$, $R^3$, $R^4$, and $R^6$ are hydrogen, and $R^5$ is ethyl), methyl 4-chloro-3-hydroxybutyric acid ester (i.e., where X is chlorine, $R^1$, $R^2$, $R^3$, $R^4$ and $R^6$ are hydrogen and $R^5$ methyl), ethyl 4-bromo-3-hydroxybutyric acid ester (i.e., where X is bromine, $R^1$, $R^2$, $R^3$, $R^4$, and $R^6$ are hydrogen, and $R^5$ ethyl), methyl 4-bromo-3-hydroxybutyric acid ester (i.e., where X is bromine, $R^1$, $R^2$, $R^3$, $R^4$, and $R^6$ are hydrogen, and $R^5$ methyl), t-butyl-4-chloro-3-hydroxybutyric acid ester (i.e., where X is chlorine, $R^1$, $R^2$, $R^3$, $R^4$, and $R^6$ are hydrogen, and $R^5$ is t-butyl), t-butyl-4-bromo-3-hydroxybutyric acid ester (i.e., where X is bromine, $R^1$, $R^2$, $R^3$, $R^4$, and $R^6$ are hydrogen, and $R^5$ is t-butyl), and t-butyl-4-iodo-3-hydroxybutyric acid ester (i.e., where X is iodine, $R^1$, $R^2$, $R^3$, $R^4$, and $R^6$ are hydrogen, and $R^5$ is t-butyl). In certain embodiments, at least one of $R^1$, $R^2$, $R^3$, $R^4$, and $R^6$ is a lower alkyl, such as, for example, methyl, ethyl, or propyl.

Suitable 4-halo-3-hydroxybutyric acid amides of compound IB that may be employed in the practice of the present invention include 4-chloro-3-hydroxybutyric amide (i.e., where X is chlorine, $R^1$, $R^2$, $R^3$, $R^4$, $R^6$, $R^7$, and $R^8$ are hydrogen), 4-bromo-3-hydroxybutyric amide (i.e., where X is bromine, and $R^1$, $R^2$, $R^3$, $R^4$, $R^6$, $R^7$, and $R^8$ are hydrogen), and 4-iodo-3-hydroxybutyric amide (i.e., where X is iodine, $R^1$, $R^2$, $R^3$, $R^4$, $R^6$, $R^7$, and $R^8$ are hydrogen, In certain embodiments, at least one of $R^1$, $R^2$, $R^3$, $R^4$, and $R_6$ is a lower alkyl, such as, for example, methyl, ethyl, or propyl.

The 4-halo substituent of the 4-halo-3-hydroxybutyric acid ester and amide substrates is preferably selected from chlorine and bromine. Particularly preferred are 4-chloro-3-hydroxybutyric acid ester and amide substrates.

4-substituted-3-hydroxybutyric acid esters and amides produced by the methods of the present invention include those having the structure IIA and IIB, respectively:

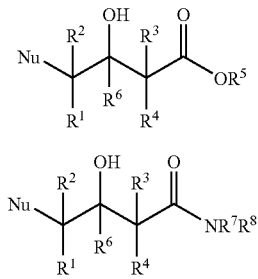

where:
$R^1$, $R^2$, $R^3$, $R^4$, $R^5$, $R^6$, $R^7$, and $R^8$ are as defined for structures IA and IB; and
Nu is selected from the group consisting of —CN, —$N_3$, and —ONO.

When 4-halo-3-hydroxybutyric acid ester substrates having the structure of compound IA are reacted with cyanide and halohydrin dehalogenase, 4-cyano-3-hydroxybutyric acid ester products are generated that have the structure of compound III:

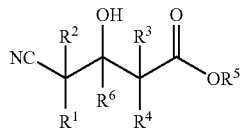

where $R^1$, $R^2$, $R^3$, $R^4$, $R^5$, and $R^6$ are as defined for structure IA.

Halohydrin dehalogenases are employed in the practice of the present invention to catalyze the conversion of a 4-halo-3-hydroxybutyric acid ester or amide to the corresponding 4-nucleophile substituted-3-hydroxybutyric acid ester or amide in the presence of a nucleophile. The terms "halohydrin dehalogenase" and "HHDH" are used interchangeably herein to refer to an enzyme that, in the process of the present invention, catalyzes the conversion of a 4-halo-3-hydroxybutyric acid ester and/or amide to a 4-nucleophile substituted-3-hydroxybutyric acid ester and/or amide, respectively, in the presence of a nucleophile such as cyanide. Suitable halohydrin dehalogenases include naturally occurring (wild type) halohydrin dehalogenases, as well as non-naturally occurring halohydrin dehalogenases generated by human manipulation. Exemplary naturally occurring and non-naturally occurring halohydrin dehalogenases and halohydrin dehalogenase-encoding polynucleotides include those described herein.

Naturally occurring halohydrin dehalogenase encoding genes have been identified in *Agrobacterium radiobacter* AD1 (hheC), *Agrobacterium tumefaciens* (halB), *Corynebacterium* sp. (hheA encoding Ia and hhB encoding Ib), *Arthrobacter* sp. (hheA$_{AD2}$), and *Mycobacterium* sp. GP1 (hheB$_{GP1}$). See van Hylckama Vlieg, J. E. T., L. Tang, J. H. Lutje Spelberg, T. Smilda, G. J. Poelarends, T. Bosma, A. E. J. van Merode, M. W. Fraaije & Dick B. Janssen, "Halohydrin Dehalogenases are structurally and mechanistically related to short-chain dehydrogenases/reductases (2001) *Journal of Bacteriology*, 183:5058–5066 (provides the amino acid sequences for these halohydrin dehalogenases in an alignment).

These naturally occurring halohydrin dehalogenases have been characterized to some extent. HHDH from *Agrobacterium radiobacter* AD1 is a homotetramer of 28 kD subunits. *Corynebacterium* sp. N-1074 produces two HHDH enzymes, one of which is composed of 28 kD subunits (Ia), while the other is composed of related subunits of 35 and/or 32 kD (Kb). HHDH from some sources is easily inactivated under oxidizing conditions in a process that leads to dissociation of the subunits, has a broad pH optimum from pH 8 to 9 and an optimal temperature of 50° C. (Tang, *Enz. Microbiol. Technol.* (2002) 30:251–258; Swanson, *Curr. Opinion Biotechnol.* (1999) 10:365–369). The optimal pH for HHDH catalyzed epoxide formation is 8.0 to 9.0 and the optimal temperature ranges from 45 to 55° C. (Van Hylckama Vlieg, et al., *J. Bacteriol.* (2001) 183:5058–5066; Nakamura, et al., *Appl. Environ. Microbiol.* (1994) 60:1297–1301; Nagasawa, et al., *Appl. Microbiol. Biotechnol.* (1992) 36:478–482). The optimal pH for the reverse reaction, ring opening by chloride has been reported for the two *Cornebacterium* sp. N-1074 enzymes and is 7.4 (Ia) or 5 (Ib). Polynucleotides encoding the halohydrin dehalogenase from *Agrobacterium radiobacter* AD1 are provided herein as SEQ ID NOS: 13, 15, and 17. The polynucleotides corresponding to SEQ ID NOS: 13, 15, and 17 are variants that encode the same amino acid sequence (the translated sequences are provided as SEQ ID NOS: 14, 16, and 18).

Non-naturally occurring halohydrin dehalogenases can be generated using known methods, including, for example, mutagenesis, directed evolution, and the like. Several illustrative methods are described hereinbelow. The enzymes can be readily screened for activity using the method described in Example 4. Such screening methods may also be readily applied to identifying other naturally occurring halohydrin dehalogenases. Suitable non-naturally occurring halohydrin dehalogenases include those corresponding to SEQ ID NOS: 24 (HHDH B-03), 26 (HHIDH C-04), 28 (HHDH E-01), 30 (HHDH G-08) 32 (HHDH 2G5), 34 (HHDH Mz1.1A5), 36 (HHDH cys1.10), 38 (HHDH cys2.12), 74 (HHDH B-12), 76 (HHDH Mz1/4H6), 78 (HHDH F-04), 80 (HHDH A-08), 82 (HHDH G9), 84 (HHDH F9), 86 (HHDH H10), 88 (HHDH A1), 90 (HHDH A-03), and 92 (HHDH E-03). Exemplary polynucleotide sequences that encode these halohydrin dehalogenases include those corresponding to SEQ ID NOS: 23, 25, 27, 29, 31, 33, 35, 37, 73, 75, 77, 79, 81, 83, 85, 87, 89, and 91, respectively. Additional non-naturally occurring halohydrin dehalogenases that are suitable for use in the practice of the present invention are provided in the patent application entitled, "Improved Halohydrin Dehalogenases and Related Polynucleotides," filed on Aug. 11, 2003, and assigned U.S. application Ser. No. 60/494,382, which is incorporated herein by reference in its entirety.

Halohydrin dehalogenases that are suitable for use in the practice of the present invention, whether naturally occurring or non-naturally occurring can be readily identified by those having ordinary skill in the art using the method described in Example 4. Halohydrin dehalogenases employed in the practice of the present invention typically exhibit an activity of at least about 1 μmol/min/mg in the assay described in Example 4, using the 4-halo-3-hydroxybutyric acid ester or amide substrate of interest. Halohydrin dehalogenases employed in the practice of the present invention may exhibit an activity of at least about 10 μmol/min/mg, and sometimes at least about $10^2$ μmol/min/mg, and up to about $10^3$ μmol/min/mg or higher, in the assay described in Example 4.

Halohydrin dehalogenase may be provided to the reaction mixture in the form of purified enzyme, cell extract, cell lysate, or whole cells transformed with gene(s) encoding halohydrin dehalogenase(s). Whole cells transformed with halohydrin dehalogenase encoding genes and/or cell extracts and/or cell lysates thereof may be employed in a variety of different forms, including solid (e.g., lyophilized, spray dried, and the like) or semi-solid (e.g., a crude paste). The cell extracts or cell lysates may be partially purified by precipitation (ammonium sulfate, polyethyleneimine, heat treatment or the like), followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The solid reactants (e.g., enzyme, salts, etc.) may be provided in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a prechilled lyophilization chamber, followed by the application of a vacuum. After the removal of water from the samples, the temperature is typically raised to 4° C. for two hours before release of the vacuum and retrieval of the lyophilized samples.

In carrying out the conversion of 4-halo-3-hydroxybutyric acid ester or amide substrate to the corresponding 4-nucleophile substituted-3-hydroxybutyric ester or amide product, the substrate is typically contacted with the halohydrin dehalogenase and nucleophile in a solvent. Suitable solvents for carrying out the conversion of 4-halo-3-hydroxybutyric acid ester or amide to 4-nucleophile substituted-3-hydroxybutyric acid ester or amide include water, organic solvents (e.g. ethyl acetate, butyl acetate, 1-octanol, heptane, octane, methyl t-butyl ether (MTBE), toluene, and the like), ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like), and co-solvent systems, including aqueous co-solvent systems, and the like. Preferred solvents are aqueous solvents, including water and aqueous co-solvent systems.

Exemplary aqueous co-solvent systems have water and one or more organic solvent. In general, an organic solvent component of an aqueous co-solvent system is selected such that it does not completely inactivate the enzyme catalysts employed in the invention method. Appropriate co-solvent systems can be readily identified by measuring enzyme activity with the substrate of interest in the candidate solvent system, utilizing the enzyme assay described in Example 4.

The organic solvent component of an aqueous co-solvent system may be miscible with the aqueous component, providing a single liquid phase, or may be partly miscible or immiscible with the aqueous component, providing two liquid phases. Typically, when an aqueous co-solvent system is employed, it is selected to be biphasic, with water dispersed in an organic solvent, or vice-versa. Generally, when an aqueous co-solvent system is utilized, it is desirable to select an organic solvent that can be readily separated from the aqueous phase. In general, the ratio of water to organic solvent in the co-solvent system is typically in the range of from about 90:10 to about 10:90 (v/v) organic solvent to water, and between 80:20 and 20:80 (v/v) organic solvent to water. The co-solvent system may be pre-formed prior to addition to the reaction mixture, or it may be formed in situ in the reaction vessel.

The aqueous solvent (water or aqueous co-solvent system) may be pH-buffered or unbuffered. The conversion of the 4-halo-3-hydroxybutyric acid ester or amide to the 4-nucleophile substituted-3-hydroxybutyric acid ester or amide may be carried out at a pH of about 5 or above. Generally, the conversion is carried out at a pH of about 10 or below, usually in the range of from about 5 to about 10. Typically, the conversion is carried out at a pH of about 9 or below, usually in the range of from about 5 to about 9. Preferably, the conversion is carried out at a pH of about 8 or below, usually in the range of from about 5 to about 8, and more preferably in the range of from about 6 to about 8. This conversion may also be carried out at a pH of about 7.8 or below, or 7.5 or below. Alternatively, the conversion may be carried out a neutral pH, i.e., about 7.

During the course of conversion, the pH of the reaction mixture may change. The pH of the reaction mixture may be maintained at a desired pH or within a desired pH range by the addition of an acid or a base during the course of conversion. Alternatively, the pH change may be controlled by using an aqueous solvent that comprises a buffer. Suitable buffers to maintain desired pH ranges are known in the art and include, for example, phosphate buffer, triethanolamine buffer, and the like. Combinations of buffering and acid or base addition may also be used.

As described above, when conversion to 4-cyano-3-hydroxybutyric acid derivative is desired, the cyanide may be provided in the form of a cyanide salt, typically an alkali salt (for example, NaCN, KCN, and the like), in the form of hydrocyanic acid (gaseous or in solution), or mixtures thereof. Hydrocyanic acid is a weak acid. In aqueous solutions within several pH units of its pKa (pKa =9.1 in water) cyanide is present as both $CN^-$ and HCN in equilibrium concentrations. At pH values below about 9, cyanide is predominantly present as HCN.

When the cyanide is provided by a cyanide salt, the reaction mixture is typically buffered or acidified or both to provide the desired pH. Suitable acids for acidification of basic cyanide salts solutions include organic acids, for example carboxylic acids, sulfonic acids, phosphonic acids, and the like, mineral acids, for example hydrohalic acids (such as hydrochloric acid), sulfuric acid, phosphoric acid, and the like, acidic salts, for example dihydrogenphosphate salts (e.g. $KH_2PO_4$), bisulfate salts (e.g. $NaHSO_4$) and the like, as well as hydrocyanic acid. The acids or acid salts used to acidify the cyanide salt may be selected to also provide a buffer in the resulting solution. For example, acidification with phosphoric acid or a dihydrogenphosphate salt may be used to provide a phosphate buffered solution of HCN in the phosphate buffer range (about pH 6–8).

When the cyanide is provided by hydrocyanic acid and a higher pH than that so created is desired, the reaction mixture is typically buffered or made less acidic by adding a base to provide the desired pH. Suitable bases for neutralization of hydrocyanic acid are organic bases, for example amines, alkoxides and the like, and inorganic bases, for example, hydroxide salts (e.g. NaOH), carbonate salts (e.g. NaHCO$_3$), bicarbonate salts (e.g. K$_2$CO$_3$), basic phosphate salts (e.g. K$_2$HPO$_4$, Na$_3$PO$_4$), and the like, as well as cyanide salts.

For pH values below about 9, at which cyanide is predominantly present as HCN, equation (1) describes the halohydrin dehalogenase catalyzed reaction of a 4-halo-3-hydroxybutyric acid ester with the HCN in unbuffered aqueous reaction mixtures.

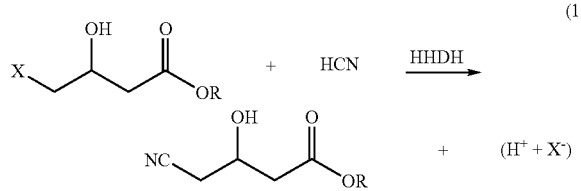
(1)

The consumption of the hydrocyanic acid, a weak acid (pKa~9) and release of the hydrohalic acid, a strong acid (pKa<0), causes the pH of the reaction mixture to drop if the aqueous hydrohalic acid (H$^+$+X$^-$) is not otherwise neutralized. The pH of the reaction mixture may be maintained at the desired level by standard buffering techniques, wherein the buffer neutralizes the hydrohalic acid up to the buffering capacity provided, or by the addition of a base concurrent with the course of the conversion. Such addition may be done manually while monitoring the reaction mixture pH or, more conveniently, by using an automatic titrator as a pH stat. A combination of partial buffering capacity and base addition can also be used for process control.

When the pH is maintained by buffering or by addition of a base over the course of the conversion, an aqueous halide salt rather than aqueous hydrohalic acid is the product of the overall process. For example, equation (2) represents the overall process when aqueous sodium hydroxide (Na$^+$+OH$^-$) is added over the course of the reaction to maintain an initial pH below about 9.

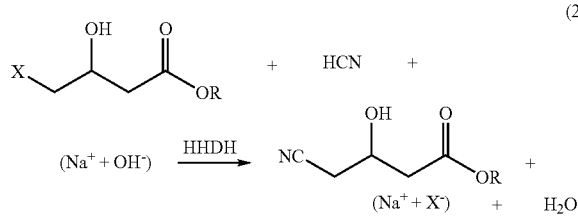
(2)

In the embodiment wherein a cyanide salt is added as the base to neutralize the hydrohalic acid as it is produced, the neutralization regenerates HCN and maintains the total cyanide concentration (HCN+CN$^-$) as well as the pH in the reaction mixture. This can be advantageous if the rate of conversion otherwise decreases as cyanide concentration decreases. For example, equation (3) represents the overall process when aqueous sodium cyanide (Na$^+$+CN$^-$) is added over the course of the reaction to maintain an initial pH. While the cyanide is present predominantly as HCN in the reaction mixture, the HCN concentration is maintained while the conversion in net consumes the added basic cyanide salt.

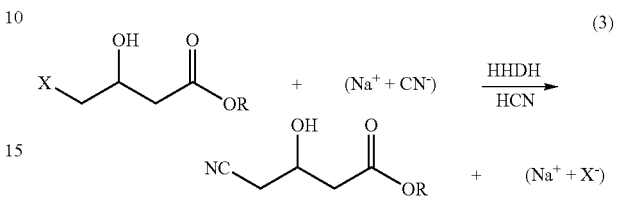
(3)

When base addition is employed to neutralize the hydrohalic acid released during the halohydrin dehalogenase-catalyzed reaction of a 4-halo-3-hydroxybutyrate ester or amide to a 4-cyano-3-hydroxybutyric acid ester or amide, the progress of the conversion may be monitored by the amount of base added to maintain the pH. Typically bases added to unbuffered or partially buffered reaction mixtures over the course of conversion are added in aqueous solutions.

When the nucleophile is the conjugate anion of a stronger acid, having a pKa significantly below the initial pH of the reaction solution, the nucleophile is present predominantly in its anionic form so that, unlike with HCN, a proton is not released on its reaction. Accordingly, the reaction mixture pH in reactions of such nucleophiles may be maintained without stoichiometric buffering or base addition. For example, the conjugate acid of azide, hydrazoic acid has a pKa of 4.7 and the conjugate acid of nitrite, nitrous acid, has a pKa of 3.3. Accordingly, at neutral pH, these nucleophiles are present predominantly in their anionic form, N$_3^-$ and ONO$^-$, respectively. That is, the neutral reaction mixture comprises aqueous azide and nitrite salt, respectively. Their reaction in such mixtures releases halide anion to form aqueous halide salt, not aqueous hydrohalic acid.

Those having ordinary skill in the art can readily determine the quantities of HHDH, 4-halo-3-hydroxybutyric acid ester or amide substrate and nucleophile to use based on, for example, the activity of HHDH as determined by the method in Example 4, the quantity of product desired, and the like. To illustrate, the amount of 4-halo-3-hydroxybutyric acid ester or amide can be in the range of from about 10 to about 500 g/L using about 10 mg to about 30 g of halohydrin dehalogenase. The stoichiometric amount of nucleophile can be readily determined. Further illustrative examples are provided herein.

Suitable conditions for carrying out the HHDH-catalyzed conversion of the present invention include a wide variety of conditions which can be readily optimized by routine experimentation that includes contacting the HHDH, 4-halo-3-hydroxybutyric acid ester or amide substrate, and nucleophile at an experimental pH and temperature and detecting product, for example, using the methods described in the Examples provided herein. The HHDH-catalyzed conversion of 4-halo-3-hydroxybutyric acid ester or amide to 4-nucleophile substituted-3-hydroxybutyric acid ester or amide is typically carried out at a temperature in the range of from about 15° C. to about 75° C. More typically, the reaction is carried out at a temperature in the range of from about 20° C. to about 55° C., and typically from about 20° C. to about 45° C. The reaction may also be carried out under ambient conditions.

The HHDH-catalyzed conversion of 4-halo-3-hydroxybutyric acid ester or amide to 4-nucleophile substituted-3-hydroxybutyric acid ester or amide is generally allowed to proceed until essentially complete or near complete conversion of substrate. Conversion of substrate to product can be monitored using known methods by detecting substrate and/or product. Suitable methods include gas chromatography, HPLC, and the like. Yields of the 4-nucleophile substituted-3-hydroxybutyric acid ester or amide generated in the reaction mixture are generally greater than about 50%, may also be greater than about 60%, may also be greater than about 70%, may be also be greater than about 80%, and are often greater than about 90%.

The 4-nucleophile substituted-3-hydroxybutyric acid ester or amide may be collected from the reaction mixture and optionally purified using methods that are known to those having ordinary skill in the art, as well as those described in the Examples.

Preferred 4-halo-3-hydroxybutyric acid ester or amide substrates of the present invention are chiral, being stereogenic at the 3-position, and may be racemic or non-racemic. Certain halohydrin dehalogenase enzymes used in the process of the present invention convert the chiral substrate to the 4-cyano-3-hydroxybutyric acid ester or amide with retention of the absolute stereochemistry at the stereogenic 3-position. Non-racemic chiral 4-halo-3-hydroxybutyric acid ester or amide substrates may be converted to substantially equally non-racemic 4-cyano-3-hydroxybutyric acid ester or amide products with little or no loss in stereopurity. The Examples show embodiments of the invention providing high retention of enantiopurity. (Due to conventions for designating stereochemistry, the enantiomer of ethyl 4-chloro-3-hydroxybutyrate designated as (S) and the enantiomer ethyl 4-cyano-3-hydroxybutyrate designated as (R) have the identical stereoconfiguration at the 3-position.)

In other embodiments of the present invention, certain halohydrin dehalogenase enzymes may be stereospecific for one stereoisomer of the chiral 4-halo-3-hydroxybutyric acid ester or amide substrate. The process of the present invention using such stereospecific enzymes may be used to react one stereoisomer of a stereoisomeric mixture of a 4-halo-3-hydroxybutyric acid ester or amide, for example a racemic mixture, while leaving the other stereoisomer substantially unreacted, thereby providing a kinetic resolution of the mixture.

A further significant characteristic of the present invention is that the purity of the 4-nucleophile substituted-3-hydroxybutyric acid ester or amide products generated is very high without the need for extensive purification procedures such as vacuum distillation. Typically, the purity of 4-nucleophile substituted-3-hydroxybutyric acid ester or amide products generated in accordance with the methods of the present invention are at least about 80%, usually at least about 90%, and typically at least about 95%. Product purity may be determined by conventional methods such as HPLC or gas chromatography.

II. Ketoreductase-Catalyzed Production of Halohydrins

The present invention further provides an enzymatic method for generating a 4-halo-3-hydroxybutyric acid ester or amide by:

(a) providing a 4-halo-3-ketobutyric acid ester or amide, wherein the halo substituent is selected from the group consisting of chlorine, bromine, and iodine; and (b) contacting the 4-halo-3-ketobutyric acid ester or amide with a ketoreductase, a cofactor, and a cofactor regeneration system under conditions suitable to form a reaction mixture for converting the 4-halo-3-ketobutyric acid ester or amide to the 4-halo-3-hydroxybutyric acid ester or amide.

The terms "ketoreductase" and "KRED" are used interchangeably herein to refer to an enzyme that, in the process of the present invention, catalyzes the reduction of a 4-halo-3-ketobutyric acid ester or amide to the corresponding 4-halo-3-hydroxybutyric acid ester or amide. Such catalytic activity may be detected in an assay such as that described in Example 4, hereinbelow.

As used herein, the term "cofactor" refers to a non-protein compound that operates in combination with an enzyme which catalyzes the reaction of interest. Suitable cofactors employed in the practice of the present invention include NADP$^+$ (nicotinamide-adenine dinucleotide phosphate), NADPH (i.e., the reduced form of nicotinamide adenine dinucleotide phosphate), NAD$^+$ (i.e., nicotinamide adenine dinucleotide), and NADH (i.e., the reduced form of NAD$^+$), and the like. The reduced form of the cofactor is regenerated by reducing the oxidized cofactor with a cofactor regeneration system.

In the present process, the ketoreductase catalyzes the reduction of the 4-halo-3-ketobutyric acid ester or amide by the reduced form of the cofactor. Equation (4) describes the ketoreductase-catalyzed reduction of a 4-halo-3-ketobutyric acid ester by NADH or NADPH, which are represented as alternatives by the designation NAD(P)H.

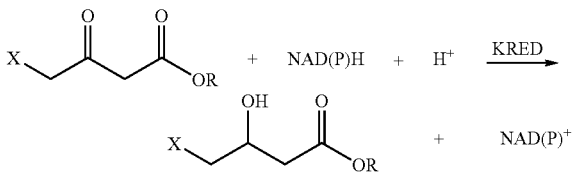

(4)

Ketoreductases that are suitable for carrying out the reduction of 4-halo-3-ketobutyric acid ester or amide to 4-halo-3-hydroxybutyric acid ester or amide include both naturally occurring ketoreductases, as well as non-naturally occurring ketoreductases generated by human manipulation Exemplary naturally occurring and non-naturally occurring ketoreductases and ketoreductase-encoding polynucleotides include those described herein.

Naturally occurring KRED enzymes can be found in a wide range of bacteria and yeasts. Several naturally occurring KRED gene and enzyme sequences have been reported in the literature, such as, *Candida magnoliae* (Genbank Acc. No. JC7338; GI:11360538), *Candida parapsilosis* (Genbank Ac. No. BAA24528.1; GI:2815409), *Sporobolomyces salmicolor* (Genbank Acc. No. AF160799; GI 6539734). Polynucleotide sequences encoding the ketoreductase from *Candida magnoliae* are provided as SEQ ID NOS: 1 (CR2-5), 3 (CR1-2), 5 (CR1-3), and 7 (CR2-4). SEQ ID NOS: 1 (CR2-5), 5 (CR1-3), and 7 (CR2-4) are variants that encode the *C. magnoliae* protein (SEQ ID NOS: 2, 6, and 8). SEQ ID NO: 3 (CR1-2) encodes a variant that differs from the *C. magnoliae* protein by one amino acid change (SEQ ID NO: 4). Enzymatic reduction of β-keto esters has been reported for a carbonyl reductase from *Rhodococcus erythropolis* (Peters, *Appl. Microbiol. Biotechnol.* (1992) 38:334–340;

Zelinski, *J. Biotechnol.* (1994) 33:283–292), an aldehyde reductase from *Sporoboromyces salmonicolor* AKU 4429 (Shimizu, *Biotechnol. Lett.* (1990) 12:593–596; *Appl. Environ. Microbiol.* (1990) 56:2374–2377). Enzymes such as those derived from *S. cerevisiae* (*J. Org. Chem.* (1991) 56:4778; *Biosci. Biotech. Biochem.* (1994) 58:2236), *Sporobolomyces salmonicolor* (*Biochim. Biophys. Acta* (1992) 1122:57), *Sporobolomyces* sp. (*Biosci. Biotech. Biochem.* (1993) 57:303; Japanese patent publication JP2566960), *Candida albicans* (*Biosci. Biotech. Biochem.* (1993) 57:303), *Candida macedoniensis* (*Arch. Biochem. Biophys.* (1992) 294–469), *Geotrichium candidum* (*Enzyme Microbiol. Technol.* (1992) 14:731) have been used for the reduction of ethyl 4-chloro-3-acetoacetate (ECAA). U.S. Pat. No. 6,168,935 describes the use of glycerol dehydrogenase (*Tetrahedron Lett.* (1988) 29:2453), alcohol dehydrogenase (ADH) from *Thermoanaerobium brockii* (JACS (1985) 107:4028), or *Sulfolobus solfataricus* (*Biotechnol. Lett.* (1991) 13:31) or *Pseudomonas* sp. (U.S. Pat. No. 5,385,833; *J. Org. Chem.* (1992) 57:1526).

Suitable non-naturally occurring ketoreductases can be readily identified by applying known methods, including mutagenesis, directed evolution, and the like, followed by screening for activity using the method described in Example 4. For example, these methods can be readily applied to naturally occurring ketoreductases, including the ones described herein. Exemplary non-naturally occurring ketoreductases are provided herein as SEQ ID NOS: 40 (KRED krh133c), 42 (KRED krh215), 44 (KRED krh267), 46 (KRED krh287), 48 (KRED krh320), 50 (KRED krh326), 52 (KRED krh408), 54 (KRED krh417), 56 (KRED krh483), 58 (KRED krh476), and 60 (KRED krh495). The polynucleotide sequences that encode them are provided herein as SEQ ID NOS: 39, 41, 43, 45, 47, 49, 51, 53, 55, 57, and 59, respectively. Additional non-naturally occurring ketoreductases that are suitable for use in the practice of the present invention are provided in the patent application entitled, "Improved Ketoreductase Polypeptides and Related Polynucleotides," filed on Aug. 11, 2003, and assigned U.S. application Ser. No. 60/494,300, which is incorporated herein by reference in its entirety.

Ketoreductases employed in the practice of the present invention typically exhibit an activity of at least about 1 μmol/min/mg in the assay described in Example 4, using the 4-halo-3-ketobutyric acid ester or amide substrate of interest. Ketoreductases employed in the practice of the present invention may exhibit an activity of at least 1 μmol/min/mg to about 10 μmol/min/mg and sometimes at least about $10^2$ μmol/min/mg, up to about $10^3$ μmol/min/mg or higher.

4-halo-3-ketobutyric acid esters and amides employed in the practice of the present invention can be readily purchased or synthesized using known methods. Exemplary 4-halo-3-ketobutyric acid ester substrates include those having the structure IV:

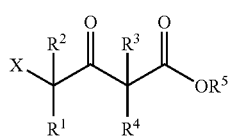

IV where:

X is a halogen selected from the group consisting of chlorine, bromine, and iodine; and $R^1$, $R^2$, $R^3$, $R^4$, and $R^5$ are selected as described for structure 1A.

Specific 4-halo-3-ketobutyric acid esters that may be employed in the practice of the present invention include ethyl 4-chloro-3-ketobutyric acid ester (i.e., where X is chlorine, $R^1$, $R^2$, $R^3$, and $R^4$ are each hydrogen, and $R^5$ is ethyl), methyl 4-chloro-3-ketobutyric acid ester (i.e., where X is chlorine, $R^1$, $R^2$, $R^3$, and $R^4$ are each hydrogen, and $R^5$ is methyl), ethyl 4-bromo-3-ketobutyric acid ester (i.e., where X is bromine, $R^1$, $R^2$, $R^3$, and $R^4$ are each hydrogen, and $R^5$ ethyl), ethyl 4-iodo-3-ketobutyric acid ester (i.e., where X is iodine, $R^1$, $R^2$, $R^3$, and $R^4$ are each hydrogen, and $R^5$ is ethyl), methyl 4-bromo-3-ketobutyric acid ester (i.e., where X is bromine, $R^1$, $R^2$, $R^3$, and $R^4$ are each hydrogen, and $R^5$ is methyl), methyl 4-iodo-3-ketobutyric acid ester (i.e., where X is iodine, $R^1$, $R^2$, $R^3$, and $R^4$ are each hydrogen, and $R^5$ is methyl), t-butyl-4-chloro-3-ketobutyric acid ester (i.e., where X is chlorine, $R^1$, $R^2$, $R^3$, and $R^4$ are each hydrogen, and $R^5$ t-butyl), t-butyl-4-bromo-3-ketobutyric acid ester (i.e., where X is bromine, $R^1$, $R^2$, $R^3$, and $R^4$ are each hydrogen, and $R^5$ is t-butyl), and t-butyl-4-iodo-3-ketobutyric acid ester (i.e., where X is iodine, $R^1$, $R^2$, $R^3$, and $R^4$ are each hydrogen, and $R^5$ is t-butyl). In certain embodiments, at least one of $R^1$, $R^2$, $R^3$, and $R^4$ is a lower alkyl, such as, for example, methyl, ethyl, or propyl.

When 4-halo-3-ketobutyric acid ester substrates having the structure of compound IV are reduced during the KRED-catalyzed conversion of the present invention, 4-halo-3-hydroxybutyric acid esters are generated having the structure V:

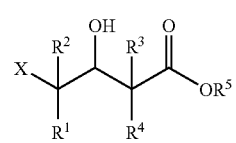

V where X, $R^1$, $R^2$, $R^3$, $R^5$ and $R^5$ are as described for structure IV.

4-halo-3-hydroxybutyric acid esters or amides produced by the ketoreductase-catalyzed reduction method of the present invention can then be readily used in the halohydrin dehalogenase-catalyzed conversions of the present invention. For example, 4-halo-3-hydroxybutyric acid esters corresponding to structure V can be used as substrate for conversion by HHDH in the presence of cyanide to generate 4-cyano-3-hydroxybutyric acid esters having the structure VI:

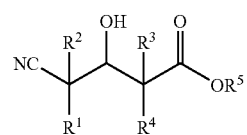

VI where $R^1$, $R^2$, $R^3$, $R^4$, and $R^5$ are as described as for compound V.

The term "cofactor regeneration system" refers herein to a set of reactants that participate in a reaction that reduces the oxidized form of the cofactor (e.g., NADP to NADPH). Cofactors oxidized by the ketoreductase-catalyzed reduction of the 4-halo-3-ketobutyric acid ester or amide are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst, that catalyzes the reduction of the oxidized form of the cofactor by the reductant. Cofactor regenerations systems to regenerate NADH or NADPH from NAD or NADP, respectively, are known in the art and may be used in the present invention.

Suitable cofactor regeneration systems employed in the practice of the present invention include glucose and glucose dehydrogenase, formate and formate dehydrogenase, glucose-6-phosphate and glucose-6-phosphate dehydrogenase, isopropylalcohol and secondary alcohol dehydrogenase, and the like, and may be used in combination with either NADP/NADPH or NAD/NADH as the cofactor.

The terms "glucose dehydrogenase" and "GDH" are used interchangeably herein to refer to an NAD or NADP-dependent enzyme that catalyzes the conversion of D-glucose and NAD or NADP to gluconic acid and NADH or NADPH, respectively. Equation (5) describes the glucose dehydrogenase-catalyzed reduction of NAD or NADP by glucose.

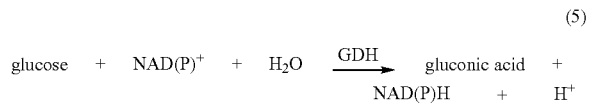

(5)

Glucose dehydrogenases that are suitable for use in the practice of the present invention include both naturally occurring glucose dehydrogenases, as well as non-naturally occurring glucose dehydrogenases. Naturally occurring glucose dehydrogenase encoding genes have been reported in the literature. For example, the *Bacillus subtilis* 61297 GDH gene was expressed in *E. coli* and was reported to exhibit the same physicochemical properties as the enzyme produced in its native host (Vasantha, et al., *Proc. Natl. Acad. Sci. USA* (1983) 80:785). The gene sequence of the *B. subtilis* GDH gene, which corresponds to Genbank Acc. No. M12276, was reported by Lampel, et al. (*J. Bacteriol.* (1986) 166:238–243) and in corrected form by Yamane, et al. (*Microbiology* (1996) 142:3047-3056) as Genbank Acc. No. D50453. Naturally occurring GDH genes also include those that encode the GDH from *B. cereus* ATCC 14579 (*Nature* (2003) 423:87–91; Genbank Acc. No. AE017013) and *B. megaterium* (*Eur. J. Biochem.* (1988) 174:485–490, Genbank Acc. No. X12370; *J. Ferment. Bioeng.* (1990) 70:363–369, Genbank Acc. No. GI216270). Glucose dehydrogenases from *Bacillus* sp. are provided herein as SEQ ID NOS: 10 and 12 (encoded by polynucleotide sequences corresponding to SEQ ID NOS: 9 and 11, respectively).

Non-naturally occurring glucose dehydrogenases may be generated using known methods, such as, for example, mutagenesis, directed evolution, and the like. GDH enzymes having suitable activity, whether naturally occurring or non-naturally occurring, may be readily identified using the assay described in Example 4. Exemplary non-naturally occurring halohydrin dehalogenases are provided herein as SEQ ID NOS: 62 (GDH 2313), 64 (GDH 2331), 66 (GDH 2279), and 68 (GDH 2379). The polynucleotide sequences that encode them are provided herein as SEQ ID NOS: 61, 63, 65, and 67, respectively. Additional non-naturally occurring glucose dehydrogenases that are suitable for use in the practice of the present invention are provided in the patent application entitled, "Improved Glucose Dehydrogenase Polypeptides and Related Polynucleotides," filed on Aug. 11, 2003, and assigned U.S. application Ser. No. 60/494,300, which is incorporated herein by reference in its entirety.

Glucose dehydrogenases employed in the practice of the present invention may exhibit an activity of at least about 10 µmol/min/mg and sometimes at least about $10^2$ µmol/min/mg or about $10^3$ µmol/min/mg, up to about $10^4$ µmol/min/mg or higher in the assay described in Example 4.

When glucose and glucose dehydrogenase are employed as the cofactor regeneration system, as the 4-halo-3-ketobutyric acid ester or amide is reduced by the ketoreductase and NADH or NADPH, the resulting NAD or NADP is reduced by the coupled oxidation of glucose to gluconic acid by the glucose dehydrogenase. The net reaction is described by equation (6), which is the summation of equations (4) and (5):

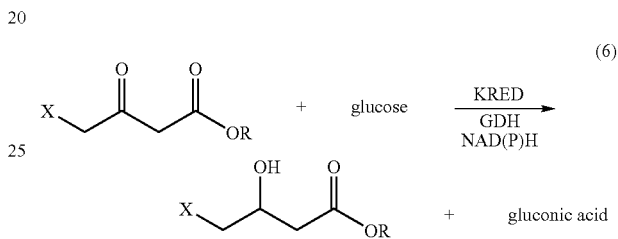

(6)

The ketoreductase-catalyzed reduction of 4-halo-3-ketobutyric acid ester or amide is generally carried out in a solvent. The solvent may be a co-solvent system, such as, for example, an aqueous co-solvent system. Suitable solvents (including co-solvent systems) for carrying out this conversion are the same as those described above for the HHDH-catalyzed conversion of 4-halo-3-hydroxybutyric acid esters and amides to 4-cyano-3-hydroxybutyric acid esters and amides.

The aqueous solvent (water or aqueous co-solvent system) may be pH-buffered or unbuffered. The conversion of the 4-halo-3-ketobutyric acid ester or amide to the 4-halo-3-hydroxybutyric acid ester or amide may be carried out at a pH of about 5 or above. Generally, the conversion is carried out at a pH of about 10 or below, usually in the range of from about 5 to about 10. Typically, the conversion is carried out at a pH of about 9 or below, usually in the range of from about 5 to about 9. Preferably, the conversion is carried out at a pH of about 8 or below, usually in the range of from about 5 to about 8, and more preferably in the range from about 6 to about 8. Alternatively, the conversion may be carried out a neutral pH, i.e., about 7.

When the glucose/glucose dehydrogenase cofactor regeneration system is employed, the co-production of gluconic acid (pKa=3.6), as represented in equation (6) causes the pH of the reaction mixture to drop if the resulting aqueous gluconic acid is not otherwise neutralized. The pH of the reaction mixture may be maintained at the desired level by standard buffering techniques, wherein the buffer neutralizes the gluconic acid up to the buffering capacity provided, or by the addition of a base concurrent with the course of the conversion. Suitable buffers and procedures for buffering and suitable bases and procedures for the addition of base during the course of the conversion are the same as those described above for the HHDH-catalyzed conversion of 4-halo-3-hydroxybutyrate esters and amides to 4-cyano-3-hydroxybuyrate esters and amides.

In the ketoreductase-catalyzed reduction of the 4-halo-3-ketobutyric acid ester or amide using glucose/glucose dehydrogenase for cofactor regeneration, when the pH is maintained by buffering or by addition of a base over the course of the conversion, an aqueous gluconate salt rather than aqueous gluconic acid is the product of the overall process. For example, equation (7) represents the overall process when aqueous sodium hydroxide (Na$^+$+OH$^-$) is added over the course of the reaction to maintain the pH:

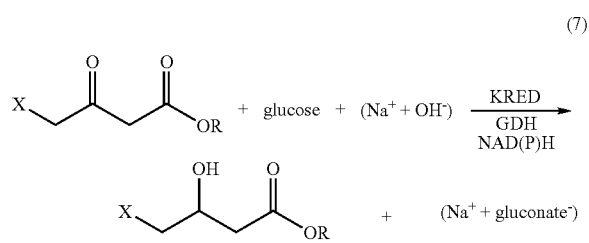

(7)

When base addition is employed to neutralize the gluconic acid released during the ketoreductase-catalyzed reduction of a 4-halo-3-ketobutyric acid ester or amide using the glucose/glucose dehydrogenase cofactor regeneration system, the progress of the conversion may be monitored by the amount of base added to maintain the pH. Typically bases added to unbuffered or partially buffered reaction mixtures over the course of conversion are added in aqueous solutions.

The terms "formate dehydrogenase" and "FDH" are used interchangeably herein to refer to an NAD or NADP-dependent enzyme that catalyzes the conversion of formate and NAD or NADP to carbon dioxide and NADH or NADPH, respectively. Formate dehydrogenases that are suitable for use in the practice of the present invention include both naturally occurring formate dehydrogenases, as well as non-naturally occurring formate dehydrogenases. Formate dehydrogenases include those corresponding to SEQ ID NOS: 70 (*Pseudomonas* sp.) and 72 (*Candida boidinii*), which are encoded by polynucleotide sequences corresponding to SEQ ID NOS: 69 and 71, respectively. Formate dehydrogenases employed in the practice of the present invention, whether naturally occurring or non-naturally occurring, may exhibit an activity of at least about 1 µmol/min/mg, sometimes at least about 10 µmol/min/mg, or at least about $10^2$ µmol/min/mg, up to about $10^3$ µmol/min/mg or higher, and can be readily screened for activity in the assay described in Example 4.

As used herein, the term "formate" refers to formate anion (HCO$_2^-$), formic acid (HCO$_2$H), and mixtures thereof. Formate may be provided in the form of a salt, typically an alkali or ammonium salt (for example, HCO$_2$Na, KHCO$_2$NH$_4$, and the like), in the form of formic acid, typically aqueous formic acid, or mixtures thereof. Formic acid is a moderate acid. In aqueous solutions within several pH units of its pKa (pKa=3.7 in water) formate is present as both HCO$_2^-$ and HCO$_2$H in equilibrium concentrations. At pH values above about 4, formate is predominantly present as HCO$_2^-$. When formate is provided as formic acid, the reaction mixture is typically buffered or made less acidic by adding a base to provide the desired pH, typically of about 5 or above. Suitable bases for neutralization of formic acid are as described for neutralization of hydrocyanic acid, above.

For pH values above about 5, at which formate is predominantly present as HCO$_2^-$, equation (8) describes the formate dehydrogenase-catalyzed reduction of NAD or NADP by formate.

(8)

When formate and formate dehydrogenase are employed as the cofactor regeneration system, as the 4-halo-3-ketobutyric acid ester or amide is reduced by the ketoreductase and NADH or NADPH, the resulting NAD or NADP is reduced by the coupled oxidation of formate to carbon dioxide by the formate dehydrogenase. The net reaction is described by equation (9), which is the summation of equations (4) and (8):

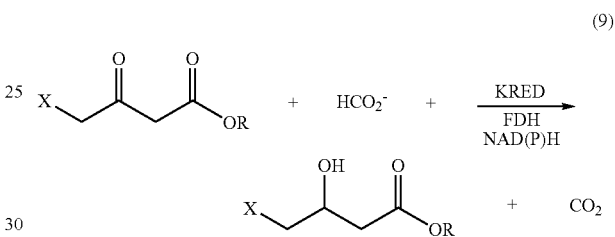

(9)

Equation (9) shows that when the formate/formate dehydrogenase cofactor regeneration system is employed for the reduction of the 4-halo-3-ketobutyric acid ester or amide in aqueous solution with pH above about 5, protons in solution are consumed and the reaction causes the pH of the reaction mixture to rise if it is not otherwise buffered or re-acidified. The pH of the reaction mixture may be maintained at the desired level by standard buffering techniques, wherein the buffer releases protons up to the buffering capacity provided, or by the addition of an acid concurrent with the course of the conversion. Suitable acids to add during the course of the reaction to maintain the pH include organic acids, for example carboxylic acids, sulfonic acids, phosphonic acids, and the like, mineral acids, for example hydrohalic acids (such as hydrochloric acid), sulfuric acid, phosphoric acid, and the like, acidic salts, for example dihydrogenphosphate salts (e.g. KH$_2$PO$_4$), bisulfate salts (e.g. NaHSO$_4$) and the like. Particularly preferred is formic acid, whereby both the formate concentration and the pH of the solution are maintained. For example, equation (10) represents the overall process when formic acid (HCO$_2$H) is added over the course of the reaction to maintain an initial pH above about 5. While the formate is present predominantly as HCO$_2^-$ in the reaction mixture, the HCO$_2^-$ concentration is maintained while the conversion in net consumes the added formic acid.

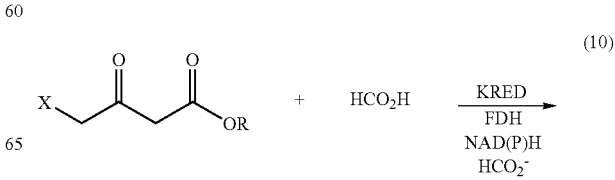

(10)

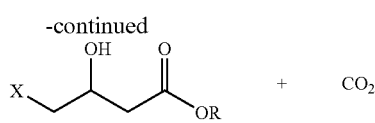

When acid addition is employed to maintain the pH during the ketoreductase-catalyzed reduction of a 4-halo-3-ketobutyric acid ester or amide using the formate/formate dehydrogenase cofactor regeneration system, the progress of the conversion may be monitored by the amount of acid added to maintain the pH. Typically acids added to unbuffered or partially buffered reaction mixtures over the course of conversion are added in aqueous solutions.

In carrying out the methods of the present invention, either the oxidized or reduced form of the cofactor may be provided initially. As described above, the cofactor regeneration system converts oxidized cofactor to its reduced form, which is then utilized in the reduction of the ketoreductase substrate (i.e., 4-halo-3-ketobutyric acid ester or amide) to the corresponding halohydrin.

As with the halohydrin dehalogenases, the ketoreductase and enzymes of the cofactor regeneration system may be provided to the reaction mixture for converting 4-halo-3-ketobutyric acid ester or amide in the form of purified enzyme, cell extract, cell lysate, or whole cells transformed with gene(s) encoding the ketoreductase and enzymes of the cofactor regeneration system. The genes encoding the enzymes can be transformed into host cells either separately, or together into the same host cell. For example, in one embodiment one set of host cells can be transformed with ketoreductase encoding gene(s) and another set can be transformed with cofactor regeneration system enzyme (e.g., GDH, FDH, and the like) encoding gene(s). Both sets of transformed cells can be utilized together in the reaction mixture in the form of whole cells or cell lysates or cell extract derived therefrom. Alternatively, a host cell can be transformed with genes encoding both ketoreductase and a cofactor regeneration system enzyme, such that each cell expresses both ketoreductase and the cofactor regeneration system enzyme. In a further embodiment, the host cell can be transformed with genes encoding ketoreductase, a cofactor regeneration system enzyme, and a halohydrin dehalogenase. These cells can be utilized in the methods of the present invention to provide the enzymes in the form of whole cells, cell lysate, or cell extract. As described for the reaction mixture of the HHDH-catalyzed method, the solid reactants (i.e., enzymes, salts, cofactor regeneration system, cofactor, and the like) may be provided in a variety of different forms, including powder (e.g., lyophilized, spray dried, and the like), solution, emulsion, suspension, and the like.

The quantities of reactants used in the reduction step will generally vary depending on the quantities of 4-halo-3-hydroxybutyric acid ester or amide desired, and concomitantly the amount of ketoreductase substrate employed. The following guidelines can be used to determine the amounts of ketoreductase, cofactor, and cofactor regeneration system to use. Generally, 4-halo-3-ketobutyric acid esters and amides are employed at a concentration of about 10 to 500 grams/liter using from about 10 mg to about 5 g of ketoreductase and about 25 mg to about 5 g of cofactor. Those having ordinary skill in the art will readily understand how to vary these quantities to tailor them to the desired level of productivity and scale of production. Appropriate quantities of cofactor regeneration system may be readily determined by routine experimentation based on the amount of cofactor and/or ketoreductase utilized. In general, the reductant (e.g. glucose, formate) is utilized at levels above the equimolar level of ketoreductase substrate to achieve essentially complete or near complete conversion of the ketoreductase substrate.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor regeneration system, cofactor, ketoreductase, and ketoreductase substrate may be added first to the solvent For improved mixing efficiency when an aqueous co-solvent system is used, the cofactor regeneration system, ketoreductase, and cofactor are usually added and mixed into the aqueous phase first. The organic phase may then be added and mixed in, followed by addition of the ketoreductase substrate. Alternatively, the ketoreductase substrate may be premixed in the organic phase, prior to addition to the aqueous phase.

As for the halohydrin dehalogenase-catalyzed conversion of 4-halo-3-hydroxybutyric acid esters and amides, suitable conditions for carrying out the ketoreductase-catalyzed reduction of 4-halo-3-ketobutyric acids esters and amides of the present invention include a wide variety of conditions that can be readily determined by those having ordinary skill in the art. Suitable temperatures for carrying out the ketoreductase-catalyzed reduction step are typically in the range of from about 15° C. to about 75° C. Usually, the reactions are carried out at a temperature in the range of from about 20° C. to about 55° C., and preferably from about 20° C. to about 45° C. The reaction may also be carried out under ambient conditions, As in the halohydrin dehalogenase-catalyzed reaction, the ketoreductase-catalyzed reaction is allowed to proceed until essentially complete or near complete conversion of substrate is observed using methods that are known in the art. As in the halohydrin dehalogenase-catalyzed reaction, the progression of the ketoreductase-catalyzed reaction may be monitored by monitoring the amount of base or acid added to counter the pH change that may otherwise occur with the particular cofactor regeneration system that is used, as described above.

The ketoreductase-catalyzed reduction of the 4-halo-3-ketobutyric acid ester or amide substrate generates a new stereogenic carbon at the 3-position of the 4-halo-3-hydroxybutyric acid ester or amide product. Typically, the 4-halo-3-hydroxybutyric acid ester or amide is generated with a relatively high stereoselectivity at the 3-position. Thus, the 4-halo-3-hydroxybutyric acid esters and amides generated by the ketoreductase-catalyzed reduction of 4-halo-3-ketobutyric acid esters and amides are typically chiral and non-racemic. The ketoreductase reactions used in present invention typically generate preferred nonracemic, chiral 4-halo-3-hydroxybutyric acid esters having an e.e. of at least about 90% e.e., usually at least about 95% e.e., and typically at least about 99% e.e. The Examples illustrate embodiments providing ethyl (S)-4-chloro-3-hydroxybutyrate with greater than 99% e.e.

As used herein, the term "enantiomeric excess" or "e.e." refers to the absolute difference between the mole or weight fractions of major ($F_{(+)}$) and minor ($F_{(-)}$) enantiomers (i.e., $|F_{(+)} - F_{(-)}|$), where $F_{(+)} + F_{(-)} = 1$. Percent e.e. is $100 \times |F_{(+)} - F_{(-)}|$. Enantiomeric composition can be readily characterized by using the gas chromatography method described in Example 6, hereinbelow, and using methods that are known in the art.

As described above, when these nonracemic chiral 4-halo-3-hydroxybutyric acid esters or amides are used as substrates in the halohydrin dehalogenase-catalyzed reactions of the present invention, the resulting 4-substituted-4-hydroxybutyric acid esters or amides are substantially equally nonracemic, with little or no loss in stereopurity. The combination of the high stereoselectivity of the ketoreductase-catalyzed production of the nonracemic 4-halo-3-hydroxybutyric acid esters or amides and the high stereofidelity of the halohydrin dehalogenase-catalyzed conversion of them to the corresponding nonracemic 4-cyano-3-hydroxybutyric acid esters or amides provides a particularly attractive inventive process for the overall production of nonracemic 4-cyano-3-hydroxybutyric acid esters or amides of high e.e. from 4-halo-3-ketobutyric acid esters or amides.

A further significant characteristic of the present invention is that the yield of chiral products generated is very high. Typically, the yields of 4-halo-3-hydroxybutyric acid ester or amide and 4-nucleophile substituted-3-hydroxybutyric acid ester or amide products generated in accordance with the methods of the present invention are at least about 70%, usually at least about 80%, typically at least about 90%, and may be at least about 95%. The computation of product yield is based on initial substrate quantity provided and the amount of product formed in the reaction mixture. Product 4-halo-3-hydroxybutyric acid ester or amide may be optionally purified prior to contacting with the halohydrin dehalogenase. As used herein, the term "purified" refers to a process in which a separation process is applied to mixture, resulting in an increase in concentration of one component relative to other components in the mixture. Suitable purification processes employed in the practice of the present invention include, for example, filtration, solid or liquid phase extraction, distillation, and the like.

If the 4-halo-3-hydroxybutyric acid ester or amide is purified from the ketoreductase reaction mixture, it is subsequently added to a solvent (e.g., a monophasic solvent, a biphasic aqueous co-solvent system) with the halohydrin dehalogenase and nucleophile.

III. Enzymatic Conversion of 4-Halo-3-Ketobutyric Acid Ester/Amide to 4-Nucleophile Substituted-3-Hydroxybutyric Acid Ester/Amide in a Single Reaction Vessel The present invention provides a method for carrying out the conversion of 4-halo-3-ketobutyric acid esters and amides to the corresponding 4-nucleophile substituted-3-hydroxybutyric acid esters and amides in a single reaction vessel, the method comprising contacting the 4-halo-3-ketobutyric acid ester or amide with a ketoreductase, a cofactor, a cofactor regeneration system, a nucleophile, and a halohydrin dehalogenase to form a reaction mixture for converting the 4-halo-3-ketobutyric acid ester or amide to a 4-nucleophile substituted-3-hydroxybutyric acid ester or amide Mechanistically, this single-vessel method proceeds via ketoreductase-catalyzed conversion of the 4-halo-3-ketobutyric acid ester or amide to provide the 4-halo-3-hydroxybutyric acid ester or amide in situ, and consequent halohydrin dehalogenase-catalyzed conversion of the 4-halo-3-hydroxybutyric acid ester or amide to the corresponding 4-nucleophile substituted-3-hydroxybutyric acid ester or amide. Significantly, the 4-halo-3-hydroxybutyric acid ester or amide produced by the ketoreductase-catalyzed reaction is not separated or recovered prior to its contact with halohydrin dehalogenase and nucleophile (e.g., cyanide and the like) for its conversion to 4-nucleophile substituted-3-hydroxybutyric acid ester or amide.

Suitable reactants (substrates, enzymes, cofactors), solvents, pH, temperature, and other reaction conditions and procedures for the single-vessel conversion of 4-halo-3-ketobutyric acid ester or amide to 4-nucleophile substituted-3-hydroxybutyric acid ester or amide are the same as those described above for the carrying out the halohydrin dehalogenase-catalyzed conversion of 4-halo-3-hydroxybutyric acid esters and amides to the corresponding 4-nucleophile substituted-3-hydroxybutyric acid esters and amides.

When glucose and glucose dehydrogenase are used as the cofactor regeneration system and two equivalents of base are added during the course of the reaction to neutralize both the gluconic acid and hydrohalic acid produced and maintain the initial pH of the reaction mixture (for initial pHs in the range of about 5 to about 9), the overall process in a single-vessel reaction is described by equation (10), which is the summation of equations (2) and (7), wherein aqueous sodium hydroxide is illustrated as the base.

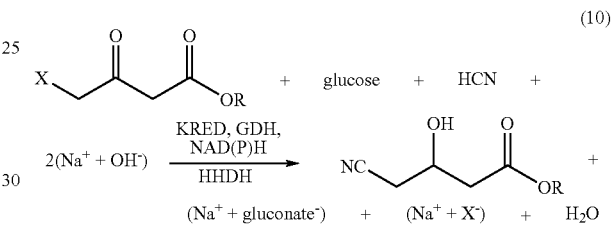

(10)

Other single-vessel overall process equations can result from summing equations describing other options for conducting the halohydrin dehalogenase-catalyzed reaction (e.g. using a cyanide salt as the base) and/or the ketoreductase reaction (e.g. using formate and formate dehydrogenase as the cofactor regeneration system), as described above for the separately conducted reactions.

It will also be understood that the same single-vessel result may be obtained by first conducting the ketoreductase reaction separately as described above, then subsequently adding halohydrin dehalogenase and cyanide into the ketoreductase reaction mixture and conducting the halohydrin dehalogenase reaction in the presence of the ketoreductase reaction components.

An embodiment of a single-vessel process for converting a 4-halo-3-ketobutyric acid ester to a 4-cyano-3-hydroxybutyric acid ester is illustrated in Example 24.

IV. Compositions

The present invention further provides compositions that are useful for the enzymatic conversion of 4-halo-3-hydroxybutyric acid ester or amide to 4-nucleophile substituted-3-hydroxybutyric acid ester or amide. These compositions comprise a halohydrin dehalogenase, a 4-halo-3-hydroxybutyric acid ester or amide, and a nucleophile. In a preferred composition, the nucleophile is cyanide.

In a further embodiment, the present invention provides compositions useful for preparing 4-nucleophile substituted-3-hydroxybutyric acid esters and amides that have a ketoreductase, a cofactor regeneration system, a cofactor, and a halohydrin dehalogenase. These compositions may further include a 4-halo-3-ketobutyric acid ester or amide.

Any of the previously described ketoreductases, components of a cofactor regeneration system, cofactors, halohydrin dehalogenases, 4-halo-3-ketobutyric acid esters or amides, 4-halo-3-hydroxybutyric acid esters or amides, and nucleophiles may be employed in these compositions.

Compositions of the present invention may be in solid (e.g., a powder) or liquid (e.g., solution, emulsion, suspension, and the like) form. For example, the composition may be in the form of a lyophilized or spray dried powder. Alternatively, the composition may further comprise a solvent.

The compositions may further include components for pH control or processability, including, for example, a salt, an acid, a base, a buffer, a solubilizing agent, etc.

V. Halohydrin Dehalogenases, Ketoreductases, and Cofactor Regeneration System Enzymes and Corresponding Polynucleotides In addition to the specific enzymes and polynucleotides described herein, those having ordinary skill in the art will recognize that known techniques can be readily applied in the discovery of both naturally occurring and non-naturally occurring polynucleotides encoding enzymes suitable for use in the practice of the present invention. See, e.g., Ling, et al., "Approaches to DNA mutagenesis: an overview," *Anal. Biochem.*, 254(2):157–78 (1997); Dale, et al., "Oligonucleotide-directed random mutagenesis using the phosphorothioate method," *Methods Mol. Biol.*, 57:369–74 (1996); Smith, "In vitro mutagenesis," *Ann. Rev. Genet.*, 19:423–462 (1985); Botstein, et al., "Strategies and applications of in vitro mutagenesis," *Science*, 229:1193–1201 (1985); Carter, "Site-directed mutagenesis," *Biochem. J.*, 237:1–7 (1986); Kramer, et al., "Point Mismatch Repair," *Cell*, 38:879–887 (1984); Wells, et al., "Cassette mutagenesis: an efficient method for generation of multiple mutations at defined sites," *Gene*, 34:315–323 (1985); Minshull, et al., "Protein evolution by molecular breeding," *Current Opinion in Chemical Biology*, 3:284–290 (1999); Christians, et al., "Directed evolution of thymidine kinase for AZT phosphorylation using DNA family shuffling," *Nature Biotechnology*, 17:259–264 (1999); Crameri, et al., "DNA shuffling of a family of genes from diverse species accelerates directed evolution," *Nature*, 391:288–291; Crameri, et al., "Molecular evolution of an arsenate detoxification pathway by DNA shuffling," *Nature Biotechnology*, 15:436–438 (1997); Zhang, et al., "Directed evolution of an effective fucosidase from a galactosidase by DNA shuffling and screening," *Proceedings of the National Academy of Sciences, U.S.A.*, 94:45-4–4509; Crameri, et al., "Improved green fluorescent protein by molecular evolution using DNA shuffling," *Nature Biotechnology*, 14:315–319 (1996); Stemmer, "Rapid evolution of a protein in vitro by DNA shuffling," *Nature*, 370:389–391 (1994); Stemmer, "DNA shuffling by random fragmentation and reassembly: In vitro recombination for molecular evolution," *Proceedings of the National Academy of Sciences, U.S.A.*, 91:10747–10751 (1994); WO 95/22625; WO 97/0078; WO 97/35966; WO 98/27230; WO 00/42651; and WO 01/75767. These and other known methods can be readily applied, for example, together with the assays described herein, to identify other ketoreductases, halohydrin dehalogenases, and cofactor regeneration system enzymes having the activities described herein, as well as other desirable properties, e.g., altered temperature and/or pH optimums, solvent resistance, and the like. For example, a ketoreductase may be mutated or evolved to generate libraries that can be screened to identify a ketoreductase having a preference for one cofactor type over another, for example, NAD versus NADP, or vice-versa.

Polynucleic acid sequences encoding the enzymes employed in the present invention may be codon optimized for optimal production from the host organism selected for expression. Those having ordinary skill in the art will recognize that tables and other references providing codon preference information for a wide range of organisms are readily available. See e.g., Henaut and Danchin, "*Escherichia coli* and *Salmonella,* " Neidhardt, et al. eds., ASM Press, Washington, D.C. (1996) pp. 2047–2066.

Enzymes employed in the practice of the present invention may be produced by transforming a vector containing a polynucleotide encoding halohydrin dehalogenase, ketoreductase, or a cofactor regeneration system enzyme into a host cell using well known molecular biology techniques. See, e.g., Berger and Kimmel, "Guide to Molecular Cloning Techniques", *Methods in Enzymology*, Volume 152, Academic Press, Inc., San Diego, Calif.; Sambrook, et al., "Molecular Cloning—A Laboratory Manual," $2^{nd}$ Ed., Vol. 1–3, Cold Spring Harbor Laboratory, Cold Spring Harbor, New York, 1989; and "Current Protocols in Molecular Biology," F. M. Ausubel, et al., eds., *Current Protocols*, a joint venture between Greene Publishing Associates, Inc. and John Wiley & Sons, Inc. (supplemented through 1999). Methods for making the enzymes are illustrated in Examples 1 and 2.

The foregoing and other aspects of the invention may be better understood in connection with the following non-limiting examples.

EXAMPLE 1

Construction of Expression Constructs for Expression of Halohydrin Dehalogenase, Ketoreductase, and Glucose Dehydrogenase (1) Halohydrin Dehalogenase (HHDH)

Figure 2:
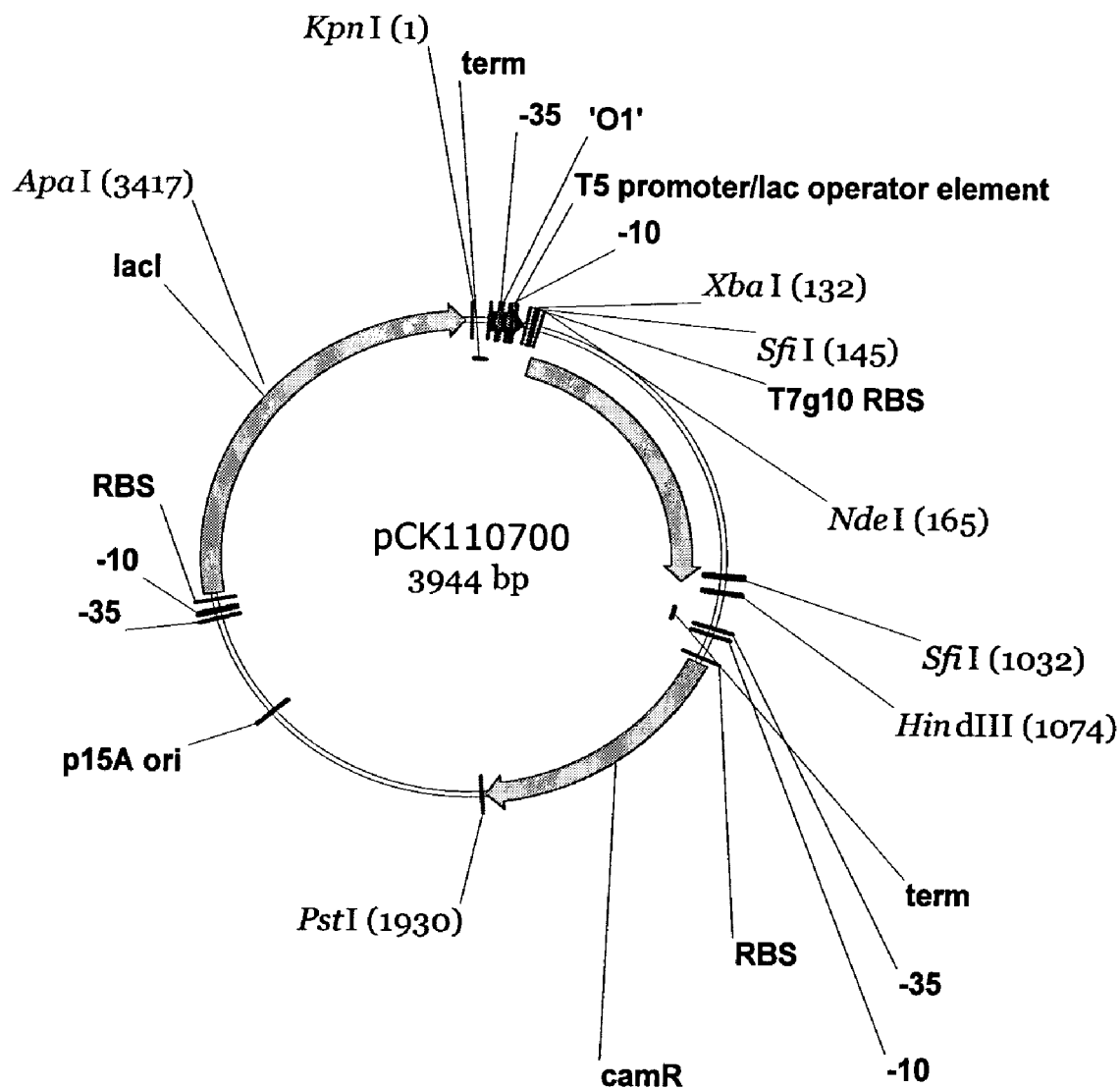
FIG. 2 depicts a 3944 bp expression vector (pCK110700) of the present invention comprising a p15A origin of replication (p15 ori), a lacI repressor, a T5 promoter, a T7 ribosomal binding site (T7g10), and a chloramphenicol resistance gene (camR).

The gene for the halohydrin dehalogenase was codon optimized for expression in *E. coli* based on the amino acid sequence of the halohydrin dehalogenase from *Agrobacterium* sp. The gene was synthesized using 60-mer oligomers, and cloned into expression vector pCK110700 (depicted in FIG. 2) under the control of a T5 promoter. The vectors were transformed into *E. coli* TOP10 (Invitrogene, Carlsbad, Calif.) from which plasmid DNA was prepared using standard methods. The plasmid DNA was then transformed into *E. coli* BL21 (Stratagene, La Jolla, Calif.), the expression host, using standard methods. Several clones were found in the expression library that expressed active HHDH. The genes from these clones were sequenced (see SEQ ID Nos: 13 (HHDH.1), 15 (HHDH.2), and 17 (HHDH.16) which encode polypeptide sequences SEQ ID Nos. 14, 16, and 18, respectively).

(2) Ketoreductase (KRED)

Figure 3:
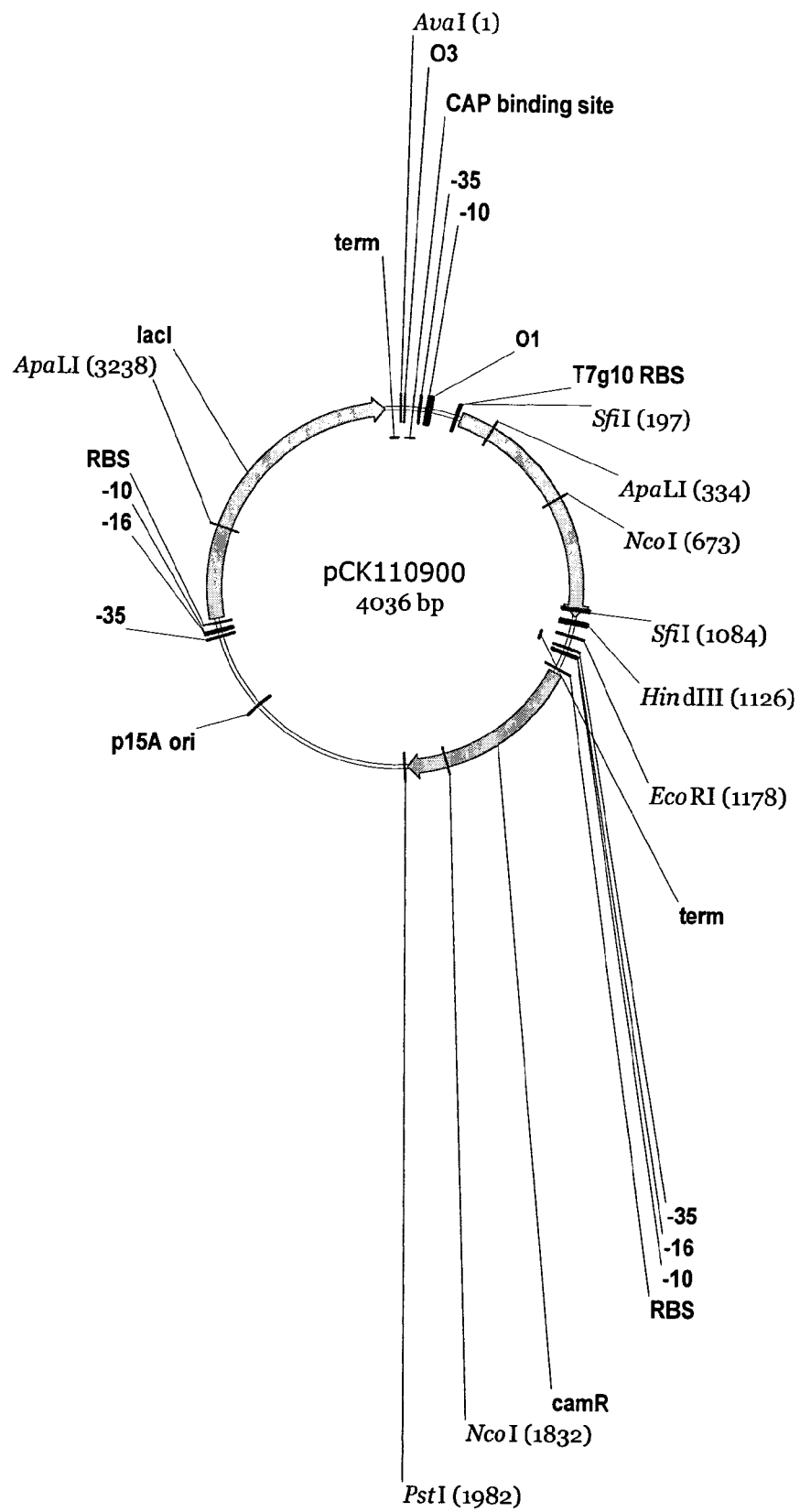
FIG. 3 depicts a 4036 bp expression vector (pCK110900) of the present invention comprising a p15A origin of replication (p15 ori), a lacI repressor, a CAP binding site, a lac promoter (lac), a T7 ribosomal binding site (T7g10 RBS), and a chloramphenicol resistance gene (camR).

The gene for the ketoreductase was codon optimized for expression in *E. coli* based on the amino acid sequence of the ketoreductase from *Candida magnoliae*. The gene was synthesized using 60-mer oligomers, and cloned into the SfiI cloning sites of expression vector, pCK110900 (depicted in FIG. 3), under the control of a lac promoter and lacI repressor gene. The expression vector contains the p15A origin of replication and the chloroamphenicol resistance gene. The plasmids were transformed into an *E. coli* expression host using standard methods. Several clones were found that expressed active ketoreductase and their genes were sequenced to confirm the DNA sequences (see SEQ ID Nos: 1 (Ketoreductase 1), 3 (Ketoreductase 2), 5 (Ketoreductase 3), and 7 (Ketoreductase 4), which encode for polypeptide sequences SEQ ID Nos. 2, 4, 6, and 8, respectively).

(3) Glucose Dehydrogenase (GDH)

The genes for the glucose dehydrogenase were amplified using the polymerase chain reaction (PCR) from genomic DNA preparations of Bacillus subtilis and Bacillus megaterium. The primers for the amplification reactions were designed using the published B. subtilis and B. megaterium glucose dehydrogenase gene sequences, and were as follows:

```
B. subtilis forward primer (SEQ ID NO: 19):
5'-GAATTCGCCCATATGTATCCGGATTTAAAAGG-3'

B. subtilis reverse primer (SEQ ID NO: 20):
5'-TGGCCGGATCCTCATTAACCGCGGCCTGCCTGGA-3'

B. megaterium forward primer (SEQ ID NO: 21):
5'-GAATTCGCCCATATGTATAAAGATTTAGAAGG-3'

B. megaterium reverse primer (SEQ ID NO 22):
5'-GGCCGGATCCTCATTATCCGCGTCCTGCTTGGA-3'
```

The PCR products were cloned into the SfiI cloning sites of expression vector, pCK110900 (depicted in FIG. 3), under the control of a lac promoter and lacI repressor gene. The expression vector contains the p15A origin of replication and the chloroamphenicol resistance gene. The plasmids were transformed into an E. coli expression host using standard methods. Several clones were found to express active GDH and the genes were sequenced to confirm the sequences (see SEQ ID Nos: 9 (Glucose dehydrogenase S06-3) and 11 (Glucose dehydrogenase M02-6), which encode for polypeptide sequences SEQ ID Nos. 10 and 12, respectively).

(4) Formate Dehydrogenase (FDH)

The genes for the formate dehydrogenase were codon optimized for expression in E. coli based on the amino acid sequences of the formate dehydrogenase from Pseudomonas species strain 101 (Protein Database Accession ID 2NAD_A) and Candida boidinii (Genbank Accession No. CAA09466). The genes were synthesized using 60-mer oligomers, and cloned into the SfiI cloning sites of expression vector, pCK110900 (depicted in FIG. 3), under the control of a lac promoter and lacI repressor gene. The expression vector contains the p15A origin of replication and the chloroamphenicol resistance gene. The plasmids were transformed into an E. coli expression host using standard methods. Clones were found that expressed active formate dehydrogenase and the genes were sequenced to confirm the DNA sequences (see SEQ ID NOS: 69 and 71, which encode for polypeptide sequences SEQ ID Nos. 70 and 72, respectively.)

EXAMPLE 2

Production of Enzyme (1) HHDH Enzyme:

In an aerated agitated fermentor, 10.0L of growth medium containing 0.528 g/L ammonium sulphate; 7.5 g/L of dipotassium hydrogen phosphate trihydrate; 3.7 g/L of potassium dihydrogen phosphate; 2 g/L of Tastone-154 yeast extract; 0.05 g/L ferrous sulphate; and 3 ml/L of a trace element solution containing 2 g/L of calcium chloride dihydrate, 2.2 g/L of zinc sulfate septahydrate, 0.5 g/L manganese sulfate monohydrate, 1 g/L cuprous sulfate heptahydrate: 0.1 g/l sodium borate decahydrate and 0.5 g/L EDTA, was brought to a temperature of 30° C. The fermentor was inoculated with a late exponential culture of Escherchia coli BL21 (Stratagene, La Jolla, Calif.) equipped with plasmid containing HHDH polynucleotides as described in Example 1, then grown in a shake flask containing LB, 1% glucose (Sigma Chemical Co., St. Louis, Mo.), and 30 µg/ml chloroamphenicol (Sigma Chemical Co., St. Louis, Mo.) to a starting optical density at 600 nm ($OD_{600}$) of 0.5 to 2.0. The fermenter was agitated at 500–1500 rpm and air was supplied to the fermentation vessel at 1.0–15.0 L/min to maintain a dissolved oxygen level of 30% saturation or greater. The pH of the culture was controlled at 7.0 by addition of 20% v/v ammonium hydroxide. After the culture reached an $OD_{600}$ of 40, the temperature was reduced to 25° C. and the expression of halohydrin dehalogenase was induced by the addition of isopropyl-β-D-thiogalactoside (IPTG) (Sigma Chemical Corp., St. Louis, Mo.) to a final concentration of 1 mM. The culture was grown for another 15 hours. After the induction, the cells were harvested by centrifugation and washed with 10 mM potassium phosphate buffer, pH 7.0. The cell paste was used directly in the downstream recovery process or was stored at −80° C. until use.

(2) Ketoreductase Enzyme:

In an aerated agitated fermentor, 10.0L of growth medium containing 0.528 g/L ammonium sulphate, 7.5 g/L of dipotassium hydrogen phosphate trihydrate, 3.7 g/L of potassium dihydrogen phosphate, 2 g/L of Tastone-154 yeast extract, 0.05 g/L ferrous sulphate, and 3 ml/L of a trace element solution containing 2 g/L of calcium chloride dihydrate, 2.2 g/L of zinc sulfate septahydrate, 0.5 g/L manganese sulfate monohydrate, 1 g/L cuprous sulfate heptahydrate, 0.1 g/L sodium borate decahydrate and 0.5 g/L EDTA, was brought to a temperature of 30° C.

The fermentor was inoculated with a late exponential culture of Escherichia coli W3110 (pCR2–5) grown in a shake flask containing LB, 1% glucose (Sigma Chemical Co., St. Louis, Mo.), and 30 µg/ml chloroamphenicol (Sigma Chemical Co., St. Louis, Mo.) to a starting optical density at 600 nm ($OD_{600}$) of 0.5 to 2.0. The fermentor was agitated at 500–1500 rpm and air was supplied to the fermentation vessel at 1.0–15.0 L/min, and the pH of the culture was controlled at 7.0 by addition of 20% v/v ammonium hydroxide. After the culture reached an $OD_{600}$ of 40, the temperature was reduced to 25° C. and the expression of glucose dehydrogenase was induced by the addition of isopropyl-β-D-thiogalactoside (IPTG) (Sigma Chemical Corp., St. Louis, Mo.) to a final concentration of 1 mM. The culture was grown for another 15 hours. After the induction, the cells were harvested by centrifugation and washed with 10 mM potassium phosphate buffer, pH 7.0. The cell paste was used directly in the downstream recovery process or was stored at −80° C. until use.

(3) Glucose Dehydrogenase Enzyme:

In an aerated agitated fermentor, 10.0L of growth medium containing 0.528 g/L ammonium sulphate; 7.5 g/L of dipotassium hydrogen phosphate trihydrate; 3.7 g/L of potassium dihydrogen phosphate; 2 g/L of Tastone-154 yeast extract; 0.05 g/L ferrous sulphate; and 3 ml/L of a trace element solution containing 2 g/L of calcium chloride dihydrate, 2.2 g/L of zinc sulfate septahydrate, 0.5 g/L manganese sulfate monohydrate, 1 g/L cuprous sulfate heptahydrate; 0.1 g/l sodium borate decahydrate and 0.5 g/L EDTA, was brought to a temperature of 30° C.

The fermentor was inoculated with a late exponential culture of (pGDHS06 or pGDHM02) grown in a shake flask containing LB, 1% glucose (Sigma Chemical Co., St. Louis, Mo.), and 30 µg/ml chloroamphenicol (Sigma Chemical Co., St. Louis, Mo.) to a starting optical density at 600 nm ($OD_{600}$) of 0.5 to 2.0. The fermenter was agitated at 500–1500 rpm and air was supplied to the fermentation vessel at 1.0–15.0 L/min, and the pH of the culture was controlled at 7.0 by addition of 20% v/v ammonium hydroxide. After the culture reached an $OD_{600}$ of 40, the temperature was reduced to 25° C. and the expression of glucose dehydrogenase was induced by the addition of isopropyl-β-D-thiogalactoside (IPTG) (Sigma Chemical Corp., St. Louis, Mo.) to a final concentration of 1 mM. The culture was grown for another 15 hours. After the induction, the cells were harvested by centrifugation and washed with 10 mM potassium phosphate buffer, pH 7.0. The cell paste was used directly in the downstream recovery process or was stored at −80° C. until use.

(4) Formate Dehydrogenase

In an aerated agitated fermenter, 10.0L of autoclaved minimal medium containing 3.5 g/L of $NaNH_4HPO_4.4H_2O$, 7.5 g/L of $K_2HPO_4.3H_2O$, and 3.7 g/L of $KH_2PO_4$ (see Lageveen, et al., 1988, *Appl. Environ. Microbiol.* 54:2924. (1988)), 2 g/L $NH_4Cl$, 0.528 g/L $(NH_4)2SO_4$, pH 7.0, 5 ml/L of R2 trace elements (see Reisenberg, et al. *Appl. Microbiol. Biotechnol* 1990 34:77), 20 ml/L of 10% yeast extract solution in water, 5 ml/L 1 M $MgSO_4$, 40 ml/L of 50% glucose solution in water were added. The temperature of the medium was brought to 30° C.

Chloroamphenicol was added from a concentrated stock solution, to a final concentration of 30 µg/ml. The fermenter was inoculated with an overnight culture of *Escherichia coli* W3110 (pFDHPs3 or PFDHCb13) grown in a shake flask containing the above minimal medium with R2 trace element solution, pH 7.0, 0.2% yeast extract, 1% glucose, and 30 µg/ml chloroamphenicol to a starting optical density at 600 nm ($OD_{600}$) of 0.04–0.1. The air was supplied to the fermentation vessel at 5.0 L/min. the pH of the culture was maintained at 7.0 using a concentrated solution of potassium hydroxide in water. The culture was grown to an $OD_{600}$ of 12–15, at which time a feed solution of 50% glucose, 6% ammonium chloride and 0.5% magnesium sulfate was initiated at a rate that resulted in a final dissolved oxygen concentration of 30–40% of air saturation. The feed pump rate was controlled such that the dissolved oxygen in the fermenter was maintained around 30% at airflow rate of 10 L/min and agitation rate of 600 rpm. After the culture reached an $OD_{600}$ of 15 and had been exposed to the feeding regimen for a few hours, the expression of the formate dehydrogenase was induced by the addition of 1 mM of IPTG. The culture was grown for another 8–18 hours before it was harvested by centrifugation.

EXAMPLE 3

Enzyme Preparation (1) Ketoreductase

The cell paste was washed by suspending 1 volume wet weight of cell paste in 3 volumes of 100 mM Tris/sulfate (pH 7.2) followed by centrifugation at 5000 g for 40 minutes in a Sorval 12BP. The washed cell paste was suspended in 2 volumes of 100 mM Tris/sulfate (pH 7.2). The intracellular KRED was released from the cells by passing the suspension through a homogenizer in two passes using a pressure of 14,000 psig for the first pass and 8,000 psig for the second pass. The lysate was warmed to room temperature, then a 10% w/v solution of polyethyleneimine (PEI), pH 7.2, was added to the lysate to a final PEI concentration of 0.75% w/v and stirred for 30 minutes. The treated homogenate was centrifuged at 10,000 rpm in a Beckman lab centrifuge for 60 minutes. The supernatant was decanted and dispensed in shallow containers, frozen at −20° C. and lyophilized.

(2) Glucose Dehydrogenase

The cell paste was washed by suspending 1 volume wet weight of cell paste in 3 volumes of 100 mM Tris/sulfate (pH 7.2) followed by centrifugation at 5000 g for 40 minutes in a Sorval 12BP. The washed cell paste was suspended in 2 volumes of 100 mM Tris/sulfate (pH 7.2). The intracellular HHDH was released from the cells by passing the suspension through a homogenizer in two passes using a pressure of 14,000 psig for the first pass and 8,000 psig for the second pass. The homogenate was centrifuged at 10,000 rpm in a Beckman lab centrifuge for 60 minutes. The supernatant was decanted and dispensed in shallow containers, frozen at −20° C. and lyophilized.

(3) Halohydrin Dehalogenase

The cell paste was washed by suspending 1 volume wet weight of cell paste in 3 volumes of 100 mM Tris/sulfate (pH 7.2) followed by centrifugation at 5000 g for 40 minutes in a Sorval 12BP. The washed cell paste was suspended in 2 volumes of 100 mM Tris/sulfate (pH 7.2). The intracellular HHDH was released from the cells by passing the suspension through a homogenizer in two passes using a pressure of 14,000 psig for the first pass and 8,000 psig for the second pass. The cell lysate was allowed to cool to 4° C. between passes through the homogenizer. The homogenate was centrifuged at 10,000 rpm in a Beckman lab centrifuge for 60 minutes. The supernatant was decanted and dispensed in shallow containers, frozen at −20° C. and lyophilized to a powder that was stored at −80° C.

To assess the quality of the preparation after fermentation, cell lysate containing the expressed halohydrin dehalogenase enzyme was assayed according to the following protocol. Approximately 50 µl of clarified cell lysate in 100 mM Tris-$SO_4$, 100 mM NaCN, pH 8.0 was mixed with 10 mM ethyl-(S)-4-chloro-3-hydroxybutyrate (Sigrna Aldrich, St. Louis, Mo. or prepared in accordance with the ketoreductase-catalyzed methods described herein). The total reaction volume was 0.2 ml. The reaction was incubated at room temperature for 30 min to 1 hour. The reaction was extracted with 7 volumes of ethyl acetate and the organic layer removed to a 1.8 ml GC vial. The organic layer was analyzed by GC for presence of the ethyl-(R)-4-cyano-3-hydroxybutyrate product. The amount of product produced was determined by comparison to a standard curve prepared and analyzed under the same conditions.

(4) Formate Dehydrogenase

Cell lysate containing expressed formate dehydrogenase was prepared by homogenization of cell paste in 1 volume 100 mM triethanolamine (pH 7.0) at 4° C. The cell lysate was allowed to cool to 4° C. between passes through the homogenizer. Cell lysate was clarified by centrifugation at 4° C. The clarified lysate was assayed as described in Example 4.

EXAMPLE 4

Characterization of Enzyme Activity (1) Ketoreductase (KRED)

To a solution of ethyl 4-chloro-3-ketobutyric acid ester (10 mM) in 100 mM potassium phosphate buffer (pH 7.0) was added the ketoreductase enzyme as a predissolved solution in the same buffer. The reaction was initiated by addition of NADPH (1 mM final) and the course of reaction was followed by measurement of the decrease of absorbance at 340 nm. This absorbance corresponds to the NADPH concentration. The results were plotted as Absorbance units (NADPH) vs. time, and the slope of the plot determined (Absorbance units/min). The slope of the Absorbance vs. time plot was converted to concentration units using the extinction coefficient of NADPH, and the activity of the ketoreductase was determined in units of μmol (NADPH consumed)/min/mg (total ketoreductase catalyst). The measurement can also be performed using fluorescent detection utilizing an excitation of 340 nm for NADPH with emission measured at 455 nm. Other substrates of interest may be substituted for ethyl 4-chloro-3-keto-butyric acid ester to evaluate ketoreductase activity with respect to other substrates.

(2) Glucose Dehydrogenase (GDH)

To a solution of 50 mM glucose in 100 mM potassium phosphate buffer (pH 7.0) was added the glucose dehydrogenase enzyme as a predissolved solution in the same buffer. The reaction was initiated by addition of NADP (1 mM final) and the course of reaction was followed by measurement of the increase of absorbance at 340 nm or of the fluorescence (excitation 340 nm, emission 455 nm). The results were plotted as Absorbance units (NADPH) vs. time, and the slope of the plot determined (Absorbance units/min). The slope of the Absorbance vs. time plot was converted to concentration units using the extinction coefficient of NADPH (see (1) above), and the activity of the glucose dehydrogenase was determined in units of μmol (NADPH created)/min/mg (total glucose dehydrogenase catalyst).

(3) Halohydrin Dehalogenase (HHDH)

To a solution of ethyl (S)-4-chloro-3-hydroxybutyrate (10 mM) in 300 mM potassium phosphate, 300 mM NaCN buffer (pH 8.0) was added the halohydrin dehalogenase enzyme as a predissolved solution in the same buffer. Over time, aliquots of the mixture were withdrawn and extracted with three volumes of ethyl acetate. The organic layer was then analyzed by gas chromatography (GC), as described hereinbelow in Example 6. Samples were taken at various time points, and the peak area of the product cyanohydrin, ethyl (R)-4-cyano-3-hydroxybutyrate, was plotted as a function of time. The peak areas were converted to concentration units using a standard curve that was prepared for the ethyl (R)-4-cyano-3-hydroxybutyrate. Activity of the halohydrin dehalogenase was determined in units of μmol (cyanohydrin produced)/min/mg (total halohydrin dehalogenase catalyst). Other nucleophiles and/or substrates of interest may be substituted for cyanide to evaluate halohydrin dehalogenase activity with respect to other nucleophiles and/or substrates.

(4) Formate Dehydrogenase

To a solution of 150 mM formate in 100 mM triethanolamine buffer (pH 7.0) was added the formate dehydrogenase enzyme as a predissolved solution in the same buffer. The reaction was initiated by addition of NAD (2 mM final) and the course of reaction was followed by measurement of the increase of absorbance at 340 nm or of the fluorescence (excitation 340 nm, emission 455 nm). The results were plotted as Absorbance units (NADH) vs. time, and the slope of the plot determined (Absorbance units/min). The slope of the Absorbance vs. time plot was converted to concentration units using the extinction coefficient of NADH, and the activity of the formate dehydrogenase was determined in units of μmol (NADH created)/min/mg (total formate dehydrogenase catalyst).

EXAMPLE 5

Preparation of ethyl (R)-4-cyano-3-hydroxybutyrate from ethyl 4-chloroacetoacetate (via ethyl (S)-4-chloro-3-hydroxybutyrate)

To a well-stirred solution of 100 mM potassium phosphate buffer, 500 mM NaCl, pH 7 (1 L) at room temperature was added glucose (160 g, 830 mmoles, 1.1 equiv). To this was added ketoreductase SEQ ID NO: 2 (0.9 g), glucose dehydrogenase SO6 SEQ ID NO: 10 (0.5 g) and NADP (0.5 g) as lyophilized powders. Once dissolved, butyl acetate (500 mL) was added to form an emulsion. To this emulsion was added a solution of ethyl 4-chloroacetoacetate (100 g, 608 mmoles) in butyl acetate (500 mL), dropwise over 3 hours. The pH was maintained between 6.8 and 7 by an automatic titrater that dispensed Na$_2$CO$_3$ (2M in water, about 160 mL total). After 40 hours the automated addition of the base had ceased and there was no residual starting material by gas chromatography. The layers were separated, and the aqueous phase was washed with ethyl acetate (500 mL). The combined organics were dried over anhydrous sodium sulfate, filtered and evaporated on a rotary evaporator, to give essentially pure (~97%) ethyl (S)-4-chloro-3-hydroxybutyrate.

To a well stirred solution of ethyl (S)-4-chloro-3-hydroxybutyrate (8.25 g, 50 mmoles) in 300 mM potassium phosphate buffer, 300 mM NaCN pH 8.0 (1L) at 30° C. was added halohydrin dehalogenase SEQ ID NO: 14 (9 g) as a lyophilized powder. After fifty seven hours the mixture was washed with ethyl acetate (2 times 250 mL) and the combined organics dried over anhydrous sodium sulfate. The mixture was filtered and evaporated on a rotary evaporator to give essentially pure ethyl (R)-4-cyano-3-hydroxybutyrate, as determined using the gas chromatography method and elution time data described in Example 6, hereinbelow.

This example shows the process of the invention wherein a 4-cyano-3-hydroxybutyric acid ester (ethyl (R)-4-cyano-3-hydroxybutyrate) is produced by contacting a 4-halo-3-hydroxybutyric acid ester (ethyl (S)-4-chloro-3-hydroxybutyrate) with a halohydrin dehalogenase and cyanide (provided by a cyanide salt, NaCN). It further shows the process of the invention wherein the 4-halo-3-hydroxybutyric acid ester is provided by contacting a 4-halo-3-ketobutyric acid ester (ethyl 4-chloroacetoacetate) with a ketoreductase, a cofactor (NADPH, provided as NADP), and a cofactor regeneration system (glucose and glucose dehydrogenase). It further shows the overall production of nonracemic chiral ethyl (R)-4-cyano-3-hydroxybutyrate from achiral ethyl 4-chloroacetoacetate in high e.e. and in high purity without extensive purification procedures.

EXAMPLE 6

Characterization of Ethyl (R)-4-cyano-3-hydroxybutyrate

The ethyl 4-cyano-3-(R)-hydroxybutyrate produced in Example 5 was analyzed using gas chromatography with flame ionization (FID) detection using an Agilent HP-5 column, 30 m long, 0.25 μm inner diameter, using the following program: 1 minute at 100° C., 5° C./minute for 10 minutes; 25° C./minute for 2 minutes; then 2 minutes at 200° C. Inlet and outlet temperatures were both 300° C., and the flow rate was 2 ml/minute. Under these conditions, ethyl (R)-4-cyano-3-hydroxybutyrate elutes at 6.25 minutes, ethyl (S)-4-chloro-3-hydroxybutyrate elutes at 4.5 minutes, and ethyl 4-chloroacetoacetate elutes at 4.1 minutes.

Chemical purity of the species was measured using the integrated peak areas from the gas chromatography results.

Enantioselectivity of the halohydrin dehalogenase (HHDH) with respect to ethyl (R)-4-cyano-3-hydroxybutyrate was measured by gas chromatography and FID detection using a Restek gammadex SA column (30 m long, 0.32 μm inner diameter) using the following program: 25 minutes at 165° C. and flow rate at 2 ml/min. Inlet and outlet temperatures were both at 230° C. Under these conditions ethyl (R)-4-cyano-3-hydroxybutyrate elutes at 19.6 minutes and ethyl (S)-4-cyano-3-hydroxybutyrate elutes at 19.2 minutes.

EXAMPLE 7

Preparation of Ethyl (S)-4-chloro-3-hydroxybutyrate from Ethyl 4-chloro-acetoacetate To a 3-necked jacketed 3L flask equipped with a mechanical stirrer and connected to an automatic titrater by a pH electrode and a feeding tube for addition of base, was charged triethanolamine (6.6 mL) and $H_2O$ (492 mL) to make 100 mM triethanolamine solution. The pH was adjusted to 7 with 37% HCl. Then, D-Glucose (125 g) was added. The water circulating to the flask jacket was set to 30° C. After 10 minutes, ketoreductase SEQ ID NO: 2 (5.7 g) and glucose dehydrogenase SO6 SEQ ID NO: 10 (3.1 g) powder were added. After 10 minutes, β-NAD (125 mg) was added and the resulting mixture was allowed to stir for 5 minutes. Then, butyl acetate (250 mL) was charged. Using an addition funnel, 2.4 M ethyl 4-chloroacetoacetate (250 mL, 100 g in 167 mL of butyl acetate) was slowly added over 3 hrs. The pH was maintained at 7 by the automatic titrater by the addition of 2 M $Na_2CO_3$ (152 mL) over 15 hrs. Subsequently, gas chromatography of a reaction sample showed complete conversion to product. Celite (16 g) was added and the reaction mixture was allowed to stir for 10 minutes. The solution was filtered through a celite pad and the organic layer was separated. The aqueous layer was extracted with butyl acetate (2×200 mL). The organic layers were combined and the solvent removed under vacuum by rotary evaporation to obtain 87 g of the ethyl (S) 4-chloro-3-hydroxybutyrate. The enantiomeric excess was >99%, as determined after its conversion to ethyl (R)-4-cyano-3-hydroxybutyrate in Example 8.

EXAMPLE 8

Preparation of Ethyl (R)-4-cyano-3-hydroxybutyrate from Ethyl (S)-4-chloro-3-hydroxybutyrate To a 3-necked jacketed 3L flask equipped with a mechanical stirrer and connected to an automatic titrater by a pH electrode and a feeding tube for addition of base, was charged $H_2O$ (1200 mL), NaCN (37.25 g) and $NaH_2PO_4$ (125 g) to bring the solution to pH 7. The water circulator was set to 40° C. After 10 minutes, halohydrin dehalogenase SEQ ID NO: 32 as cell lysate (250 mL) was added. The reaction mixture was allowed to stir for 5 minutes. Using an addition funnel, ethyl (S)-4-chloro-3-hydroxybutyrate (45 g of the material from Example 7) was slowly added over 1 hour. The pH was maintained at 7 by the automatic titrater by the addition of 10 M NaOH (27 mL) over 17 hrs. Subsequently, gas chromatography of a reaction sample showed complete conversion to product. Celite (16 g) was added to the flask, which was then connected to a diaphragm, whose exhaust is bubbled into 5M NaOH (200 mL), to remove HCN. The mixture was heated to 60° C. under 100 mm Hg pressure. After 1 hour a submerged air bubbler was added to the solution to aid the removal of the HCN. After 3 hours, an HCN detector indicated less than 5 ppm HCN in the off-gas. The mixture was allowed to cool to room temperature, then filtered through a celite pad. The filtrate was extracted with butyl acetate (3×800 mL) and the combined organic layers filtered through a pad of activated charcoal. The solvent was removed under vacuum by rotary evaporation to provide 28.5 g of ethyl (R)-4-cyano-3-hydroxybutyrate. The purity was 98% (w/w) by HPLC and the enantiomeric excess was >99% (by chiral GC, the S enantiomer was undetectable).

EXAMPLE 9

Preparation of Ethyl (S)-4-chloro-3-hydroxybutyrate from Ethyl 4-chloro-acetoacetate To a 100 mL vessel connected to an automatic titrater by a pH electrode and a feeding tube for addition of base was charged a solution of glucose (7.5 g) in 100 mM triethanolamine pH 7 buffer (25 mL). To this solution was charged ketoreductase SEQ ID NO: 42 (100 mg); 50 mg GDH SEQ ID NO: 66 and NADP (6.25 mg). Butyl acetate (10 ml) was then charged. Then, ethyl 4-chloroacetoacetate (6 g) in butyl acetate (10 mL) was charged. The pH was maintained at 7 by the automatic titrater by the addition of 4M NaOH (7.5 mL) over 7 hrs. A sample of the reaction mixture was extracted with an equal volume of butyl acetate and the organic layer was analyzed by GC. The analysis showed 99% conversion of the ethyl 4-chloroacetoacetate to ethyl (S)-4-chloro-3-hydroxybutyrate.

EXAMPLE 10

Preparation of Ethyl (S)-4-chloro-3-hydroxybutyrate from Ethyl 4-chloro-acetoacetate The procedure was identical to Example 9 with the exceptions that 400 mg of the ketoreductase SEQ ID NO: 42 was used and NAD+ (12.5 mg) was added in place of the NADP. The addition of the NaOH solution by the automatic titrater was complete in 11 hours and the GC analysis showed 99% conversion of the ethyl 4-chloroacetoacetate to ethyl (S)-4-chloro-3-hydroxybutyrate.

EXAMPLE 11

Preparation of Ethyl (S)-4-chloro-3-hydroxybutyrate from Ethyl 4-chloro-acetoacetate To a 100 mL vessel connected to an automatic titrater by a pH electrode and a feeding tube for addition of base was charged a solution of glucose (12 g) in water (30 mL). To this solution was charged ketoreductase SEQ ID NO: 42 (100 mg); 50 mg GDH SEQ ID NO: 66 and NADP (6.25 mg). Butyl acetate (10 ml) was then charged. Ethyl 4-chloroacetoacetate (10 g) was then charged via syringe pump as follows: 1 mL was charged rapidly and the remainder was then charged at a rate of 1 mL/hr). The pH was maintained at 7 by the automatic titrater by the addition of 4M NaOH over 18 hours hrs. The stirring was stopped and the phases allowed to separate. The organic layer included some emulsion. The organic layer, including some emulsion, was separated and washed with 10 mL of water. The combined aqueous layers were extracted twice with 20 mL of butyl acetate. The organic extracts were combined and rotary evaporated under vacuum to remove water. Additional butyl acetate was added during the evaporation to help remove the water. When the water was removed the butyl acetate solution was decanted from solids in the flask. Evaporation of the solvent under vacuum then gave 8.85 g of ethyl (S)-4-chloro-3-hydroxybutyrate (87.4% yield) of very good purity.

EXAMPLE 12

Preparation of Ethyl (R)-4-cyano-3-hydroxybutyrate from Ethyl (S)-4-chloro-3-hydroxybutate To a 170 mL vessel connected to an automatic titrater by a pH electrode and a feeding tube for addition of base was charged NaCN (1.5 g, 31 mmol) and water (50 mL). The vessel was sealed and the headspace was deaerated with nitrogen. The pH was adjusted to 7 by the addition of conc. $H_2SO_4$ (0.9 mL). The reaction mixture was heated to 40° C. and treated with a solution of halohydrin dehalogenase SEQ ID NO: 32 (1.2 g in 10 mL water containing 42 μL of 14M β-mercaptoethanol). Then, ethyl (S)-4-chloro-3-hydroxybutyrate (1.8 g, 10.8 mmol) was added via syringe. The automatic titrater maintained the pH at 7 by the addition of 2M NaOH. After 15 hr the reaction was complete and a total of 4.6 mL 2M NaOH had been added. A sample of the reaction mixture was extracted with an equal volume of butyl acetate. GC analysis of the organic extract showed the conversion of the ethyl (S)-4-chloro-3-hydroxybutyrate to ethyl (R)-4-cyano-3-hydroxybutyrate was >99%.

EXAMPLE 13

Preparation of Ethyl (R)-4-cyano-3-hydroxybutyrate from Ethyl (S)-4-chloro-3-hydroxybutyrate The procedure was identical to Example 12 with the exception that 4M NaCN was used as the base instead of the 2M NaOH. After 8 hrs, the reaction was complete and a total of 2.3 mL 4M NaCN had been added. By GC analysis, the conversion of the ethyl (S)-4-chloro-3-hydroxybutyrate to ethyl (R)-4-cyano-3-hydroxybutyrate was >99%.

This example shows the process of the invention using an alkali cyanide as base to maintain both the pH and the cyanide concentration of the reaction mixture constant.

EXAMPLE 14

Preparation of Ethyl (R)-4-cyano-3-hydroxybutate from Ethyl (S)-4-chloro-3-hydroxybutate To a 250 mL vessel connected to an automatic titrater by a pH electrode and a feeding tube for addition of base (7.5 M NaOH) was charged water (83.5 mL) and 0.7 g of halohydrin dehalogenase SEQ ID NO: 24. The mixture was stirred for 30 minutes. The titrater was activated and set to maintain pH 7. Then, 25% aqueous HCN (9.26 ml, 8.6 g) was charged over 20 minute to make a 2.3% HCN solution. The mixture was heated at 40° C. for 10 minutes, then ethyl (S)-4-chloro-3-hydroxybutyrate (5 g) was charged over 1 hour. The automatic titrater maintained the pH at 7 by the addition of 2M NaOH. After 20 hrs, GC analysis of a butyl acetate extract of a reaction sample showed the conversion of the ethyl (S)-4-chloro-3-hydroxybutyrate to ethyl (R)-4-cyano-3-hydroxybutyrate was 95%.

This example shows the process of the invention using aqueous hydrocyanic acid as the source of cyanide.

EXAMPLE 15

Preparation of Ethyl (R)-4-cyano-3-hydroxybutyrate from Ethyl (S)-4-chloro-3-hydroxybutyrate To a 20 mL screw-cap vial was added NaCN (250 mg) and $NaH_2PO_4$ (830 mg). Water (10 mL) was added followed by halohydrin dehalogenase SEQ ID NO: 32 as lyophilized powder (200 mg). Then ethyl (S)-4-chloro-3-hydroxybutyrate (300 mg) was added. The vial was capped and heated in an oil bath at 40° C. After 4 hours, GC analysis of a butyl acetate extract of a reaction sample extract showed of 54% conversion of the ethyl (S)-4-chloro-3-hydroxybutyrate to ethyl (R)-4-cyano-3-hydroxybutyrate. After 72 hrs, the GC analysis showed complete conversion.

EXAMPLE 16

Preparation of Ethyl (S)-4-cyano-3-hydroxybutyrate from Ethyl (R)-4-chloro-3-hydroxybutyrate The procedure was identical to that of Example 15 with the exceptions that the (R)-enantiomer of the Ethyl 4-chloro-3-hydroxybutyrate was reacted instead of the (S)-enantiomer and the quantities of all reaction components were halved. After 1 hour reaction time, the GC analysis showed 55% conversion of the ethyl (R)-4-chloro-3-hydroxybutyrate to ethyl (S)-4-cyano-3-hydroxybutyrate.

This example in combination with preceding examples shows that the process of the invention may be used to convert either enantiomer of the 4-halo-3-hydroxybutyric acid ester to the corresponding enantiomer of the 4-cyano-3-hydroxybutyric acid ester.

EXAMPLE 17

Preparation of Methyl (S)-4-chloro-3-hydroxybutyrate From Methyl 4-chloro-acetoacetate The procedure was identical to that of Example 9 with the exceptions that an equimolar amount of methyl 4-chloroacetoacetate was reacted instead of the ethyl 4-chloroacetoacetate and the enzymes used were ketoreductase SEQ ID NO: 50 and glucose dehydrogenase SEQ ID NO: 62. The reaction was completed in 11 hrs and the GC analysis showed >99% methyl (S)-4-chloro-3-hydroxybutyrate. The product was isolated by extraction into butyl acetate and solvent evaporation and its identity confirmed by $^1$H and $^{13}$C NMR.

EXAMPLE 18

Preparation of Methyl (R)-4-cyano-3-hydroxybutyrate From Methyl (S)-4-chloro-3-hydroxybutyrate The procedure was identical to that of Example 16 with the exception that an equimolar amount of methyl (S)-4-chloro-3-hydroxybutyrate (prepared by Example 17) was reacted instead of ethyl (R)-4-chloro-3-hydroxybutyrate. After 1 hour reaction time, the GC analysis showed 38% conversion of the methyl (R)-4-chloro-3-hydroxybutyrate to methyl (S)-4-cyano-3-hydroxybutyrate. The product was characterized by $^1$H and $^{13}$C NMR.

EXAMPLE 19

Preparation of Ethyl (R)-4-cyano-3-hydroxybutyrate from Ethyl (S)-4-bromo-3-hydroxybutyrate The procedure was identical to that of Example 16 with the exception that an equimolar amount of ethyl (S)-4-bromo-3-hydroxybutyrate was reacted instead of ethyl (R)-4-chloro-3-hydroxybutyrate. After 1 hour reaction time, the GC analysis showed 90% conversion of the ethyl (S)-4-bromo-3-hydroxybutyrate to ethyl (S)-4-cyano-3-hydroxybutyrate. The product was characterized by $^1$H and $^{13}$C NMR.

This example shows that the process of the invention wherein the halo substituent of the 4-halo-3-hydroxybutyric acid ester is bromine.

EXAMPLE 20

Preparation of Ethyl 3-hydroxybutyrate from Ethyl acetoacetate

The procedure was identical to that of Example 17 with the exceptions that an equimolar amount of ethyl acetoacetate was reacted instead of the methyl 4-chloroacetoacetate and 200 mg of ketoreductase SEQ ID NO: 50 and 100 mg of glucose dehydrogenase SEQ ID NO: 62 were used. The reaction was completed in 6 hrs. The product was isolated by extraction into butyl acetate and solvent evaporation and characterized by $^1$H and $^{13}$C NMR.

In combination with preceding examples, this example demonstrates that ketoreductase enzymes that have activity for the reduction of ethyl acetoacetate to ethyl 3-hydroxybutyrate are useful for the reduction 4-halo-3-ketobutyric acid esters to 4-halo-3-hydroxybutyric acid esters in embodiments of this invention.

EXAMPLE 21 pH profiles of enzymatic and nonenzymatic test reactions of ethyl 4-chloro-3-hydroxybutyrate with cyanide Aqueous solutions containing 25 mg/mL sodium cyanide were prepared at pH 5.0, 6.0, 7.0, 7.5, 8.0, 8.5, and 9.0 by the addition of 85% phosphoric acid while monitoring with pH meter. Halohydrin dehalogenase SEQ ID NO: 38 (20 mg) was added to each vial, followed by ethyl (S)-4-chloro-3-hydroxybutyrate (50 mg, 0.30 mmoles). For nonenzymatic reactions experiments, the procedure was identical with the exception that the enzyme was omitted. The vials were capped and heated in an oil bath at 55° C. for 3 hrs, then removed and cooled to room temperature. A 0.4 mL sample of each reaction mixture was extracted with 1 mL butyl acetate and the extracts were analyzed by gas chromatography.

The analyzed amounts of substrate and products in each vial are given in Table I, and graphed vs. pH in FIG. 1. In both, chlorohydrin means ethyl (S)-4-chloro-3-hydroxybutyrate, cyanohydrin means ethyl (R)-4-cyano-3-hydroxybutyrate, and crotonate means ethyl 4-hydroxycrotonate. In the Table, ND means not detected.

TABLE I

Millimoles chlorohydrin, cyanohydrin and crotonate by-product analyzed in test reactions with and without halohydrin dehalogenase. See Example 21

| | without halohydrin dehalogenase | | | with halohydrin dehalogenase | | |
|---|---|---|---|---|---|---|
| PH | mmol chlorohydrin | mmol cyanohydrin | mmol crotonate | mmol chlorohydrin | mmol cyanohydrin | mmol crotonate |
| 5.0 | 0.33 | ND | ND | 0.27 | ND | ND |
| 6.0 | 0.29 | ND | ND | 0.07 | 0.20 | ND |
| 7.0 | 0.30 | ND | ND | 0.01 | 0.28 | ND |
| 7.5 | 0.31 | ND | ND | 0.004 | 0.30 | ND |
| 8.0 | 0.30 | 0.01 | ND | 0.002 | 0.29 | ND |
| 8.5 | 0.21 | 0.05 | 0.001 | 0.001 | 0.24 | ND |
| 9.0 | 0.11 | 0.10 | 0.002 | 0.001 | 0.21 | ND |

The pHs of the final test reaction mixtures were remeasured. For the mixtures including halohydrin dehalogenase with initial pHs of 7 or above (being the mixtures in which near complete conversion of the chlorohydrin to the cyanohydrin occurred, the final mixture pHs were 0.4 to 0.6 pH units below the initial pHs. The other mixtures showed much lesser changes in pH from their initial values.

These data show that under these reaction conditions and time, no measurable nonenzymatic reaction of the ethyl 4-chloro-3-hydroxybutyrate with cyanide occurred at any tested pH less than 8. At pH 8 and above, increasing nonenzymatic reaction with cyanide to form ethyl 4-cyano-3-hydroxybutyrate occurred with increasing pH and was accompanied by increasing formation of ethyl 4-hydroxycrotonate by-product. In contrast, the enzymatic reaction with halohydrin dehalogenase occurred at all the tested pH's greater than 5 and with no detectable formation of ethyl 4-hydroxycrotonate at any tested pH. Additionally, for both enzymatic and nonenzymatic test reactions at pH greater than 8, the mole total of the GC-analyzed products decreased from the initial 0.30 mmoles provided (as ethyl 4-chloro-3-hydroxybutyrate reactant) indicating the increasing formation of non-analyzable by-products with increasing pH greater than 8. It was separately established that the ester group of the reactant and product are increasingly hydrolyzed to carboxylic acid groups at pHs greater than 8 and that the resulting carboxylic acids are not extracted in to the extracts of reaction mixture samples that are analyzed by GC. See Example 22.

EXAMPLE 22

Nonenzymatic hydrolysis of ethyl 4-cyano-3-hydroxybutyrate

Aqueous phosphate solutions were prepared at pH 7.0, 7.5, 8.0, 8.5, and 9.0 by dissolving 0.48 g of $NaH_2PO_4$ in 40 mL water and adjusting the pH by addition of 2M NaOH while monitoring with pH meter. 5 mL of each solution was charged to a separate 20 mL screw cap vial. Then, ethyl (R)-4-cyano-3-hydroxybutyrate (46 mg, 0.29 mmol) was added. The vials were capped and heated in an oil bath at 55° C. for 3 hrs, then cooled to room temperature. A 0.4 mL of each reaction mixture was extracted with 1 mL butyl acetate and the extracts were analyzed by GC. For an external standard a duplicate of the pH 7.0 mixture was freshly prepared and immediately extracted. The analyzed amounts of ethyl 4-cyano-3-hydroxybutyrate in each vial are given in Table II. No product of its hydrolysis was detected in the reaction sample extracts. It was separately established that the carboxylic acid product of hydrolysis of this ester is not extracted into the extracts of the reaction samples that are analyzed by GC.

TABLE II

Millimoles chlorohydrin and cyanohydrin analyzed in test hydrolysis reactions. See Example 22

| pH | mmol cyanohydrin |
| --- | --- |
| 7.0 | 0.29 |
| 7.5 | 0.28 |
| 8.0 | 0.27 |
| 8.5 | 0.26 |
| 9.0 | 0.24 |

The pHs of the final test mixtures were remeasured. The mixtures with initial pHs of 8.0, 8.5, and 9.0 each had a final pH of 7.4. The mixture with an initial pH of 7.5 had a final pH of 7.3, and the mixture with an initial pH of 7 was unchanged. This evidences the production of carboxylic acid in the higher pH samples causing neutralization of the solutions into the phosphate buffering range.

This example in combination with Example 21 shows that ethyl 4-cyano-3-hydroxy-butyrate is increasingly hydrolyzed with increasing pH at the pHs greater than 8 where it can be produced by nonenzymatic reaction of ethyl 4-chloro-3-hydroxybutyrate with cyanide.

EXAMPLE 23

Preparation of ethyl (R)-4-cyano-3-hydroxybutyrate from ethyl 4-chloroacetoacetate (via ethyl (S)-4-chloro-3-hydroxybutate)

To a 100 mL vessel connected to an automatic titrater by a pH electrode and a feeding tube for addition of base (4M NaOH) was charged a solution (25 mL) of glucose (7.5 g) in 100 mM triethanolamine buffer, pH 7. To this solution was charged ketoreductase SEQ ID NO: 50 (50 mg), glucose dehydrogenase SEQ ID NO: 62 (20 mg) and NADP (1.5 mg). Butyl acetate (10 ml) and ethyl 4-chloroacetoacetate (6 g) in additional butyl acetate (10 mL) were then charged. The pH was maintained at 7 by the automatic titrater by the addition of 4M NaOH to the stirring mixture over 13 hrs. The phases were then allowed to separate for 30 minutes and the organic layer (25 mL), containing the ethyl (S)-4-chloro-3-hydroxybutyrate intermediate, was removed.

To a 170 mL vessel connected to an automatic titrater by a pH electrode and a feeding tube for addition of base (2M NaOH) was charged sodium cyanide (1.5 g) followed by water (50 mL). The vessel was sealed and the headspace was deaerated with nitrogen. The pH was adjusted to 7 using concentrated sulfuric acid (0.9 mL). The mixture was heated to 40° C. and treated with a solution of halohydrin dehalogenase SEQ ID NO: 32 (1.2 g) in 10 mL water containing 42 uL of 14M β-mercaptoethanol). Then, the organic layer (25 mL) containing ethyl (S)-4-chloro-3-hydroxybutyrate from the first step was added via syringe. The pH was maintained at 7 by the automatic titrater by the addition of 2M NaOH to the stirring mixture. After 15 hr, the conversion of ethyl (S)-4-chloro-3-hydroxybutyrate to ethyl (R)-4-cyano-3-hydroxybutyrate was 33% as indicated by the cumulative addition of 5 mL of the base (15 mL expected for complete conversion).

EXAMPLE 24

Preparation of ethyl (R)-4-cyano-3-hydroxybutyrate from ethyl 4-chloroacetoacetate (via ethyl (S)-4-chloro-3-hydroxybutyrate)

To a 20 mL screw cap vial was added NaCN (125 mg, 2.55 mmol), $NaH_2PO_4$ (415 mg, 3.46 mmol) and glucose (750 mg, 3.8 mmol). Water (5 mL) was added followed by NADP (2 mg), ketoreductase SEQ ID NO: 56 (50 mg), glucose dehydrogenase SEQ ID NO: 62 (50 mg), and halohydrin dehalogenase SEQ ID NO: 32 (100 mg). Then ethyl 4-chloroacetoacete (24 mg, 0.15 mmol) in 0.5 mL butyl acetate was added. The vial was capped and heated in an oil bath at 30° C. After 1 hr, GC analysis of a butyl acetate extract of a reaction sample showed 100% conversion of the ethyl 4-chloro-acetoacete to ethyl (S)-4-chloro-3-hydroxybutyrate, at 96% selectivity, and ethyl (R)-4-cyano-3-hydroxybutyrate at 4% selectivity. Then, the reaction vial was heated to 40° C. for 15 hrs. GC analysis of a butyl acetate extract then showed 2% of the ethyl (S)-4-chloro-3-hydroxy-butyrate remaining, with overall 98% yield of ethyl (R)-4-cyano-3-hydroxybutyrate based on the starting ethyl 4-chloroacetate.

This example shows the process of the invention wherein a 4-cyano-3-hydroxybutyric acid ester (ethyl 4-cyano-3-(R)-hydroxybutyrate) is produced, via an intermediate 4-halo-3-hydroxybutyric acid ester (ethyl 4-chloro-3-(S)-hydroxybutyrate), by contacting a 4-halo-3-ketobutyric acid ester (ethyl 4-chloroacetoacetate) with a ketoreductase, a cofactor (NADPH, provided as NADP) a cofactor regeneration system (glucose and glucose dehydrogenase), a halohydrin dehalogenase, and cyanide (provided by an cyanide salt, NaCN) with all the reactants simultaneously present in the reaction mixture.

All publications, patents, patent applications, and other documents cited in this application are hereby incorporated by reference in their entirety for all purposes to the same extent as if each individual publication, patent, patent application, or other document were individually indicated to be incorporated by reference for all purposes.

While preferred embodiments of the invention have been illustrated and described, it will be appreciated that various changes can be made therein without departing from the spirit and scope of the invention.

We claim:

1. A method for producing a 4-cyano-3-hydroxybutyric acid ester from a 4-halo-3-hydroxybutyric acid ester, the method comprising:

(a) providing a 4-halo-3-hydroxybutyric acid ester, wherein the halo substituent is selected from the group consisting of chlorine, bromine, and iodine; and (b) contacting the 4-halo-3-hydroxybutyric acid ester with a halohydrin dehalogenase and cyanide under conditions sufficient to form a reaction mixture for converting the 4-halo-3-hydroxybutyric acid ester to a 4-cyano-3-hydroxybutyric acid ester.

2. The method of claim 1, wherein the 4-cyano-3-hydroxybutyric acid ester is a non-racemic chiral 4-cyano-3-hydroxybutyric acid ester.

3. The method of claim 1, wherein the cyanide is provided by hydrocyanic acid.

4. The method of claim 1, wherein the cyanide is provided by a cyanide salt.

5. The method of claim 1, wherein the halo substituent of the 4-halo-3-hydroxybutyric acid ester is selected from the group consisting of chlorine and bromine.

6. The method of claim 1, wherein the 4-halo-3-hydroxybutyric acid ester is a 4-chloro-3-hydroxybutyric acid ester.

7. The method of claim 1, wherein the 4-halo-3-hydroxybutyric acid ester is a lower alkyl ester.

8. The method of claim 1, wherein (1) the 4-halo-3-hydroxybutyric acid ester has the structure:

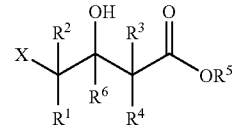

and (2) the 4-cyano-3-hydroxybutyric acid ester has the structure:

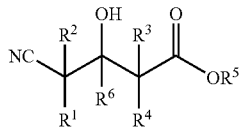

wherein:

X is a halogen selected from the group consisting of chlorine, bromine, and iodine;

$R^1$, $R^2$, $R^3$, $R^4$, and $R^6$ are each independently selected from the group consisting of hydrogen, fluorine, an optionally substituted lower alkyl, an optionally substituted cycloalkyl, an optionally substituted lower alkenyl, an optionally substituted aryl, an optionally substituted arylalkyl, amino, an optionally substituted lower alkylamino, an optionally substituted cycloalklyamino, an optionally substituted lower alkoxy, an optionally substituted cycloalkoxy, an optionally substituted aryloxy, and an optionally substituted arylalkoxy; and R⁵ is selected from the group consisting of an optionally substituted lower alkyl, an optionally substituted cycloalkyl, an optionally substituted aryl, and an optionally substituted arylalkyl.

9. The method of claim 1, wherein the halohydrin dehalogenase is a naturally occurring halohydrin dehalogenase.

10. The method of claim 1, wherein the halohydrin dehalogenase is a non-naturally occurring halohydrin dehalogenase.

11. The method of claim 1, wherein the reaction mixture for converting the 4-halo-3-hydroxybutyric acid ester to a 4-cyano-3-hydroxybutyric acid ester is maintained at a pH in the range of from about 5 to about 9.

12. The method of claim 11, wherein the reaction mixture for converting the 4-halo-3-hydroxybutyric acid ester to a 4-cyano-3-hydroxybutyric acid ester is maintained at a pH in the range of from about 5 to about 8.

13. The method of claim 1, wherein the reaction mixture for converting the 4-halo-3-hydroxybutyric acid ester to a 4-cyano-3-hydroxybutyric acid ester is maintained at a pH of about 8 or below.

14. The method of claim 1, wherein the reaction mixture for converting the 4-halo-3-hydroxybutyric acid ester to a 4-cyano-3-hydroxybutyric acid ester further comprises a pH buffer.

15. The method of claim 1, further comprising:
(c) adding a base sufficient to maintain the reaction mixture for converting the 4-halo-3-hydroxybutyric acid ester to a 4-cyano-3-hydroxybutyric acid ester at a pH of about 5 or above.

16. The method of claim 15 wherein the base is selected from hydroxide salts, carbonate salts, and bicarbonate salts.

17. The method of claim 15 wherein the base is selected from a cyanide salt.

18. The method of claim 1, further comprising recovering the 4-cyano-3-hydroxybutyric acid ester from the reaction mixture for converting the 4-halo-3-hydroxybutyric acid ester to a 4-cyano-3-hydroxybutyric acid ester.

19. The method of claim 16, further comprising purifying the 4-cyano-3-hydroxybutyric acid ester.

20. The method of claim 1, wherein step (a) further comprises
providing a 4-halo-3-ketobutyric acid ester,
wherein the halo substituent is selected from the group consisting of chlorine, bromine, and iodine; and
contacting the 4-halo-3-ketobutyric acid ester with a ketoreductase, a cofactor, and a cofactor regeneration system under conditions sufficient to form a reaction mixture for converting the 4-halo-3-ketobutyric acid ester to the 4-halo-3-hydroxybutyric acid ester.

21. The method of claim 20, wherein the cofactor is NAD/NADH.

22. The method of claim 20, wherein the cofactor is NADP/NADPH.

23. The method of claim 20, wherein the ketoreductase is a naturally occurring ketoreductase.

24. The method of claim 20, wherein the ketoreductase is a non-naturally occurring ketoreductase.

25. The method of claim 20, wherein the cofactor regeneration system comprises glucose and a glucose dehydrogenase.

26. The method of claim 25, wherein the glucose dehydrogenase is a naturally occurring glucose dehydrogenase.

27. The method of claim 25, wherein the glucose dehydrogenase is a non-naturally occurring glucose dehydrogenase.

28. The method of claim 20, wherein the cofactor regeneration system comprises formate and a formate dehydrogenase.

29. The method of claim 28, wherein the formate dehydrogenase is a naturally occurring formate dehydrogenase.

30. The method of claim 28, wherein the formate dehydrogenase is a non-naturally occurring formate dehydrogenase.

31. The method of claim 20, wherein
(1) the 4-halo-3-ketobutyric acid ester has the structure:

$$X\underset{R^1}{\overset{R^2}{C}}\underset{}{\overset{O}{C}}\underset{R^4}{\overset{R^3}{C}}\underset{}{\overset{O}{C}}OR^5$$

and
(2) the 4-halo-3-hydroxybutyric acid ester has the structure:

$$X\underset{R^1}{\overset{R^2}{C}}\underset{}{\overset{OH}{C}}\underset{R^4}{\overset{R^3}{C}}\underset{}{\overset{O}{C}}OR^5$$

and
(3) the 4-cyano-3-hydroxybutyric acid ester has the structure:

$$NC\underset{R^1}{\overset{R^2}{C}}\underset{}{\overset{OH}{C}}\underset{R^4}{\overset{R^3}{C}}\underset{}{\overset{O}{C}}OR^5$$

wherein:
X is a halogen selected from the group consisting of chlorine, bromine, and iodine;
$R^1$, $R^2$, $R^3$, and $R^4$ are each independently selected from the group consisting of hydrogen, fluorine, an optionally substituted lower alkyl, an optionally substituted cycloalkyl, an optionally substituted lower alkenyl, an optionally substituted aryl, an optionally substituted arylalkyl, amino, an optionally substituted lower alkylamino, an optionally substituted cycloalklyamino, an optionally substituted lower alkoxy, an optionally substituted cycloalkoxy, an optionally substituted aryloxy, and an optionally substituted arylalkoxy; and
$R^5$ is selected from the group consisting of an optionally substituted lower alkyl, an optionally substituted cycloalkyl, an optionally substituted aryl, and an optionally substituted arylalkyl.

32. The method of claim 20, wherein the reaction mixture for converting the 4-halo-3-ketobutyric acid ester to the 4-halo-3-hydroxybutyric acid ester is maintained at a pH in the range of from about 5 to about 10.

33. The method of claim 20, wherein the reaction mixture for converting the 4-halo-3-ketobutyric acid ester to the 4-halo-3-hydroxybutyric acid ester further comprises a buffer.

34. The method of claim 25, further comprising:
adding a base sufficient to maintain the reaction mixture for converting the 4-halo-3-ketobutyric acid ester to the 4-halo-3-hydroxybutyric acid ester at a pH of about 5 or above.

* * * * *